US011447782B2

(12) United States Patent
Bongiorni et al.

(10) Patent No.: US 11,447,782 B2
(45) Date of Patent: Sep. 20, 2022

(54) ENGINEERED RIBOSOMAL PROMOTERS FOR PROTEIN PRODUCTION IN MICROORGANISMS

(71) Applicant: DANISCO US INC., Palo Alto, CA (US)

(72) Inventors: Cristina Bongiorni, Palo Alto, CA (US); Marc Kolkman, Palo Alto, CA (US); Chris Leeflang, Palo Alto, CA (US); Virgil Arthur Rhodius, Palo Alto, CA (US); Anita Van Kimmenade, Palo Alto, CA (US)

(73) Assignee: DANISCO US INC., Palo Alto, CA (US)

( * ) Notice: Subject to any disclaimer, the term of this patent is extended or adjusted under 35 U.S.C. 154(b) by 713 days.

(21) Appl. No.: 16/081,082

(22) PCT Filed: Mar. 6, 2017

(86) PCT No.: PCT/US2017/020913
§ 371 (c)(1),
(2) Date: Aug. 30, 2018

(87) PCT Pub. No.: WO2017/152169
PCT Pub. Date: Sep. 8, 2017

(65) Prior Publication Data

US 2019/0085341 A1 Mar. 21, 2019

Related U.S. Application Data

(60) Provisional application No. 62/304,061, filed on Mar. 4, 2016.

(51) Int. Cl.
| | |
|---|---|
| *C07H 21/04* | (2006.01) |
| *C12N 15/75* | (2006.01) |
| *C12N 9/28* | (2006.01) |
| *C07K 14/32* | (2006.01) |
| *C12N 9/54* | (2006.01) |

(52) U.S. Cl.
CPC .............. *C12N 15/75* (2013.01); *C07K 14/32* (2013.01); *C12N 9/2417* (2013.01); *C12N 9/54* (2013.01); *C12Y 302/01001* (2013.01); *C12Y 304/21062* (2013.01)

(58) Field of Classification Search
CPC .......... C12N 15/75; C12N 15/67; C12N 9/52; C12N 15/1082; C12N 15/90; C12N 9/54; C12N 15/63; C12N 9/2417; C12P 21/02; C12Y 304/21062

USPC ......... 536/23.2; 435/320.1, 252.31, 200, 220

See application file for complete search history.

(56) References Cited

U.S. PATENT DOCUMENTS 4,559,300 A 12/1985 Kovacevic et al.

FOREIGN PATENT DOCUMENTS

WO 2013086219 A1 6/2013

OTHER PUBLICATIONS

Witkowski et al., Biochemistry 38:11643-11650, 1999.*
Whisstock et al., Quarterly Reviews of Biophysics 2003, vol. 36 (3): 307-340.*
Devos et al., Proteins: Structure, Function and Genetics, 2000, vol. 41: 98-107.*
International Search Report and Written Opinion from PCT Applicatin No. PCT/US2017/020913, dated Jul. 7, 2017, 17 pages.
Krasny et al., "An alternative strategy for bacterial ribosome synthesis: Bacillus subtilis rRna transcription regulation", The EMBO Journal, vol. 23, 2004, pp. 4473-4483.

Nijland et al., "Heterologous production and secretion of Clostridium perfringens beta-toxoid in closely related Gram-positive hosts", Journal of Biotechnology, vol. 127, No. 3, Dec. 1, 2006, pp. 361-372.

* cited by examiner

*Primary Examiner* — Robert B Mondesi
*Assistant Examiner* — Mohammad Y Meah

(57) ABSTRACT

The instant disclosure is generally related to novel engineered (hybrid) promoters. In certain embodiments, the instant disclosure is directed to one or more nucleic acid compositions comprising engineered promoters operably linked to nucleic acids encoding proteins of interest. Thus, the disclosure set forth herein described methods and compositions for the production of proteins of interest using one or more novel engineered (hybrid) promoters of the disclosure.

14 Claims, 7 Drawing Sheets

Specification includes a Sequence Listing.

```
                    1         10        20        30        40        50        60
                    |         |         |         |         |         |         |
PrrnO_P1            GCGCTTTTTTGTGTCATAACCCTTTACAGTCATAA-AAATTATGGTATAATCATTTCTG
PrrnO_P2            TAAAAACTTTTTCAAAAAGTATTGACCTAGTTAACTAAAAATGTTACTATTAAG--TA
PrrnA_P1            ATCATTTAATTGATATTATGATTGACTTAGACAACTGAAGGTGTTATTCTAATA--TA
PrrnA_P2            AAAAGAAATGCTAAAAAGTTGTTGACAGTAGCGGCGGTAAATGTTATGATAATAA-AG
PrrnJ_P1            TAGTATTCTTCAAAAAGTTATTGCACTATTATTACTAGGTGGTATATTATTATTCG
PrrnJ_P2            AAAAGAACTTCAAAAAGTTATTGACTTCACTGAGTCAACGAGTTATAATAATAA-AG
PrrnI_P1            TTAAATACTTTGAAAAAGTTGTTGACTTAAAAGAAGCTAAATGTTATAGTAATAA-AG
PrrnE_P1            ACAAAAAGTTTCCTAAGGTGTTTACAAGATTTT-AAAAATGTGTATAATAAGAA-AA
PrrnE_P2            CGAAAAACATTAAAAAACTTCTTGACTTCAACATCAAATGATAGTATGATAGTTA-AG
PrrnD_P1            GGATATTCTTTAAAAAAGGTGTTGACTCTGATTCTTGACCGTGTTATATTATTA--AA
PrrnD_P2            GGAAATAAATCAAAAAAACATTTGACAAAAGTCAAAATGTTATATTAATAA-AG
PrrnG_P1            GTGTAATTTTTAAAAAAGTTGACTTTGAAGAAGTGACATTGTATACTAATAA-AG
PrrnW_P1            CCAAAGTTTTTAAAAAAGTTGTTGACTTTGAAGAAGTGACGTTGTATACTAATAA-AG Consensus           DNRWDWWWWTTYWAAAAARKTRTTGACWDWRWWRWNDVWAVRTKKTATDHTAATAN-WR

FIG. 6
```

```
           1         10        20        30        40        50        60
           |         |         |         |         |         |         |
rrn1-P1    ATTCAATCTTTCAAATATAATCTTTTCATCAGGAACATAATGTGCTATAATTTCTCTTGG
rrn1-P2    AAAAACTTTTTTTAAAAAAGTATTGACCGCTTGTCT-TATAAATGTTATATTTAAG--TG
rrn2-P1    TTTATCGCAATATAATTTTTTGTTGACAAATATATT-TAAAGGTGTTAAATTAATATTTG
rrn2-P2    TAATTTTTTGAAAAAAGTTGTTGACGACATCACG-ATTAAATGTTAAGATATTA---TA
rrn3-P1    CAGAAAAACTTCAAAAAAACTTCTTGACTTTAACTGA-TATTCATAGTATTATAGTTA-AG
rrn4-P1    GGATATTTTATTAAAAAAGTGTTGACACTAATTTA-TAACGGTGATATATTATTAAGCG
rrn4-P2    CGACGAAAAATCAAAAAAACATTTGACACTTCTCGT-TGAAAATGTTATACTAATAA-AG
rrn5-P1    TAAATTTTTCTCAAAAAAAGTATTGCACAATCATAA-ATACGGTGGTATATTATTATTCG
rrn5-P2    AAAAGAACTTCAAAAAAACGTTCTTGACTTAATATCT-GAGATTGGATAATAATATAA-AG
rrn6-P1    AAGAAAAAAATTAAAAAAGAGGGTTGACCGGTTGACCGGAATTAAATAAACATGTTATATTGTTATTCG
rrn6-P2    AAAATAATTTTGAGAAAAGTTATTGACAAATATGTGAGCTTGATGTTATATTATTAA-AG Consensus  HDDHWWHWWYHWAAAAWRKTVTTGACHNHWHNWHDNDWWWVRTGDTAWAWTWWTNWNHG
```

FIG. 7

ENGINEERED RIBOSOMAL PROMOTERS FOR PROTEIN PRODUCTION IN MICROORGANISMS

CROSS-REFERENCE TO RELATED APPLICATION

This application claims the benefit of U.S. Provisional Application No. 62/304,061, filed on Mar. 4, 2016, which is hereby incorporated by reference in its entirety.

REFERENCE TO THE SEQUENCE LISTING

The contents of the electronic submission of the text file Sequence Listing, named "NB40928WOPCT-SequenceListing.txt" was created on Mar. 6, 2017 and is 72 KB in size, is hereby incorporated by reference in its entirety.

FIELD OF THE INVENTION

The present invention is generally related to the fields of molecular biology and genetic engineering. In certain embodiments, the present invention is directed to the use of engineered promoters, and more particularly, engineered hybrid ribosomal promoters for the expression and production of one or more proteins of interest in a host microorganism.

BACKGROUND OF THE INVENTION

Genetic engineering has facilitated various improvements in host microorganisms used as industrial bioreactors or cell factories. For example, Gram-positive *Bacillus* species produce and secrete a large number of useful proteins and metabolites. The most common *Bacillus* species used in industry are *B. licheniformis, B. amyloliquefaciens,* and *B. subtilis*. Because of their generally recognized as safe (GRAS) status, strains of *Bacillus* species are natural candidates for the production of proteins utilized in the food and pharmaceutical industries. For example, important production enzymes include α-amylases, neutral proteases, alkaline (or serine) proteases, and the like. However, in spite of advances in the knowledge of production of proteins in *Bacillus* host cells, there remains a need for methods and compositions thereof which improve the expression and production of these proteins by microorganisms.

Recombinant production of a protein of interest (POI) encoded by a gene (or ORF) of interest is typically accomplished by constructing expression vectors suitable for use in a desired host cell, wherein the nucleic acid encoding the desired POI is placed under the expression control of a promoter. Thus, the expression vector is introduced into a host cell by various techniques (e.g., via transformation), and production of the desired protein product is achieved by culturing the transformed host cell under conditions suitable for the expression and production of the protein product. For example, *Bacillus* promoters (and associated elements thereof) for the homologous and/or heterologous expression of functional polypeptides have been described in the art (e.g., see, PCT International Publication No. WO2013086219; U.S. Pat. No. 4,559,300; Kim et al., 2008, etc.).

While numerous promoters are known, there remains a need in the art for novel promoters which improve the expression of homologous and/or heterologous nucleic acids encoding proteins of interest. For example, in the industrial biotechnology arts, even small increases in the expression levels of an industrially relevant protein (e.g., an enzyme, an antibody, a receptor, and the like) translate into significant cost, energy and time savings of the POI produced. The novel and surprisingly effective engineered hybrid promoters of the present invention address such long felt needs in the art.

SUMMARY OF THE INVENTION

In certain embodiments, the present invention is directed to the use of engineered promoters, and more particularly, engineered hybrid ribosomal promoters for the expression and production of one or more proteins of interest in a host microorganism.

In particular embodiments, the present invention is directed to an isolated nucleic acid comprising an engineered hybrid promoter operably linked to a nucleic acid encoding a protein of interest (POI), wherein the hybrid promoter comprises the nucleotide sequence of any one of SEQ ID NO: 65, SEQ ID NO: 66, SEQ ID NO: 67, SEQ ID NO: 68, SEQ ID NO: 69, SEQ ID NO: 70, SEQ ID NO: 71 SEQ ID NO: 72, SEQ ID NO: 73, SEQ ID NO: 74, SEQ ID NO: 75, SEQ ID NO: 77, SEQ ID NO: 78, SEQ ID NO: 79, SEQ ID NO: 80, SEQ ID NO: 90, SEQ ID NO: 91, SEQ ID NO: 92, SEQ ID NO: 93, SEQ ID NO: 94, SEQ ID NO: 95, SEQ ID NO: 96 and SEQ ID NO: 97. In other embodiments, a nucleic acid of the invention comprises a subsequence of SEQ ID NOs: 65-80 and 90-97 that retains promoter activity. In other embodiments, a nucleic acid sequence of the invention is a nucleic acid that is at least 60% homologous to any one of SEQ ID NOs: 65-80 and 90-97, or a nucleic acid that hybridizes under medium stringency conditions with any one of SEQ ID NOs: 65-80 and 90-97 (or a subsequence thereof that retains promoter activity).

In certain embodiments, the hybrid promoter comprises the nucleotide sequence of SEQ ID NO: 65 or SEQ ID NO: 71. In certain other embodiments, the protein of interest (POI) encoded by the isolated nucleic acid is an enzyme. In particular embodiments, the enzyme is selected from the group consisting of acetyl esterases, aryl esterases, aminopeptidases, amylases, arabinases, arabinofuranosidases, carboxypeptidases, catalases, cellulases, chitinases, chymosin, cutinase, deoxyribonucleases, epimerases, esterases, α-galactosidases, β galactosidases, α-glucanases, glucan lyases, endo-β-glucanases, glucoamylases, glucose oxidases, α-glucosidases, β-glucosidases, glucuronidases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, pullulanases, mannanases, rhamno-galacturonases, ribonucleases, thaumatin, transferases, transport proteins, transglutaminases, xylanases and hexose oxidases.

In certain other embodiments, the present invention is directed to an isolated nucleic acid comprising an engineered complete promoter operably linked to a nucleic acid encoding a protein of interest, the isolated nucleic acid comprising the formula selected from:

| | |
|---|---|
| 5'-UP-1stPro-ORF-3'; | (I) |
| 5'-UP-1stPro-UTR-ORF-3'; | (II) |
| 5'-UP-1stPro-2ndPro-ORF-3'; | (III) |
| 5'-UP-1stPro-2ndPro-UTR-ORF-3'; | (IV) |

5'-UP-1stPro-UTR-2ndPro-UTR-ORF-3'; (V)

5'-UP-1stPro-2ndPro-3rdPro-ORF-3'; (VI)

5'-UP-1stPro-2ndPro-3rdPro-UTR-ORF-3; and (VII)

5'-UP-1stPro-2ndPro-UTR-3rdPro-UTR-ORF-3', (VIII)

wherein UP is a nucleic acid comprising a promoter upstream element, 1stPro, 2ndPro and 3rdPro are the same or different nucleic acids comprising at least a −35/−10 core promoter sequence, UTR is a nucleic acid comprising an untranslated region and ORF is a nucleic acid open reading frame encoding a protein of interest, wherein the UP element comprises any one of SEQ ID NOs: 45-61, a subsequence of SEQ ID NOs: 45-61 that retains promoter activity, a nucleic acid that is at least 60% homologous to any one of SEQ ID NOs: 45-61 that retains promoter activity or a nucleic acid that hybridizes under medium stringency conditions with any one of SEQ ID NOs: 45-61 or a subsequence thereof that retains promoter activity and wherein the 1stPro, 2ndPro and 3rdPro comprises any one of SEQ ID NOs: 1-39 and 101-154, a subsequence of SEQ ID NOs: 1-39 and 101-154 that retains promoter activity, a nucleic acid that is at least 60% homologous to any one of SEQ ID NOs: 1-39 and 101-154 that retains promoter activity, or a nucleic acid that hybridizes under medium stringency conditions with any one of SEQ ID NOs: 1-39 and 101-154 or a subsequence thereof that retains promoter activity.

In particular embodiments, the UTR comprises the nucleotide sequence of SEQ ID NO: 155. In certain other embodiments, the UP element comprises the nucleotide sequence of SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 57 or SEQ ID NO: 58.

In other embodiments, the 1stPro comprises a nucleotide sequence of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 14, SEQ ID NO: 15, SEQ ID NO: 16, SEQ ID NO: 17, SEQ ID NO: 18, SEQ ID NO: 19, SEQ ID NO: 26, SEQ ID NO: 85, SEQ ID NO: 89, SEQ ID NO: 101, SEQ ID NO: 102, SEQ ID NO: 103, SEQ ID NO: 104 or SEQ ID NO: 105.

In certain other embodiments, the 2ndPro comprises a nucleotide sequence of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 14, SEQ ID NO: 15, SEQ ID NO: 16, SEQ ID NO: 17, SEQ ID NO: 18, SEQ ID NO: 19, SEQ ID NO: 26, SEQ ID NO: 85, SEQ ID NO: 89, SEQ ID NO: 101, SEQ ID NO: 102, SEQ ID NO: 103, SEQ ID NO: 104 or SEQ ID NO: 105.

In yet other embodiments, the 3rdPro comprises a nucleotide sequence of SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 14, SEQ ID NO: 15, SEQ ID NO: 16, SEQ ID NO: 17, SEQ ID NO: 18, SEQ ID NO: 19, SEQ ID NO: 26, SEQ ID NO: 85, SEQ ID NO: 89, SEQ ID NO: 101, SEQ ID NO: 102, SEQ ID NO: 103, SEQ ID NO: 104 or SEQ ID NO: 105.

In particular embodiments, the POI encoded by the ORF is an enzyme. In certain other embodiments, the enzyme is selected from the group consisting of acetyl esterases, aryl esterases, aminopeptidases, amylases, arabinases, arabinofuranosidases, carboxypeptidases, catalases, cellulases, chitinases, chymosin, cutinase, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, pullulanases, mannanases, rhamno-galacturonases, ribonucleases, thaumatin, transferases, transport proteins, transglutaminases, xylanases, hexose oxidases.

In another embodiment, the invention is directed to an expression vector comprising a nucleic acid of the present disclosure. In other embodiments, the invention is directed to a bacterial host cell comprising an expression comprising a nucleic acid of the present disclosure.

In certain embodiments, a bacterial host cell of the present disclosure is a member of the genus *Bacillus*. In particular embodiments, the *Bacillus* host cell is selected from the group consisting of *B. subtilis*, *B. licheniformis*, *B. lentus*, *B. brevis*, *B. alkalophilus*, *B. amyloliquefaciens*, *B. coagulans*, *B. circulars*, *B. lautus*, *B. megatherium*, *B. thuringiensis* and *Geobacillus stearothermophilus*. In another embodiment, the *Bacillus* host cell is *B. subtilis* or *B. licheniformis*.

In certain other embodiments, the invention is directed to a *Bacillus* host cell comprising at least one copy of a nucleic acid of the present disclosure, wherein the at least one copy of the nucleic acid is comprised within an integration vector. In certain embodiments, the at least one copy of the nucleic acid is integrated into the chromosome or genome of the host cell.

In certain other embodiments, an integration vector comprising a nucleic acid of the instant disclosure is flanked at both the 5' and 3' ends with nucleic acid sequence homologous to a chromosomal loci of a host cell. In one particular embodiment, the host cell is a *Bacillus* cell and the 5' and 3' nucleic acid sequences are homologous to a *B. subtilis* aprE chromosomal loci yhfO comprising a nucleic acid of SEQ ID NO: 87 and *B. subtilis* aprE chromosomal loci yhfN comprising a nucleic acid of SEQ ID NO: 88. Thus, in particular embodiments, a *Bacillus* host cell comprising at least one copy of the nucleic acid of the present disclosure is integrated into the chromosome or episome of the *Bacillus* host cell.

In other embodiments, a protein of interest produced by a host cell of the disclosure is isolated from the host cell. In other embodiments, the isolated POI is purified.

In particular embodiments, a POI of the disclosure is an enzyme. In certain embodiments, the enzyme is selected from the group consisting of acetyl esterases, aryl esterases, aminopeptidases, amylases, arabinases, arabinofuranosidases, carboxypeptidases, catalases, cellulases, chitinases, chymosin, cutinase, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pullulanases, mannanases, pectin methyl esterases, pectinolytic enzymes, perhydrolases, polyol oxidases, peroxidases, phenoloxidases, phytases, polygalacturonases, proteases, pullulanases, mannanases, rhamno-galacturonases, ribonucleases, thaumatin, transferases, transport proteins, transglutaminases, xylanases, hexose oxidases.

In other embodiments, the invention is directed to a method for screening transformed (modified) host cells for increased expression of a POI comprising: (i) transforming a host cell with an isolated nucleic acid comprising a heterologous engineered hybrid promoter operably linked to a nucleic acid encoding a protein of interest (POI), wherein the hybrid promoter comprises the nucleotide sequence of any one of SEQ ID NO: 65, SEQ ID NO: 66, SEQ ID NO: 67, SEQ ID NO: 68, SEQ ID NO: 69, SEQ ID NO: 70, SEQ ID NO: 71 SEQ ID NO: 72, SEQ ID NO: 73, SEQ ID NO: 74, SEQ ID NO: 75, SEQ ID NO: 77, SEQ ID NO: 78, SEQ ID NO: 79, SEQ ID NO: 80, SEQ ID NO: 90, SEQ ID NO: 91, SEQ ID NO: 92, SEQ ID NO: 93, SEQ ID NO: 94, SEQ ID NO: 95, SEQ ID NO: 96 and SEQ ID NO: 97, (ii) transforming a host cell with an isolated nucleic acid comprising its native (wild-type) promoter operably linked to a nucleic acid encoding the same POI as step (i), wherein the host cells transformed in steps (i) and (ii) are host cells of the same Genus species and genetic background, and (iii) culturing the modified cells under conditions such that the POI is expressed, wherein an increase in the expression of the POI coding sequence in step (i), relative to the expression of the same POI coding sequence in step (ii), indicates increased expression of the POI.

In certain other embodiments, the invention is directed to a method for screening transformed (modified) host cells for increased expression of a POI comprising: (i) transforming a $1^{st}$ host cell with an isolated nucleic acid of the disclosure, (ii) transforming a $2^{nd}$ host cell with an isolated nucleic acid comprising its native (wild-type) promoter operably linked to a nucleic acid encoding the same POI as step (i), wherein the host cells transformed in steps (i) and (ii) are host cells of the same Genus species and genetic background, and (iii) culturing the modified cells under conditions such that the POI is expressed, wherein an increase in the expression of the POI coding sequence in step (i), relative to the expression of the same POI coding sequence in step (ii), indicates increased expression of the POI.

In another embodiments, the inventions is directed to a method for increasing the expression of a POI in a host cell comprising: (i) modifying a host cell by introducing into the host cell a nucleic acid comprising an engineered hybrid promoter operably linked to a nucleic acid encoding a protein of interest (POI), wherein the hybrid promoter comprises the nucleotide sequence of any one of SEQ ID NO: 65, SEQ ID NO: 66, SEQ ID NO: 67, SEQ ID NO: 68, SEQ ID NO: 69, SEQ ID NO: 70, SEQ ID NO: 71 SEQ ID NO: 72, SEQ ID NO: 73, SEQ ID NO: 74, SEQ ID NO: 75, SEQ ID NO: 77, SEQ ID NO: 78, SEQ ID NO: 79, SEQ ID NO: 80, SEQ ID NO: 90, SEQ ID NO: 91, SEQ ID NO: 92, SEQ ID NO: 93, SEQ ID NO: 94, SEQ ID NO: 95, SEQ ID NO: 96 and SEQ ID NO: 97, and (ii) culturing the modified host cell under conditions such that the POI is expressed.

In certain other embodiments, the invention is directed to a method for increasing the expression of a POI in a host cell comprising: (i) modifying a host cell by introducing into the host cell a nucleic acid of the present disclosure, and (ii) culturing the modified host cell under conditions such that the POI is expressed.

In particular embodiments of these methods, the host cell is selected from the group consisting of *B. subtilis*, *B. licheniformis*, *B. lentus*, *B. brevis*, *B. alkalophilus*, *B. amyloliquefaciens*, *B. coagulans*, *B. circulars*, *B. lautus*, *B. megatherium*, *B. thuringiensis* and *Geobacillus stearothermophilus*.

Figure 1:
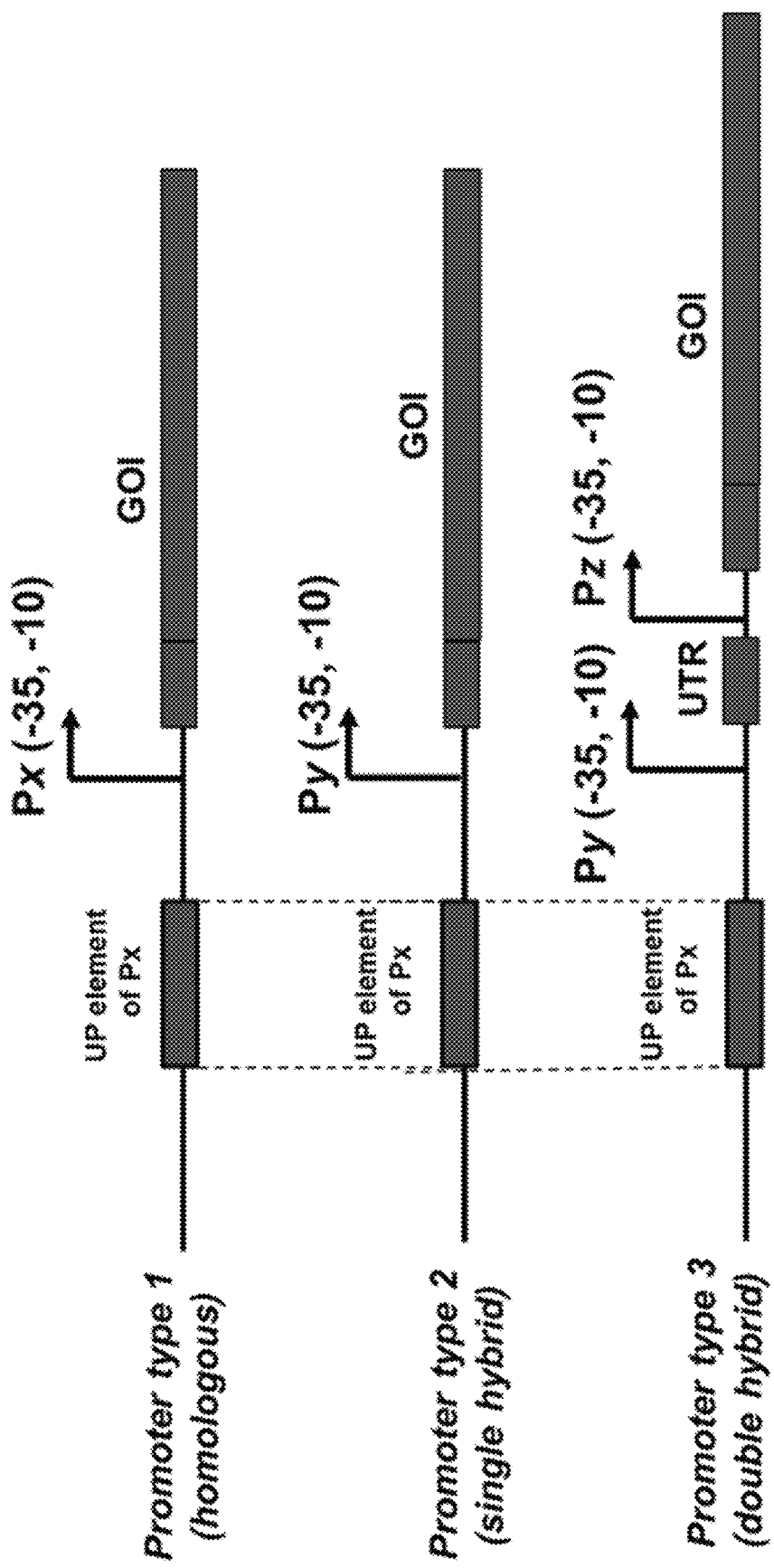
FIG. 1 shows a schematic representation of a homologous promoter (FIG. 1; Promoter Type 1), a single (engineered) hybrid promoter (FIG. 1; Promoter Type 2) and a double (engineered) hybrid promoter (FIG. 1; Promoter Type 3) of the instant disclosure. As depicted in FIG. 1, Promoter Type 1 comprises a promoter region designated "Px" and an upstream (UP) element designated "UP element of (promoter) Px", wherein the promoter Px and UP element of (promoter) Px are derived from the same (homologous) native promoter. In contrast, as depicted in FIG. 1, Promoter Type 2 (single hybrid) comprises a promoter region designated "Py" and an upstream (UP) element designated "UP element of (promoter) Px", wherein the promoter Py and the UP element of (promoter) Px are not derived from the same (homologous) native promoter, and as such, is a hybrid (combination) of a UP element and promoter derived from different (non-homologous) promoters. Similarly, as depicted in FIG. 1, Promoter Type 3 (double hybrid) comprises two promoter regions designated "Py" and "Pz" and a upstream (UP) element designated "UP element of (promoter) Px", wherein the two (double) promoters Py and Pz may comprise (i) the same nucleotide sequence (i.e., two identical promoter nucleic acid sequences; i.e., Py=Pz) or (ii) two different nucleotide sequences (i.e., the two promoters are derived from different promoter sources comprising different nucleic acid sequences, i.e., Py≠Pz), wherein the promoters Py and Pz are not derived from the same (homologous) native promoter as the UP element of (promoter) Px.

*thermophilus* α-amylase variant (SEQ ID NO: 64) and Amy4 is a *Cytophaga* sp α-amylase variant (SEQ ID NO: 63).

FIG. 6 shows multiple sequence alignments of various *B. subtilis* ribosomal RNA (rrn) promoters, displaying a sequence logo banner and the "consensus" sequence derived from the alignment of rrn promoters.

FIG. 7 shows multiple sequence alignments of various *B. licheniformis* ribosomal RNA (rrn) promoters, displaying a sequence logo for upstream elements and promoter sequences; and a "consensus" sequence derived from the alignment of the rrn promoters.

DETAILED DESCRIPTION OF THE INVENTION

The present invention provides novel compositions (and methods thereof) for the expression and production of one or more proteins of interest in a microbial host cell. In certain embodiments, the compositions (and methods thereof) comprise and are directed to engineered (modified) promoters. In particular embodiments, the engineered (modified) promoters of the present invention are derived from one or more *Bacillus* species ribosomal RNA promoter precursors and/or one or more *Bacillus* species ribosomal protein promoter precursors, collectively referred to herein as *Bacillus* species "ribosomal promoters". In certain embodiments, an engineered ribosomal promoter of the present disclosure may further comprise promoter nucleic acid sequence fragments derived from a *Bacillus* species promoter which is not a ribosomal RNA promoter or a ribosomal protein promoter.

In certain embodiments, the engineered ribosomal promoters of the present disclosure include, but are not limited to, engineered (hybrid) ribosomal RNA promoters, engineered (hybrid) ribosomal protein promoters and engineered (hybrid) combinations thereof. In further embodiments, novel production microorganism host cells and methods for producing one or more proteins of interest using one or more engineered (hybrid) ribosomal promoters are disclosed.

A. Definitions

Unless defined otherwise herein, all technical and scientific terms used herein have the same meaning as commonly understood by one of ordinary skill in the art to which this invention belongs (See e.g., Singleton, et al., 1994, Hale & Marham, 1991). Although any methods and materials similar or equivalent to those described herein can be used in the practice or testing of the present invention, the preferred methods and materials are described.

All patents, published patent applications and scientific references, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

As used herein, the terms "nucleic acid" and "nucleic acid sequence" refer to a nucleotide or polynucleotide sequence, and fragments or portions thereof, as well as to DNA, cDNA, and RNA of genomic or synthetic origin, which may be double-stranded or single-stranded, whether representing the sense or antisense strand. It will be understood that as a result of the degeneracy of the genetic code, a multitude of nucleotide sequences may encode a given protein.

As used herein, "polypeptide", "peptide" and "protein" are used interchangeably and include reference to a polymer of amino acid residues. The terms apply to amino acid polymers in which one or more amino acid residues are an artificial chemical analog of a corresponding naturally occurring amino acid, as well as to naturally occurring amino acid polymers. The terms also apply to polymers containing conservative amino acid substitutions such that the polypeptide remains functional.

As used herein, the phrase a "gene of interest" may be abbreviated "GOI", wherein the two terms are interchangeable. As used herein, the phrase a "protein of interest" may be abbreviated "POI", wherein the two terms are interchangeable. As used herein, the phrase an "open reading frame" may be abbreviated "ORF, wherein the two terms are interchangeable.

As used herein, the term "host cell" refers to a cell that has the capacity to act as a host and expression vehicle for an incoming sequence (i.e., a sequence introduced into the cell), as described herein. In certain embodiments, the host cell is a microorganism. In certain embodiments, the microorganism (host cell) is a Gram positive bacterial cell which is a Bacillaceae family member. In certain other embodiments, the microorganism (host cell) is a Gram positive bacterial cell which is a *Bacillus* genus member. In particular embodiments, the *Bacillus* host cell is selected from *B. subtilis, B. licheniformis, B. lentus, B. brevis, Geobacillus stearothermophilus, B. alkalophilus, B. amyloliquefaciens, B. clausii, B. sonorensis, B. halodurans, B. pumilus, B. lautus, B. pabuli, B. cereus, B. agaradhaerens, B akibai, B. clarkii, B. pseudofirmus, B. lehensis, B. megaterium, B. coagulans, B. circulars, B. gibsonii* and *B. thuringiensis.*

As used herein, the term "DNA construct" or "expression construct" refers to a nucleic acid sequence, which comprises at least two DNA (polynucleotide) fragments. A DNA or expression construct can be used to introduce nucleic acid sequences into a host cell. The DNA may be generated in vitro (e.g., by PCR) or any other suitable techniques. In certain embodiments, the DNA construct comprises a nucleic acid sequence of interest (e.g., a GOI or ORF) encoding a protein of interest. In particular embodiments, a DNA construct comprising a GOI or ORF is operably linked to an engineered promoter of the instant disclosure. In some embodiments, the DNA construct further comprises at least one selectable marker. In further embodiments, the DNA construct comprises sequences homologous to the host cell chromosome. In other embodiments, the DNA construct includes non-homologous sequences.

As used herein, the terms "nucleic acid encoding a protein of interest" or "coding sequence of interest" are used interchangeably and mean a nucleic acid sequence that encodes a protein of interest when translated into the protein. In some embodiments, the coding region is present in a cDNA form or ORF, while in other embodiments, it is present in genomic DNA or RNA form. When present in a DNA form, the oligonucleotide may be single-stranded (i.e., the sense strand) or double-stranded. In some embodiments, suitable control elements (e.g., enhancers, promoters, splice junctions, polyadenylation signals, etc.) are placed in close proximity to the coding region of the gene if needed to permit proper initiation of transcription and/or correct processing of the primary RNA transcript. Alternatively, in some embodiments, the coding region utilized in the expression vectors of the present invention contain endogenous enhancers, splice junctions, intervening sequences, polyadenylation signals, or a combination of both endogenous and exogenous control elements.

As defined herein, an "endogenous gene" refers to a gene in its natural location in the genome of an organism.

As defined herein, a "heterologous" gene, a "non-endogenous" gene, an "exogenous" gene, or a "foreign" gene refer to a gene (or open reading frame (ORF)) not normally found in the host organism, but rather is introduced into the host organism by gene transfer. Foreign (heterologous) genes comprise native genes (or ORFs) inserted into a non-native organism and/or chimeric genes inserted into a native or non-native organism. Thus, as used herein, the term "heterologous" in general refers to a polynucleotide or polypeptide that does not naturally occur in a host cell (i.e., exogenous to the host cell), or refers to a polynucleotide or polypeptide that is derived from the same genetic source or species as the host cell, but is in a location that is not native to the heterologous sequence. In some embodiments, a heterologous sequence is a non-host cell sequence, while in other embodiments, a heterologous sequence is a modified sequence, a sequence from a different host cell strain, or a homologous sequence from a different chromosomal location of the host cell.

As used herein, the terms "promoter", "promoter element", "promoter sequence" and "promoter region" refer to a DNA sequence which is capable of controlling the transcription of an oligonucleotide/polynucleotide sequence into mRNA when the promoter is placed at the 5' end of (i.e., precedes) an oligonucleotide/polynucleotide (coding) sequence. Thus, a promoter is typically located 5' (i.e., upstream) of an oligonucleotide sequence whose transcription into mRNA it controls, and provides a site for specific binding by RNA polymerase and for initiation of transcription.

The term "operably linked" refers to juxtaposition, wherein elements are in an arrangement allowing them to be functionally related. For example, a promoter is operably linked to a coding sequence of interest if it controls the transcription of the sequence.

As defined herein, the phrases "promoter", "promoter element", "promoter region" and/or "promoter sequence" refer to the minimal portion of the promoter nucleic acid sequence required to initiate transcription (i.e., comprising RNA polymerase binding sites). For example, a promoter of the instant disclosure comprises a −10 (consensus sequence) element and a −35 (consensus sequence) element, which are upstream (5') and relative to the +1 transcription start site of the gene or ORF to be transcribed. The core promoter −10 and −35 elements are generally referred to in the art as the "TATAAT" (Pribnow box) consensus region and the "TTGACA" consensus region, respectively. The spacing of the core promoter −10 and −35 sequence regions are generally separated (or spaced) by 15-20 intervening base pairs (nucleotides).

As further defined herein, a "promoter" sequence of the disclosure may additionally comprise nucleotides which are 5' (i.e., upstream) and natively associated with the promoter as found in nature (e.g., a natively associated UP element sequence which is 5' to the promoter sequence. For example, certain promoters set forth below in Tables 3-10 comprise (in addition to the −10/−35 minimal promoter region) natively associated UP element sequence. Thus, as defined herein, a "promoter" of the instant disclosure may comprise one or more nucleotides of a UP element sequence which are 5' to the promoter sequence as found in nature.

As used herein, an "upstream element", a "promoter upstream element", a "UP element" and a "UP sequence" are used interchangeably, and refer to an "A+T" rich nucleic acid sequence region located upstream (5') of the −35 core promoter region. The UP element may be further defined as a nucleic acid sequence region located upstream (5') of the −35 core promoter element which interacts directly with the C-terminal domain of the α-subunit of RNA polymerase. Set forth below in Table 2 are UP element sequences which are combined with one or more heterologous promoter sequences (set forth in Tables 3-10) to form one or more engineered hybrid "complete" promoters of the present invention.

As used herein a "ribosomal promoter" includes, for example, a ribosomal RNA promoter or a ribosomal protein promoter.

As used herein, a "complete promoter" or "hybrid promoter" refer to engineered promoters comprising at least a "UP element" and a "promoter", wherein the UP element is located upstream (5') of the promoter and wherein the promoter is located downstream (3') of the UP element and upstream (5') of the +1 transcription start site. The hybrid (complete) promoters of the instant disclosure are generally derived from *Bacillus subtilis* or *Bacillus licheniformis* ribosomal promoter sequences, wherein the UP element sequence and promoter sequence of the hybrid (complete) promoter are operably linked. For example, in certain embodiments, a hybrid (complete) promoter of the disclosure is engineered by combining a UP element sequence set forth in Table 2 with one or more heterologous promoter elements set forth in Tables 3-10. In certain other embodiments, these one or more heterologous promoter elements (sequences) include one or more nucleotides of a natively associated UP element sequence upstream (5') of the minimal promoter (−10/−35) element. For example, in certain embodiments, a hybrid (complete) promoter of the disclosure is engineered by combining a UP element sequence set forth in Table 2 with one or more heterologous promoter elements set forth in Tables 3-10 (wherein the one or more heterologous promoter elements optionally comprise one or more nucleotides of natively associated and operably linked UP element sequence.

As further defined herein, a "hybrid (complete) promoter" is an engineered promoter (i.e., comprising both a UP element sequence and a promoter element sequence), wherein the UP element and the promoter element of the hybrid promoter are constructed or derived from different nucleic sequences which are not found in nature operably linked or associated with each other. By way of example, a non-hybrid "complete promoter" is derived or constructed from a native (wild-type) *Bacillus* ribosomal promoter (e.g., a P1-rrnI (promoter element)) and a native (wild-type) UP element (e.g., a UP-rrnI element), wherein the promoter element (P1-rrnI) and the UP element (UP-rrnI) are operably linked as found in nature (i.e., the promoter element and the UP element are operably linked as isolated or identified from the genomic DNA source).

In contrast, the engineered "hybrid (complete) promoters" of the instant disclosure, are not found operably linked or associated with each other as found in nature (i.e., the promoter element and the UP element are not operably linked or associated as isolated or identified from the genomic DNA source). Thus, by way of example, an engineered "hybrid (complete) promoter" of the disclosure is derived or constructed from a native (wild-type) *Bacillus ribosomal* promoter (e.g., a P1-rrnI (promoter element)) and a native (wild-type) UP element (e.g., a UP-rrnO element), wherein the promoter element (P1-rrnI) and the UP element (UP-rrnO) are not operably linked as found in nature (i.e., the promoter element and the UP element are not operably linked as isolated or identified from the genomic DNA source). As used herein, the term "promoter activity" when made in reference to a nucleic acid sequence refers to the ability of the nucleic acid sequence to initiate transcription of an oligonucleotide sequence into mRNA.

The term "vector" is defined herein as a polynucleotide designed to carry nucleic acid sequences to be introduced into one or more cell types. Vectors include cloning vectors, expression vectors, shuttle vectors, plasmids, phage or virus particles, DNA constructs, cassettes and the like. Typical expression vectors, which also include plasmids, include regulatory sequences such as promoters, signal sequences, a gene of interest and transcription terminators.

The term "isolated" as defined herein, refers to a compound, protein, cell, nucleic acid sequence, or amino acid that is separated from at least one other compound, protein, cell, nucleic acid sequence, amino acid, or other biological substance with which it is ordinarily associated in its natural source.

As used herein the term "coding region" is defined herein as a nucleic acid sequence that is transcribed into mRNA which is translated into a polypeptide when placed under the control of appropriate control sequences including a promoter. A coding sequence may include cDNA, genomic DNA, synthetic DNA and recombinant DNA.

As used herein, a 5' untranslated region (hereinafter, "a 5' UTR") refers to a nucleic acid sequence which is 5' to (i.e., precedes) the coding sequence on a strand of mRNA. As used herein, a 3' untranslated region (hereinafter, "a 3' UTR") refers to a nucleic acid sequence which is 3' to (i.e., follows) the coding sequence on a strand of mRNA. Thus, untranslated regions (UTRs) of the transcribed mRNA are non-protein coding nucleic acid sequence.

As used herein, the term "wild-type" gene, gene product, or cell refers to a gene, gene product, or cell which has the characteristics of that gene, gene product, or cell when found in a naturally occurring source. A wild-type gene, gene product, or cell is that which is most frequently observed in a population and is thus designated the "native" or "wild-type" form. As used herein, the terms "wild-type sequence," and "wild-type gene" are used interchangeably and refer to a sequence that is native or naturally occurring in a host cell.

In contrast, the term "modified," "mutant," or "variant" gene, gene product, or cell refers to a gene, gene product, or cell which displays modifications in sequence and/or functional properties (i.e., altered characteristics) when compared to the wild-type form. Sequence modifications can occur by, for example, substitutions, insertions, deletions, or any other modification that results in an altered sequence or characteristic. It is noted that naturally-occurring mutants can be isolated; these are identified by the fact that they have altered characteristics when compared to the wild-type gene or gene product.

As used herein, the terms "modified sequence" and "modified genes" are used interchangeably and refer to a substitution, insertion, deletion, interruption, or any other modification of naturally occurring nucleic acid sequence. In some embodiments, the expression product of the modified sequence is a truncated protein (e.g., if the modification is a deletion or interruption of the sequence). In some embodiments, the truncated protein retains biological activity. In other embodiments, the expression product of the modified sequence is an elongated protein (e.g., if the modification is an insertion into the nucleic acid sequence). In other embodiments, an insertion results in the production of a truncated protein as the expression product (e.g., if the insertion results in the formation of a stop codon).

As used herein, an "incoming sequence" means a DNA sequence that is introduced into the host cell chromosome or genome. The sequence may encode one or more proteins of interest. The incoming sequence may comprise a promoter operably linked to a sequence encoding a protein of interest. In some embodiments, incoming sequences comprise sequence that is already present in the genome of the cell to be transformed, while in other embodiments, it is not already present in the genome of the cell to be transformed (i.e., in some embodiments, it is homologous, while in other embodiments, it is heterologous sequence).

In some embodiments, the incoming sequence encodes at least one homologous or heterologous protein, including, but not limited to a hormone, enzyme, growth factor, or cytokine. In certain embodiments, the incoming sequence encodes at least one enzyme including, but not limited to a acetyl esterases, aryl esterases, aminopeptidases, amylases, arabinases, arabinofuranosidases, carboxypeptidases, catalases, cellulases, chitinases, chymosin, cutinase, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, rhamno-galacturonases, ribonucleases, thaumatin, transferases, transport proteins, transglutaminases, xylanases, hexose oxidases, and combinations thereof.

In some embodiments, the incoming sequence encodes a functional wild-type gene or operon, a functional mutant gene or operon, or a non-functional gene or operon.

As used herein, the term "reporter gene" refers to a nucleotide sequence, which is capable of expression in cells and where expression of the reporter confers to cells containing the expressed gene, the ability to be easily detected and measured.

As used herein, the term "flanking sequence", refers to any sequence that is either upstream or downstream of the sequence being discussed (e.g., for sequences A B C, sequence B is flanked by the A and C sequences). In some embodiments, the incoming sequence is flanked by a homology box on each side.

As used herein, the term "homology box" refers to sequences that are homologous to another nucleic acid sequence. For example, a homology box can be homologous to a nucleic acid sequence in genomic DNA. In such instance, the homology box is useful for directing where in a new construct is integrated into the genomic DNA.

As used herein, the term "homologous recombination" refers to the exchange of DNA fragments between two DNA molecules or paired chromosomes (i.e., during crossing over) at the site of identical nucleotide sequences. In one embodiment, chromosomal integration is accomplished via homologous recombination.

The terms "transfection" and "transformation" as used herein both refer to methods for introducing DNA into cells.

As used herein, the terms "complementary" or "complementarity" are used in reference to "polynucleotides" and "oligonucleotides" (which are interchangeable terms that refer to a sequence of nucleotides) related by the base-pairing rules. For example, the sequence "5'-CAGT-3'", is complementary to the sequence "5'-ACTG-3". Complementarity can be "partial" or "total". "Partial" complementarity is where one or more nucleic acid bases is not matched according to the base pairing rules. "Total" or "complete" complementarity between nucleic acids is where each and every nucleic acid base is matched with another base under the base pairing rules.

As used herein, the term "chromosomal integration" refers to the process whereby the incoming sequence is introduced into the chromosome (i.e., genome) of a host cell.

As used herein, the term "selectable marker" refers to the use of any "marker" (i.e., indicator), which indicates the presence or absence of a protein or gene of interest. In some embodiments, the term encompasses genes which encode an enzymatic activity that confers the ability to grow in medium lacking what would otherwise be essential. In other embodiments, a selectable marker confers resistance to an antibiotic or drug upon the cell in which the selectable marker is expressed.

As used herein, the term "signal sequence" or "signal peptide" refers to a sequence of amino acids at the N-terminal portion of a protein, which facilitates the secretion of the mature form of the protein outside the cell. The "mature form" of the extracellular protein lacks the signal sequence which is cleaved off during the secretion process.

"Amplification" is generally defined herein as the production of additional copies of a nucleic acid sequence. Amplification of a nucleic acid can be performed by, for example, polymerase chain reaction or other technologies that are well known in the art. As used herein, the term "polymerase chain reaction" ("PCR") refers to the methods of U.S. Pat. Nos. 4,683,195, 4,683,202, and 4,965,188, all of which are hereby incorporated by reference, which describe a method for increasing the concentration of a segment of a target sequence in a DNA sample (e.g., genomic DNA) without cloning or purification.

In certain other embodiments, a nucleic acid (polynucleotide) sequence of the disclosure is amplified in vivo. In particular embodiments, a nucleic acid (polynucleotide) sequence comprising (i) a gene (or ORF) encoding a protein of interest and (ii) an antibiotic resistance marker are amplified in vivo.

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; or incorporation of $^{32}$P-labeled deoxynucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced. The primer is preferably single stranded for maximum efficiency in amplification, but may alternatively be double stranded.

As used herein, the term "probe" refers to an oligonucleotide, whether occurring naturally as in a purified restriction digest or produced synthetically, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule", so that it is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the terms "restriction endonucleases" and "restriction enzymes" refer to bacterial enzymes, each of which cut double- or single-stranded DNA at or near a specific nucleotide sequence.

As used herein, the phrase an "AmyL amylase" may be used interchangeably with "LAT amylase".

B. Ribosomal Promoters

Ribosomal RNA (rRNA) synthesis is the rate-limiting step in ribosome synthesis in *Escherichia coli* and *Bacillus subtilis*. The regulation of ribosomal RNA transcription from ribosomal RNA promoters has been studied previously (Samarrai et al., 2011; Natori et al., 2009; Turnbough, 2008; Krasny et al., 2008; Krasny and Gourse, 2004). Ribosomal RNA promoters are tightly regulated with nutritional conditions so that ribosomal RNA and ribosomes are not overproduced in times when translational requirements are lower.

In *E. coli*, there are seven rRNA (rrn) operons, each of which comprises two promoters designated P1 and P2. The core −10/−35 promoter region in the *E. coli* rrn P1 promoters are preceded by promoter upstream (UP) elements that increase promoter activity by up to 20-50 fold by binding RNA polymerase. *Bacillus subtilis*, contains 10 rRNA (rrn) operons (Krasny and Gourse, 2004), which are also preceded by promoter upstream (UP) elements that increase promoter activity.

The regulation of the genes that encode ribosomal proteins has been studied previously in *Escherichia coli* and *Bacillus subtilis* (Grundy and Henkin, 1991). In many cases, the ribosomal proteins have been found to act as an autogenous repressor, controlling the expression of the operon in which they are encoded.

The regulation of ribosomal RNA promoters has been studied for the production of native ribosomal RNAs, and more recently, the expression levels of nucleic acid sequences coding for heterologous proteins of interest when using ribosomal RNA (rRNA) promoters has been described (see, PCT Publication No. WO2013/086219).

As set forth herein, the present invention demonstrates that novel engineered ribosomal promoters, comprising a hybrid combination of *Bacillus* species promoter elements and UP elements, are unexpectedly effective at producing heterologous proteins of interest when expressed in a host microorganism. For example, as set forth in Example 2, the expression of the subtilisin protease BPN' (Y217L) from native (heterologous) promoters (e.g., PaprE, PssrA, Pscr, PspoVG), native (heterologous) ribosomal promoters (e.g., PrrnI-2) and engineered (heterologous) ribosomal promoters (e.g., hybrid promoter 1 and hybrid promoter 7) were tested in a *B. subtilis* host cell. The results (see, FIG. 3) demonstrate that the PssrA promoter, Pscr promoter, PrrnI-2 promoter, hybrid promoter 1 and hybrid promoter 7 provide higher protein (BPN') productivity than the PaprE promoter and the PspoVG promoter. In particular, as presented in FIG. 3, hybrid promoter 1 (SEQ ID NO: 65) and hybrid promoter 7 (SEQ ID NO: 71) clearly demonstrate the highest levels of subtilisin BPN' production under the conditions tested.

Figure 4:
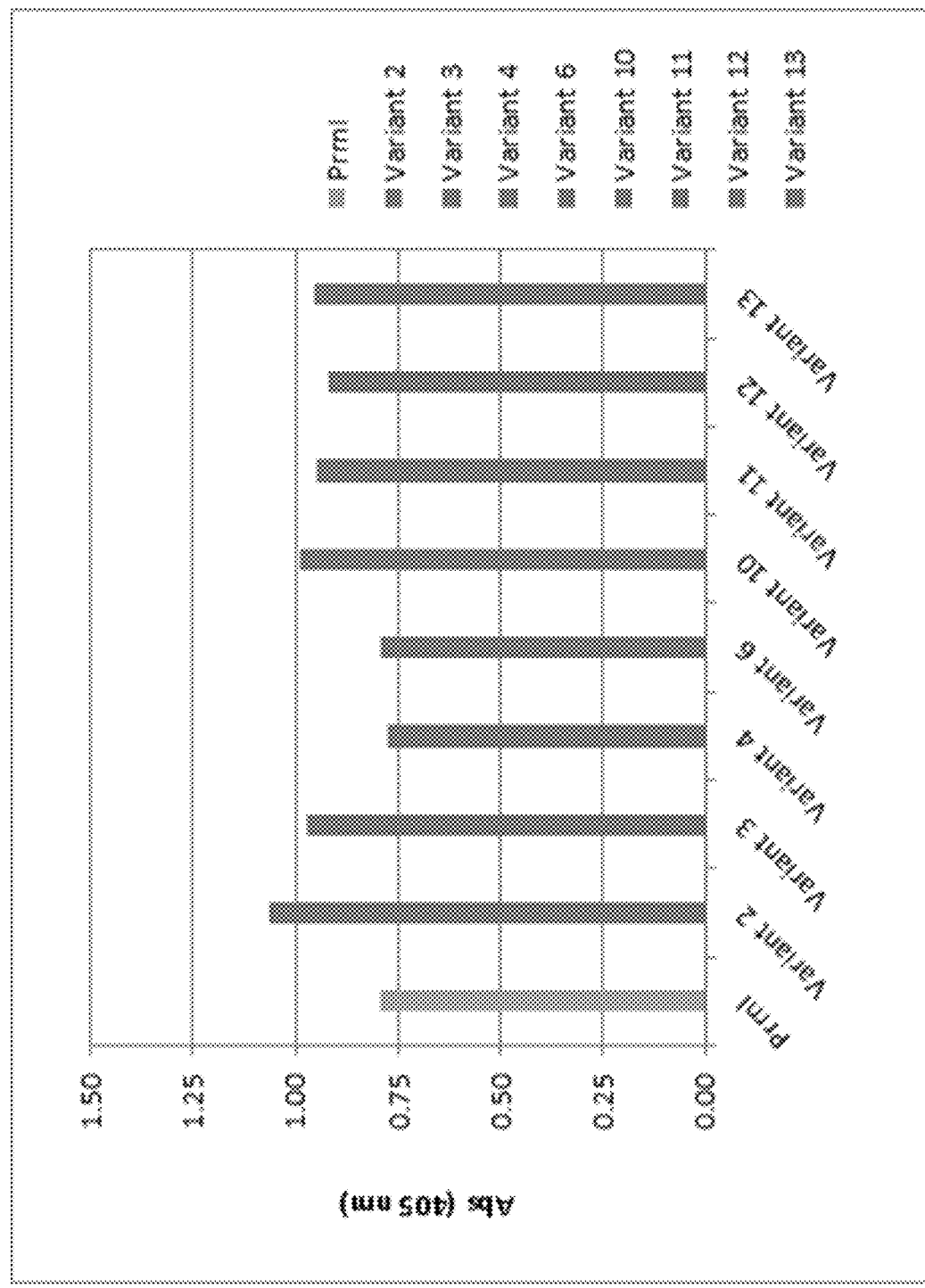
FIG. 4 shows the relative expression of *Cytophaga* sp variant amylase expressed in *B. licheniformis* using the following native (wild-type) and engineered (hybrid) promoters: PrrnI-2 (wild-type; SEQ ID NO: 15); Variant 2 (hybrid promoter 1; SEQ ID NO: 65); Variant 3 (hybrid promoter 23; SEQ ID NO: 96); Variant 4 (hybrid promoter 24; SEQ ID NO: 97); Variant 6 (hybrid promoter 20; SEQ ID NO: 93); Variant 10 (hybrid promoter 22; SEQ ID NO: 95); Variant 11 (hybrid promoter 19; SEQ ID NO: 92); Variant 12 (hybrid promoter 18; SEQ ID NO: 91) and Variant 13 (hybrid promoter 17; SEQ ID NO: 90).

Similarly, as set forth in Example 3, the expression of a *Cytophaga* sp amylase variant (SEQ ID NO:63) from the native (heterologous) promoter PrrnI-2 (SEQ ID NO: 15) and engineered (heterologous) variant PrrnI-2 promoters thereof (i.e., Variant 2 (hybrid promoter 1); Variant 3 (hybrid promoter 23); Variant 4 (hybrid promoter 24); Variant 6 (hybrid promoter 20); Variant 10 (hybrid promoter 22); Variant 11 (hybrid promoter 19); Variant 12 (hybrid promoter 18) and Variant 13 (hybrid promoter 17)) were tested in a *B. licheniformis* host cell. In particular, as presented in FIG. 4, the amylase expression/productivity from the engineered (variant) PrrnI-2 promoters, (i.e., FIG. 4; Variant 2, Variant 3, Variant 10, Variant 11, Variant 12 and Variant 13), resulted in increased production of the amylase protein when compared to the native (heterologous) PrrnI-2 promoter.

Furthermore, as set forth in Example 4, a series of native (wild-type) promoters from *B. subtilis* and *B. licheniformis* were evaluated for the expression of 3 different bacterial amylases in a *B. licheniformis* host. The following promoters for driving the expression of the amylase proteins were evaluated: PamyL promoter of the amyL *Bacillus licheniformis* native amylase gene (SEQ ID NO: 116); PrrnI-2 promoter of the *Bacillus subtilis* ribosomal RNA rrnI (SEQ ID NO: 15); *Bacillus licheniformis* PrrnI promoter (SEQ ID NO: 101); *Bacillus licheniformis* Prrn2 promoter (SEQ ID NO: 102); *Bacillus licheniformis* Prrn4 promoter (SEQ ID NO: 103); *Bacillus licheniformis* Prrn5 promoter (SEQ ID NO: 104) and *Bacillus licheniformis* Prrn6 promoter (SEQ ID NO: 105).

Figure 5:
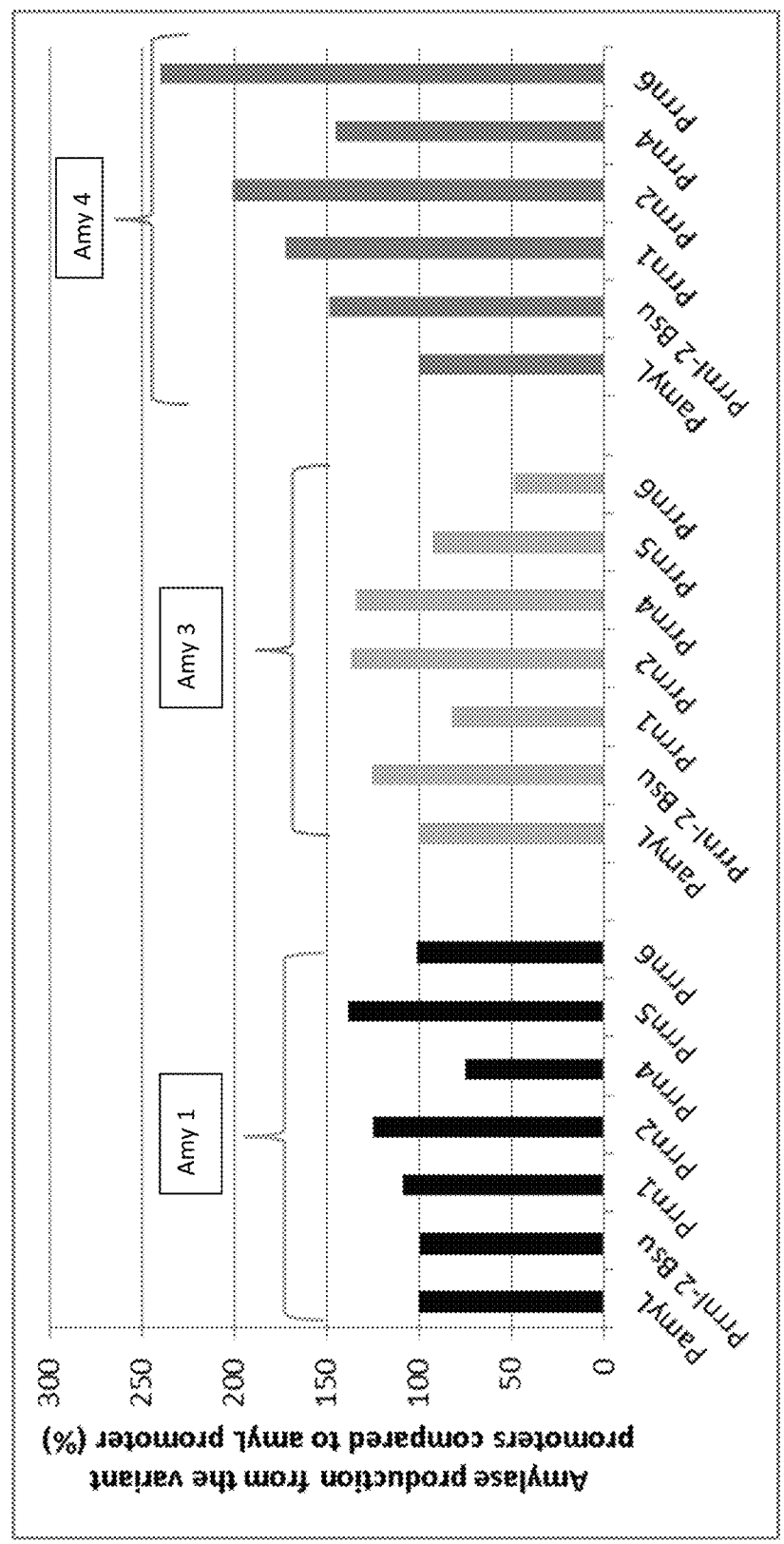
FIG. 5 shows the production of three bacterial amylases (i.e., Amy1, Amy3 and Amy4) in *B. licheniformis* using various native ribosomal promoters relative to the endogenous PamyL promoter of *B. licheniformis* amylase L. As depicted in FIG. 5, Amy 1 is a native *B. licheniformis* α-amaylase (SEQ ID NO: 43); Amy3 is *Geobacillus stearo-*

The native (wild-type) ribosomal promoter nucleic acid sequences set forth in SEQ ID NOS: 15, 101, 102, 103, 104 and 105 each comprise the native (−35/−10) ribosomal promoter and the native promoter upstream (UP) element nucleic acid sequences operably linked, as found or isolated in nature. The expression/productivity of polynucleotides encoding the 3 bacterial amylases (i.e., *B. lichenifomis* α-amylase L (SEQ ID NO: 43; Amyl); *Geobacillus stearothermophilus* α-amylase variant (SEQ ID NO: 64; Amy3) and *Cytophaga* sp amylase variant (SEQ ID NO:63; Amy4)), were operably linked (3') to the above-referenced promoters (i.e., promoters of SEQ ID NOs: 15 and 101-105). As presented in FIG. 5, the relative expression of the 3 bacterial amylases (i.e., Amy 1, Amy 3 and Amy 4) driven by the various native (wild-type) promoters (i.e., PamyL, PrrnI-2, Prrn1, Prrn2, Prrn4, Prrn5 and Prrn6) demonstrates that the use of these heterologous ribosomal promoters, instead of the endogenous native *B. licheniformis* amylase promoter (PamyL), provide increased protein expression/productivity in most instances.

Thus, in certain embodiments, the present disclosure is directed to engineered (modified) heterologous promoters for use in expressing a nucleic acid sequence (or ORF) encoding a protein of interest (POI). In certain embodiments, the engineered promoters comprise at least a promoter upstream (UP) element nucleic acid sequence operably linked to a promoter nucleic acid sequence, wherein the operably linked combination of the UP element and promoter element are referred to herein as a heterologous "complete promoters" or heterologous hybrid "complete promoters". More particularly, as defined above in section A, a heterologous hybrid "complete promoter" is an engineered promoter (i.e., comprising both a UP element sequence and a promoter element sequence), wherein the UP element and the promoter element of the heterologous hybrid "complete promoter" are constructed or derived from different nucleic acid sequences which are not found in nature (e.g., genomic/chromosomal DNA) operably linked or associated with each other.

Thus, in certain embodiments, a heterologous hybrid complete promoter of the present disclosure comprises a nucleic acid sequence set forth below in Table 1 as SEQ ID NOS: 65-97.

TABLE 1

Heterologous Hybrid (Complete) Promoters

| SEQ ID | Hybrid No. | Hybrid Promoter Nucleic Acid Sequence |
|---|---|---|
| 65 | 1 | GTCGCTGATAAACAGCTGACATCAATATCCTATTTTTTCAAAAAATATTTTAAAA GTTGTTGACTTAAAAGAAGCTAAATGTTATAGTAATAAA |
| 66 | 2 | GTCGCTGATAAACAGCTGACATCAATATCCTATTTTTTCAAAAAATATTTTAAAA AGTTGTTGACTTAAAAGAAGCTAAATGTTATAGTAATAAA |
| 67 | 3 | GTCGCTGATAAACAGCTGACATCAATATCCTATTTTTTCAAAAAATATTTTAAAA AGTTGTTGCAATTTTTAGGGGAAACAGATATACTTAAGTGT |
| 68 | 4 | GTCGCTGATAAACAGCTGACATCAATATCCTATTTTAAAAACTTTTTCAAAAAAG TGTTGTTGCAATTTTTAGGGGAAACAGATATACTTAAGTGT |
| 69 | 5 | GTCGCTGATAAACAGCTGACATCAATATCCTATTTTTTCAAAAAATATTTTAAAA AGTTGTTGAAAAGAGCCGTGATCATGTTATAATAAGACTA |
| 70 | 6 | AAAAATATTAAAAAGAAAAGCTTGACTTTGAAGAAGTGACATTGTATACT |
| 71 | 7 | GTCGCTGATAAACAGCTGACATCAATATCCTATTTTTTCAAAAAATATTTTAAAA GTTGTTGACTTAAAAGAAGCTAAATGTTATAGTAATAAAACAGAATAGTCTTTTA AGTAAGTCTACTCTGAATTTTTTTAAAAGGAGAGGGTAAAGAAAGCCGCCAGGA AAAACTTGTCTGAATAGTACGGTTGCAATTTTTAGGGGAAACAGATATACTTAA GTGT |
| 72 | 8 | AAAAAAAATGTGATATAAAAGTTGACTTTGAAGAAGTGACATTGTATACTAATA AAGTACAGAATAGTCTTTTAAGTAAGTCTACTCTGAATTTTTTTAAAAGGAGAGG GTAAAGAAAGCCGCCAGGAAAAAACTTGTCTGAATAGTACGGTTGCAATTTTTAG GGGAAACAGATATACT |

TABLE 1-continued

Heterologous Hybrid (Complete) Promoters

| SEQ ID | Hybrid No. | Hybrid Promoter Nucleic Acid Sequence |
|---|---|---|
| 73 | 9 | AACGTCGCTGATGAACAGCGTGAAACAAAACAGAAAAACAAAAAAGTTTTCCT<br>AAATCCTATTTTTTCAAAAAATATTTTAAAAAGGTGTTTACAAGATTTTAAAAAT<br>GTGTATAATAAGAAAAGTCGAATTGAAAAAGATTCGAAAAAACATTAAAAAAC<br>TTCTTGACTTCAACATCAAATGATAGTATGATAGTTAA |
| 74 | 10 | CTGCGCTTTTTGTGTCATAACCCTTTACAGTCATAAAAATTATGGTATAATCATT<br>TCTGTTGTCTTTTTAAAGACACAAGCATGACCATTATGACTAGTAAAAACTTTTT<br>CAAAAAAGTATAATTGACATGTATTGAATGATATAGAATAATTGGTTTATATTA |
| 75 | 11 | GTCGCTGATAAACAGCTGACATCAATGTTTTTTTATCCCAATATTACAAAAATAT<br>TTTTAATTATGCAGGAAAACAAAAAAAGTTGTTGACTTAAAAGAAGCTAAATGT<br>TATAGTAATAAA |
| 76 | 12 | TGTTTTTTTATCCCAATATTACAAAAATATTTTTAATTATGCAGGAAAACAAAAA<br>AAGTTGTTGACGACATCACGATTAAATGTTAAGATATTATAACAGAATAGTCTTT<br>TAAGTAAGTCTACTCTGAATTTTTTTAAAAGGAGAGGGTAAAGAAAGCCGCCAG<br>GAAAAACTTGTCTGAATAGTACGGTTGCAATTTTTAGGGGAAACAGATATACTT<br>AAGTGT |
| 77 | 13 | GTCGCTGATAAACAGCTGACATCAATATCCTATTTTTTCAAAAAATATTTTAAAA<br>AGTTGTTGACGACATCACGATTAAATGTTAAGATATTATAACAGAATAGTCTTTT<br>AAGTAAGTCTACTCTGAATTTTTTTAAAAGGAGAGGGTAAAGAAAGCCGCCAGG<br>AAAAACTTGTCTGAATAGTACGGTTGCAATTTTTAGGGGAAACAGATATACTTA<br>AGTGT |
| 78 | 14 | GTCGCTGATAAACAGCTGACATCAATGTTTTTTTATCCCAATATTACAAAAATAT<br>TTTTAATTATGCAGGAAAACAAAAAAAGTTATTGACAAATACGTGAGCTTGATG<br>TTATATTATTAAAACAGAATAGTCTTTTAAGTAAGTCTACTCTGAATTTTTTAAA<br>AGGAGAGGGTAAAGAAAGCCGCCAGGAAAAACTTGTCTGAATAGTACGGTTGC<br>AATTTTTAGGGGAAACAGATATACTTAAGTGT |
| 79 | 15 | GTCGCTGATAAACAGCTGACATCAATATCCTATTTTTTCAAAAAATATTTTAAAA<br>AGTTATTGACAAATACGTGAGCTTGATGTTATATTATTAAAACAGAATAGTCTTT<br>TAAGTAAGTCTACTCTGAATTTTTTTAAAAGGAGAGGGTAAAGAAAGCCGCCAG<br>GAAAAACTTGTCTGAATAGTACGGTTGCAATTTTTAGGGGAAACAGATATACTT<br>AAGTGT |
| 80 | 16 | GTCGCTGATAAACAGCTGACATCAATATCCTATTTTTTCAAAAAATATTTTAAAA<br>AGTTGTTGACTTAAAAGAAGCTAAATGTTATAGTAATAAAACAGAATAGTCTTTT<br>AAGTAAGTCTACTCTGAATTTTTTTAAAAGGAGAGGGTAAAGAGCTTTTCTTTTG<br>GAAGAAAATATAGGGAAAATGGTACTTGTTAAAAATTCGGAATATTTATACAAT<br>ATCATAT |
| 90 | 17 | GTCGCTGATAAACAGCTGACATCAATGTTTTTTTATCCCAATATTACAAAAATAT<br>TTTTAATTATGCAGGAAAACAAAAAAAGTTATTGACAAATACGTGAGCTTGATG<br>TTATATTATTAAAACAGAATAGTCTTTTAAGTAAGTCTACTCTGAATTTTTTTAAA<br>AGGAGAGGGTAAAGAAAGCCGCCAGGAAAAACTTGTCTGAATAGTACGGTTGC<br>AATTTTTAGGGGAAACAGATATACTTAAGTGT |
| 91 | 18 | GTCGCTGATAAACAGCTGACATCAATGTTTTTTTATCCCAATATTACAAAAATAT<br>TTTTAATTATGCAGGAAAACAAAAAAAGTTGTTGACGACATCACGATTAAATGT<br>TAAGATATTATAACAGAATAGTCTTTTAAGTAAGTCTACTCTGAATTTTTTTAAA<br>AGGAGAGGGTAAAGAAAGCCGCCAGGAAAAACTTGTCTGAATAGTACGGTTGC<br>AATTTTTAGGGGAAACAGATATACTTAAGTGT |
| 92 | 19 | GTCGCTGATAAACAGCTGACATCAATATCCTATTTTTTCAAAAAATATTTTAAAA<br>AGTTATTGACAAATACGTGAGCTTGATGTTATATTATTAAAACAGAATAGTCTTT<br>TAAGTAAGTCTACTCTGAATTTTTTTAAAAGGAGAGGGTAAAGAAAGCCGCCAG<br>GAAAAACTTGTCTGAATAGTACGGTTGCAATTTTTAGGGGAAACAGATATACTT<br>AAGTGT |
| 93 | 20 | GTCGCTGATAAACAGCTGACATCAATATCCTATTTTTTCAAAAAATATTTTAAAA<br>AGTTGTTGACTTAAAAGAAGCTAAATGTTATAGTAATAAAACAGAATAGTCTTTT<br>AAGTAAGTCTACTCTGAATTTTTTTAAAAGGAGAGGGTAAAGAAAGCCGCCAGG<br>AAAAACTTGTCTGAATAGTACGGTTGCAATTTTTAGGGGAAACAGATATACTTA<br>AGTGT |
| 94 | 21 | AGCTCGTCGCTGATAAACAGCTGACATCAATATCCTATTTTTTCAAAAAATATTT<br>TAAAAAGTTGTTGACTTAAAAGAAGCTAAATGTTATAGTAATAAAACAGAATAG<br>TCTTTTAAGTAAGTCTACTCTGAATTTTTTTAAAAGGAGAGGGTAAAGAGCTTTT<br>CTTTTGGAAGAAAATATAGGGAAAATGGTACTTGTTAAAAATTCGGAATATTTA<br>TACAATATCATAT |
| 95 | 22 | AGCTCGTCGCTGATAAACAGCTGACATCAATATCCTATTTTTTCAAAAAATATTT<br>TAAAAAGTTGTTGACTTAAAAGAAGCTAAATGTTATAGTAATAAAACAGAATAG |

TABLE 1-continued

Heterologous Hybrid (Complete) Promoters

| SEQ ID | Hybrid No. | Hybrid Promoter Nucleic Acid Sequence |
|---|---|---|
|  |  | TCTTTTAAGTAAGTCTACTCTGAATTTTTTAAAAGGAGAGGGTAAAGAGCTTTT CTTTTGGAAGAAAATATAGGGAAAATGGTACTTGTTAAAAATTCGGAATATTTA TACAATATCATAT |
| 96 | 23 | GTCGCTGATAAACAGCTGACATCAATATCCTATTTTTTCAAAAAATATTTTAAAA AGTTGTTGACTTAAAAGAAGCTAAATGTTATAGTAATAAAACAGAATAGTCTTTT AAGTAAGTCTACTCTGAATTTTTTTAAAAGGAGAGGGTAAAGA |
| 97 | 24 | GTCGCTGATAAACAGCTGACATCAATGTTTTTTTATCCCAATATTACAAAAATAT TTTTAATTATGCAGGAAAACAAAAAAAGTTGTTGACTTAAAAGAAGCTAAATGT TATAGTAATAAA |

In certain other embodiments, the present disclosure is directed to engineered (modified) heterologous hybrid complete promoters for use in expressing a nucleic acid sequence (or ORF) encoding a protein of interest (POI), wherein the heterologous hybrid complete promoters are constructed or derived by combining and operably linking a promoter UP element comprising a nucleic acid sequence set forth in Table 2 with: (1) a *B. subtilis* ribosomal RNA promoter element comprising a nucleic acid sequence set forth in Table 3, (2) a *B. subtilis* ribosomal protein promoter comprising a nucleic acid sequence set forth in Table 4, (3) a *B. subtilis* transfer message RNA (tmRNA) promoter comprising a nucleic acid sequence set forth in Table 5, (4) a *B. subtilis* small cytoplasmic RNA (scRNA) promoter comprising a nucleic acid sequence set forth in Table 6, (5) a *B. subtilis* protein promoter comprising a nucleic acid sequence set forth in Table 7, (6) a *B. licheniformis* ribosomal RNA promoter element comprising a nucleic acid sequence set forth in Table 8, (7) a *B. subtilis* Prrn Ribosomal RNA Promoter Consensus Sequence set forth in Table 9 and/or (8) a *B. licheniformis* Prrn Ribosomal RNA Promoter Consensus Sequence set forth in Table 10.

TABLE 2

*B. subtilis* and *B. licheniformis* Promoter UP Elements

| SEQ ID | UP Element Name | UP Element Nucleic Acid Sequence |
|---|---|---|
| 45 | rrnO | TAAAAACTTTTTCAAAAAGT |
| 46 | rrnA | AAAAGAAAATGCTAAAAAGTT |
| 47 | rrnJ | AAAAGAACTTCAAAAAAGTT |
| 48 | rrnI | TTAAATACTTTGAAAAAGTT |
| 49 | rrnE | CGAAAAAACATTAAAAAACTT |
| 50 | rrnD | GGAAAATAAATCAAAAAAACA |
| 51 | spoVG 5'-extended | ATTTTTTCAAAAAATATTTTAAAA |
| 52 | spoVG SHORT | AAAAATATTTTAAAA |
| 53 | spoVG 5' & 3' extended | ATTTTTTCAAAAAATATTTTAAAAACGAGC |
| 54 | spoVG 3'-extended | AAAAATATTTTAAAAACGAGC |
| 55 | spoVS SHORT | AAAAATATTAAAAAG |
| 56 | spoVS 5'-extended | TTATTTTATAAAAATATTAAAAAG |
| 57 | ftsA SHORT | AAAAAAAATGTGATA |
| 58 | ftsA 5'-extended | AAAAAAAATAAAAAAAATGTGATA |
| **59 | Consensus SHORT σH-dependent promoters | AAAAAWAWTDWRAWR |
| **60 | Consensus LONG σH-dependent promoters | WWWWWWWMWAAAAAWAWTDWRAWR |
| 61 | spoVG | CAAAAATATTTTAATTATGC |

**SEQ ID NO: 59 and SEQ ID NO: 60 are consensus sequences and are presented using IUPAC codes defined as: N = any nucleotide, R = A/G, Y = C/T, S = G/C, W = A/T, K = G/T, M = A/C, B = C/G/T, D = A/G/T, H = A/C/T and V = A/C/G. SEQ ID NO: 59 is the consensus nucleic acid sequence derived from the top three short *B. subtilis* σH-dependent promoter sequences and SEQ ID NO: 60 is the consensus nucleic acid sequence derived from the top three long *B. subtilis* σH-dependent promoter sequences.

TABLE 3

*B. subtilis* Ribosomal RNA Promoters

| SEQ ID | Promoter | Promoter Nucleic Acid Sequence |
|---|---|---|
| **1 | σA | TTGACANNNNNNNNNNNNNNNNNTATAAT |
| **2 | σH | RNAGGAWWWNNNNNNNNNNNNRNGAAT |
| 3 | P1 rrnA extended | ATATTATGTATTGACTTAGACAACTGAAGGTGTTATTCTAATATAC |
| 4 | P2 rrnA extended | TAAAAAGTTGTTGACAGTAGCGGCGGTAAATGTTATGATAATAAA |
| 5 | P1 rrnB | ATAGATTTTTTTAAAAAACTATTGCAATAAATAAATACAGGTGTTATATTAT TAAAC |
| 6 | P2 rrnB extended | AAAAAGTTGTTGACAAAAAGAAGCTGAATGTTATATTAGTA |
| 7 | P1 rrnD extended | AAAAAGGTGTTGACTCTGATTCTTGACCGTGTTATATTATTAAAC |
| 8 | P2 rrnD extended | AAAAAAACATTTGACAAAAGAAAGTCAAAATGTTATATTAATAAA |
| 9 | P1 rrnE | ATAAAAAAATACAGGAAAAGTGTTGACCAAATAAAACAGGCATGGTATATT ATTAAAC |
| 10 | P2 rrnE | AACAAAAAAGTTTTCCTAAGGTGTTTACAAGATTTTAAAAATGTGTATAATA AGAAAA |
| 11 | p3 rrnE | TCGAAAAAACATTAAAAAACTTCTTGACTCAACATCAAATGATAGTATGATA GTTAA |
| 12 | P1 rrnG | GTGTAATTTTTTAAAAAAGTTATTGACTTTGAAGAAGTGACATTGTATACTAA TAAAGTTGCTTTAA |
| 13 | P1 rrnH | AGTTTTTAAAAAAGGTTATTGACTTTGAAGAAGTGACATTGTATACTAATAAA GTTGCTTTA |
| 14 | P1 rrnI | CACATACAGCCTAAATTGGGTGTTGACCTTTTGATAATATCCGTGATATATTA TTATTCGTCGCTG |
| 15 | P2 rrnI | TTAAATACTTTGAAAAAAGTTGTTGACTTAAAAGAAGCTAAATGTTATAGTA ATAAAGCTGCTT |
| 16 | P1 rrnO extended | TGTCATAACCCTTTACAGTCATAAAAATTATGGTATAATCATTTCTG |
| 17 | P2 rrnO extended | CAAAAAAGTATTGACCTAGTTAACTAAAAATGTTACTATTAAGTAG |
| 18 | P rrnG extended | ACGCCGCCAAGCAATTGCACATTAGTGTAATTTTTTAAAAAAGTTATTGACTT TGAAGAAGTGACATTGTATACTAATAAAGTTGCTTTAACAAAGCGGACAAAC AAAATGATCTTTGAAAACTAAACAAGACAAAACGTACCTGTTAATTCAGTTT TTAAAAATCGCACAGCGATGTGCGTAGTCAGTCAAACTAC |
| 19 | PrrnW extended | AAAAGTTTTTAAAAAAGTTGTTGACTTTGAAGAAGTGACGTTGTATACTAATA AAGTTGCTTTAACAAAGCGGACAAACAAAATGATCTTTGAAAACTAAACAAG ACAAAACGTACCTGTTAATTCAGTTTTTAAAAATCGCACAGCGATGTGCGTA GTCAGTCAAACTAC |
| 20 | PrrnH extended | AGTTTTTAAAAAAGGTTATTGACTTTGAAGAAGTGACATTGTATACTAATAAA GTTGCTTTAACAAAGCGGACAAACAAAATGATCTTTGAAAACTAAACAAGAC AAAACGTACCTGTTAATTCAGTTTTTAAAAATCGC ACAGCGATGTGCGTAGTCAGTCAAACTAC |
| 85 | PrrnO_P1 | GCGCTTTTTTGTGTCATAACCCTTTACAGTCATAAAAATTATGGTATAATCAT TTCTG |
| 89 | PrrnO_P2 | TAAAAACTTTTTCAAAAAGTATTGACCTAGTTAACTAAAAATGTTACTATTA AGTA |
| 142 | PrrnA_P1 | ATCATTTAATTGATATTATGTATTGACTTAGACAACTGAAGGTGTTATTCTAA TATA |
| 143 | PrrnA_P2 | AAAAGAAAATGCTAAAAGTTGTTGACAGTAGCGGCGGTAAATGTTATGATA ATAAAG |

TABLE 3-continued

*B. subtilis* Ribosomal RNA Promoters

| SEQ ID | Promoter | Promoter Nucleic Acid Sequence |
|---|---|---|
| 144 | PrrnJ_P1 | TAGTATTTCTTCAAAAAAACTATTGCACTATTATTTACTAGGTGGTATATTATT ATTCG |
| 145 | PrrnJ_P2 | AAAAGAACTTCAAAAAAGTTATTGACTTCACTGAGTCAACGAGTTATAATA ATAAAG |
| 146 | PrrnI_P2 | TTAAATACTTTGAAAAAAGTTGTTGACTTAAAAGAAGCTAAATGTTATAGTA ATAAAG |
| 147 | PrrnE_P2 | ACAAAAAAGTTTTCCTAAGGTGTTTACAAGATTTTAAAAATGTGTATAATAA GAAAA |
| 148 | PrrnE_P3 | CGAAAAACATTAAAAAACTTCTTGACTTCAACATCAAATGATAGTATGATA GTTAAG |
| 149 | PrrnD_P1 | GGATATTCTTTTAAAAAAGGTGTTGACTCTGATTCTTGACCGTGTTATATTATT AAA |
| 150 | PrrnD_P2 | GGAAAATAAATCAAAAAAACATTTGACAAAAGAAAGTCAAAATGTTATATTA ATAAAG |
| 151 | PrrnG_P1 | GTGTAATTTTTAAAAAAGTTATTGACTTTGAAGAAGTGACATTGTATACTAA TAAAG |
| 152 | PrrnW_P1 | CCAAAAGTTTTTAAAAAAGTTGTTGACTTTGAAGAAGTGACGTTGTATACTAA TAAAG |
| **128 | PrrnO-P1 consensus | TTTACNNNNNNNNNNNNNNNNNNNNTATAAT |
| **129 | PrrnO-P2 consensus | TTGACNNNNNNNNNNNNNNNNNNNNTACTAT |
| **130 | PrrnA-P1 consensus | TTGACNNNNNNNNNNNNNNNNNNNNTATTCT |
| **131 | PrrnA-P2 consensus | TTGACNNNNNNNNNNNNNNNNNNNNTATGAT |
| **132 | PrrnJ-P1 consensus | TTGCANNNNNNNNNNNNNNNNNNNNTATATT |
| **133 | PrrnJ-P2 consensus | TTGACNNNNNNNNNNNNNNNNNNNNTATAAT |
| **134 | PrrnI consensus | TTGACNNNNNNNNNNNNNNNNNNNNTATAGT |
| **135 | PrrnE-P2 consensus | TTTACNNNNNNNNNNNNNNNNNNNNTATAAT |
| **136 | PrrnE-P3 consensus | TTGACNNNNNNNNNNNNNNNNNNNNTATGAT |
| **137 | PrrnD-P1 consensus | TTGACNNNNNNNNNNNNNNNNNNNNTATATT |
| **138 | PrrnD-P2 consensus | TTGACNNNNNNNNNNNNNNNNNNNNTATATT |
| **139 | PrrnG-P1 consensus | TTGACNNNNNNNNNNNNNNNNNNNNTATACT |
| **140 | PrrnW-P1 consensus | TTGACNNNNNNNNNNNNNNNNNNNNTATACT |

**SEQ ID NO: 1, SEQ ID NO: 2 and SEQ ID NOs: 128-140 are consensus sequences and are presented using IUPAC codes defined as: N = any nucleotide, R = A/G, Y = C/T, S = G/C, W = A/T, K = G/T, M = A/C, B = C/G/T, D = A/G/T, H = A/C/T and V = A/C/G.

TABLE 4

B. subtilis Ribosomal Protein Promoters

| SEQ ID | Promoter | Promoter Nucleic Acid Sequence |
|---|---|---|
| 21 | P1 + P2 rpsU | TTTCGAAGCATGTTCATGCCTGCGAGAAAGAATAATATAAGAGCAGTAAAGC TAATCAGAATTAACATCCTATTCACCAACCCCTTTCTTTCATTATATAGACAG GCAGTCGCACTCATGACGGAAAAGTGAACTCACTTAGTTGACCTGACTGATG GCTTATATTATAATGTCAAAGTACATGTTTATATGTGTAACTTAAAGGTAGTC GATTGGTGTATTCGGAGGGAGGGAAAGAGA |
| 22 | P1 + P2 rpsO | CGAGCGGAAATTCAATGGCATCAAAGAATTAACTGAGCAAATTGAGAAAGA TAAGCAGGAAGCCATCCGTTATTTCAGCAATTTGCGGAAATAACTTGCAACG CACGCAAATTTTATTCTAAAATATTTGCATATAGGCACGATTTTTAGTATGAT AGTTTTCGTAGTCTTAAAACCATTGCTTGGCAATCCGAAGTCACCGACGGTTG CTAGGTAACTGGGGCTAAATATGATTTGGAGGTGAAACAGG |
| 23 | P rpsD | GTTTTTATCACCTAAAAGTTTACCACTAATTTTTGTTTATTATATCATAAACGG TGAAGCAATAATGGAGGAATGGTTGACTTCAAAACAAATAAATTATATAATG ACCTTT |
| 24 | P1 + P2 rpsJ | GTACCGTGTGTTTTCATTTCAGGGAAACATGACTTAATTGTTCCTGCAGAAAT ATCGAAACAGTATTATCAAGAACTTGAGGCACCTGAAAAGCGCTGGTTTCAA TTTGAGAATTCAGCTCACACCCCGCATATTGAGGAGCCATCATTATTCGCGAA CACATTAAGTCGGCATGCACGCAACCATTTATGATAGATCCTTGATAAATAA GAAAAACCCCTGTATAATAAAAAAAGTGTGCAAATGATGCATATTTTAAATA AGTCTTGCAACATGCGCCTATTTTCTGTATAATGGTGTATA |

TABLE 5

B. subtilis Transfer Message RNA (tmRNA) Promoters

| SEQ ID | Promoter | Promoter Nucleic Acid Sequence |
|---|---|---|
| 25 | PssrA | TAAAGGCATAGTGCTTGATTCGAAAATCAGGCCTGTGCTATACTGTGTTCACG ATCAGATCACGACGCCATTCATTTGAAGGATTTGACAATTGAAAAGAGCCGT GATCATGTTATAATAAGACTA |
| **33 | PssrA Consensus | ATTGAAANNNNNNNNNNNNNNNNNNNTATAAT |

TABLE 6

B. subtilis Small Cytoplasmic RNA (scRNA) Promoters

| SEQ ID | Promoter | Promoter Nucleic Acid Sequence |
|---|---|---|
| 26 | Pscr | AAGCCGCCAGGAAAAACTTGTCTGAATAGTACGGTTGCAATTTTTAGGGGAA ACAGATATACTTAAGTGT |
| **37 | Pscr Consensus | GTTGCAANNNNNNNNNNNNNNNNNNNNTATACT |

TABLE 7

B. subtilis Protein Promoters

| SEQ ID | Promoter | Promoter Nucleic Acid Sequence |
|---|---|---|
| 29 | Pvpr | AGCTGAAAGAATTGAAATGAAATTGGAGAACCGCTTTGAAAACTTTATACA CAAGTTATCCCAAAGATAAGAACAACTTAATCACAAGAGATATCCACATGTC CACAAACTCTATCTATATTTTGTATACGAACGTATATTCCTAACTATATATAT ACACAGGTTTATTCACTTATACACAGGGTTCTGTGTATAACTCCTTCGTTATA CACAAACAAAATCCAATAAATGGTCCAAATGACACAAGGATTTTTTTGAATT TTCAAGAAATATATACTAGATCTTTCACATTTTTTCTAAATACAAAGGGGGAA ACACA |

TABLE 7-continued

*B. subtilis* Protein Promoters

| SEQ ID | Promoter | Promoter Nucleic Acid Sequence |
|---|---|---|
| **34 | Pvpr Consensus | ATCCACNNNNNNNNNNNNNNNNNNTATATT |
| 30 | Pmpr | GTTGAAACGGCAAGAGAGAATGCAAAGAAAGCGTTGGACCAGCTAATTTTA AAATAGAGTTTGAACAGGTCTTGTCATGGGACAAGGCCTGTTTTTTTCTTTCT CCGTAAAAGTTTTATCATAAGAATCAGAAACCTGATTATAATGTAAAAGTCTT CCATCGATACGGGTGGTTGACACTAAAGGAGGGAGATGACAAA |
| **35 | Pmpr Consensus | TTTATCANNNNNNNNNNNNNNNNNNNNTATAAT |
| 31 | Pbpr | TAAAGGACAAAATCGTTTTCGATTTTGTCCTTTTTTGTTTTTCTCTTCACACTT TCCTTCTTATAAAGTCTTTTTCCCTATTGCTTCCTTCGCTTAGTAACAAAACAG ATAATTAGACCCATTTATTTTTGTGACATTTTTATCATTTTCATATATATGGAA ATTGAATGACATGAAACGACAATATCTGTAATTCAGATTGTCTACAGTTAATA TACAGCGATGTTCTGACAAACCATTCATTATTAAAAGGAGGGACGACACTTT TTTTAAAAAGCATGTTGAAAAAGGGGGATGAAA |
| **36 | Pbpr Consensus | ACAATANNNNNNNNNNNNNNNNNNNNTACAGT |
| 28 | PaprE | CATTTTCTTCTGCTATCAAAATAACAGACTCGTGATTTTCCAAACGAGCTTTC AAAAAAGCCTCTGCCCCTTGCAAATCGGATGCCTGTCTATAAAATTCCCGATA TTGGTTAAACAGCGGCGCAATGGCGGCCGCATCTGATGTCTTTGCTTGGCGA ATGTTCATCTTATTCTTCCTCCCTCTCAATAATTTTTTCATTCTATCCCTTTTC TGTAAAGTTTATTTTTCAGAATACTTTTATCATCATGCTTTGAAAAAATATCA CGATAATATCCATTGTTCTCACGGAAGCACACGCAGGTCATTTGAACGAATTT TTTCGACAGGAATTTGCCGGGACTCAGGAGCATTTAACCTAAAAAAGCATGA CATTTCAGCATAATGAACATTTACTCATGTCTATTTTCGTTCTTTTCTGTATGA AAATAGTTATTTCGAGTCTCTACGGAAATAGCGAGAGATGATATACCTAAAT AGAGATAAAATCATCTCAAAAAAATGGGTCTACTAAAATATTATTCCATCTA TTACAATAAATTC |
| **38 | PaprE Consensus | GTCTACTNNNNNNNNNNNNNNNNNNNNTACAAT |
| 32 | PispA | CTATTATAACTTGACTTACAGTTGAATCCCAGTCATACATGTTGAAGCCATCC AATATTTTGAAGATTACTAATTCTTTGGTGTGTATCCTATTTTTTCAAAATGCT TCAAATGGCTCTGTCCGAGCGCTTGCTTTTTTCATATAATATGAGGCAACACC CTTGAATCCACTTGCAAGCATAAAAAAGGAGGGCTTTTTT |
| **39 | PispA Consensus | CTGTCCGNNNNNNNNNNNNNNNNNNNNTATAAT |
| 27 | PspoVG σH-dependent | TAAGAAAAGTGATTCTGGGAGAGCCGGGATCACTTTTTTATTTACCTTATGCC CGAAATGAAAGCTTTATGACCTAATTGTGTAACTATATCCTATTTTTTCAAAA AATATTTTAAAAACGAGCAGGATTTCAGAAAAAATCGTGGAATTGATACAC |
| 117 | PftsA (σH) | AAAAAAAATGTGATATAAAAGAGGATATACATAGGATATAACGAATATTTTC A |
| 141 | PspoVS | TTATTTTATAAAAATATTAAAAAGAAAAGCAGGAATATAGCAACTCCTTAGT GAATATAGTAAA |

**SEQ ID NOS: 33-39, are consensus sequences and are presented using IUPAC codes defined as: N = any nucleotide, R = A/G, Y = C/T, S = G/C, W = A/T, K = G/T, M = A/C, B = C/G/T, D = A/G/T, H = A/C/T and V = A/C/G.

TABLE 8

*B. licheniformis* Ribosomal RNA Promoters

| SEQ ID | Promoter | Promoter Nucleic Acid Sequence |
|---|---|---|
| 101 | Prrn1 | TCGCTTATAAAAGCAACAACAAAAACTTTTTCAAAAAAGTATTGACCGCTT GTCTTATAAATGTTATATTTAAGTGTCGCTTATAAAAGCAACAACAAAAACTT TTTTTAAAAAGTATTGACCGCTTGTCTTATAAATGTTATATTTAAGTG |
| 102 | Prrn2 | TCGCTAATGACGAATAATTTTTTGAAAAAAGTTGTTGACGACATCACGATTAA ATGTTAAGATATTATATCGCTAATGACGAATAATTTTTTTGAAAAAAGTTGT TGACGACATCACGATTAAATGTTAAGATATTATAG |

TABLE 8-continued

B. licheniformis Ribosomal RNA Promoters

| SEQ ID | Promoter | Promoter Nucleic Acid Sequence |
|---|---|---|
| 103 | Prrn4 | TCGCTGTTAGCGGAACGGTTTTTGAACAGAAAGCAGCAGCGACGAAAAATCA AAAAAACATTTGACACTTCTCGTTGAAAATGTTATACTAATAAATCGCTGTTA GCGGAACGGTTTTTGAACAGAAAGCAGCAGCGACGAAAAATCAAAAAAACA TTTGACACTTCTCGTTGAAAATGTTATACTAATAAAG |
| 104 | Prrn5 | TTGCCGCAAAACGGCGGCGAAAGAAAAAAAGAACTTCAAAAAAAGTTCTTG ACTTAATATCTGAGATTGGATATAATATAAAATTGCCGCAAAACGGCGGCGA AAGAAAAAAAGAACTTCAAAAAAAGTTCTTGACTTAATATCTGAGATTGGAT ATAATATAAAAG |
| 105 | Prrn6 | TCGCTGATAAACAGCTGACATGAAAAAGCTCCAAAAAATAATTTTGAGAAAA GTTATTGACAAATACGTGAGCTTGATGTTATATTATTAAATCGCTGATAAACA GCTGACATGAAAAAGCTCCAAAAAATAATTTTGAGAAAAGTTATTGACAAAT ATGTGAGCTTGATGTTATATTATTAAAG |
| 106 | P1-rrn1 | AAAAACTTTTTTTAAAAAAGTATTGACCGCTTGTCTTATAAATGTTATATTTA AGTG |
| 107 | P1-rrn2 | TTTATCGCAATATAATTTTTTGTTGACAAATATATTTAAAGGTGTTAAATTAA TATTTG |
| 108 | P2-rrn2 | TAATTTTTTTGAAAAAAAGTTGTTGACGACATCACGATTAAATGTTAAGATAT TATA |
| 109 | P1-rrn3 | CAGAAAAACTTCAAAAAACTTCTTGACTTTAACTGATATTCATAGTATTATAG TTAAGATTCAATCTTTCAAATATAATCTTTTCATCAGGAACATAATGTGCTAT AATTTCTCTTGG |
| 110 | P1-rrn4 | GGATATTTTATTAAAAAAAGTGTTGACACTAATTTATAACGGTGATATATTAT TAAGCG |
| 111 | P2-rrn4 | CGACGAAAAATCAAAAAAACATTTGACACTTCTCGTTGAAAATGTTATACTA ATAAAG |
| 112 | P1-rrn5 | TAAATTTTTTCTCAAAAAGTATTGCACAATCATAAATACGGTGGTATATTAT TATTCG |
| 113 | P2-rrn5 | AAAAGAACTTCAAAAAAAGTTCTTGACTTAATATCTGAGATTGGATATAATA TAAAAG |
| 114 | P1-rrn6 | AAGAAAAAAATTAAAAAGAGGGTTGACCGGAATTAAATAAACATGTTATATT GTTATTCG |
| 115 | P2-rrn6 | AAAATAATTTTGAGAAAAGTTATTGACAAATATGTGAGCTTGATGTTATATTA TTAAAG |
| 116 | PamyL | GCTTTTCTTTTGGAAGAAAATATAGGGAAAATGGTACTTGTTAAAAATTCGG AATATTTATACAATATCATAT |
| **118 | Prrn1-P1 Consensus | TTGACNNNNNNNNNNNNNNNNNNNNNTATATTTTTTCANNNNNNNNNNNNN NNNTATAAT |
| **119 | Prrn2-P1 consensus | TTGACNNNNNNNNNNNNNNNNNNNNNTAAATTTTGACANNNNNNNNNNNNN NNNTAAATT |
| **120 | Prrn2-P2 consensus | TTGACGNNNNNNNNNNNNNNNNNNNNTAAGAT |
| **121 | Prrn3-P2 consensus | TTGACNNNNNNNNNNNNNNNNNNNNTATATAT |
| **122 | Prrn4-P1 consensus | TTGACNNNNNNNNNNNNNNNNNNNNTATATTTTGACANNNNNNNNNNNNNN NNNTATATT |
| **123 | Prrn4-P2 consensus | TTGACNNNNNNNNNNNNNNNNNNNNTATACTTTGACANNNNNNNNNNNNNN NNNTATACT |
| **124 | Prrn5-P1 consensus | TTGCANNNNNNNNNNNNNNNNNNNNTATATTTTGCACNNNNNNNNNNNNNN NNNTATATT |
| **125 | Prrn5-P2 consensus | TTGACTNNNNNNNNNNNNNNNNNNNNTATAAT |
| **126 | Prrn6-P1 consensus | TTGACNNNNNNNNNNNNNNNNNNNNTATATTTTGACCNNNNNNNNNNNNNN NNNTTATAT |

TABLE 8-continued

B. licheniformis Ribosomal RNA Promoters

| SEQ ID | Promoter | Promoter Nucleic Acid Sequence |
|---|---|---|
| **127 | Prrn6-P2 consensus | TTGACNNNNNNNNNNNNNNNNNNNNNNTATATTTTGACANNNNNNNNNNNNNNN NNNTTATAT |

**SEQ ID NOS: 118-127 are consensus sequences and are presented using IUPAC codes defined as: N = any nucleotide, R = A/G, Y = C/T, S = G/C, W = A/T, K = G/T, M = A/C, B = C/G/T, D = A/G/T, H = A/C/T and V = A/C/G.

TABLE 9

B. subtilis Prrn Ribosomal RNA Promoter Consensus Sequence

| SEQ ID | Promoter | Promoter Nucleic Acid Sequence |
|---|---|---|
| **153 | Prrn Consensus | DNRWDWWWWTTYWAAAAARKTRTTGACWDWRWWRWNDVWAVRTKKTA TDHTAATAN-WR |

**SEQ ID NO: 153 is a consensus sequences and is presented using IUPAC codes defined as: N = any nucleotide, R = A/G, Y = C/T, S = G/C, W = A/T, K = G/T, M = A/C, B = C/G/T, D = A/G/T, H = A/C/T and V = A/C/G.

25

TABLE 10

B. licheniformis Prrn Ribosomal RNA Promoter Consensus Sequence

| SEQ ID | Promoter | Promoter Nucleic Acid Sequence |
|---|---|---|
| **154 | Prrn Consensus | HRRWWWWWWWYHWAAAAARKTVTTGACHNHWWHWNWDWWHVRTGDT ATAWTAWTAWNHG |

**SEQ ID NO: 154 is a consensus sequences and is presented using IUPAC codes defined as: N = any nucleotide, R = A/G, Y = C/T, S = G/C, W = A/T, K = G/T, M = A/C, B = C/G/T, D = A/G/T, H = A/C/T and V = A/C/G.

Thus, in certain embodiments, the disclosure provides engineered heterologous hybrid complete promoters for use in expressing a nucleic acid sequence encoding a protein of interest (POI), wherein the hybrid promoter comprises at least one UP element (Table 2) operably linked to at least one promoter element (Tables 3-10). For example, in certain embodiments, an engineered heterologous hybrid complete promoter comprises the following generic formula:

5'-UP-1$^{st}$Pro-ORF-3';

wherein UP is a nucleic acid comprising a promoter upstream element, 1$^{st}$Pro is nucleic acid comprising at least a −35/−10 core promoter sequence and ORF is a nucleic acid sequence encoding a POI.

In other embodiments, the disclosure is directed to engineered heterologous hybrid complete promoters for use in expressing a nucleic acid sequence (or ORF) encoding a protein of interest (POI), wherein the hybrid promoter comprises at least one UP element (Table 2) operably linked to at least two promoter elements (Tables 3-10). For example, in certain embodiments, an engineered heterologous hybrid complete promoter comprises the following generic formula:

5'-UP-1$^{st}$Pro-2$^{nd}$Pro-ORF-3';

wherein UP is a nucleic acid comprising a promoter upstream element, 1$^{st}$Pro, and 2$^{nd}$Pro are the same or different nucleic acids comprising at least a −35/−10 core promoter sequence and ORF is a nucleic acid encoding a POI.

In other embodiments, the disclosure is directed to engineered heterologous hybrid complete promoters for use in expressing a nucleic acid sequence (or ORF) encoding a protein of interest (POI), wherein the hybrid promoter comprises at least one UP element (Table 2) operably linked to at least one or two promoter elements (Tables 3-10). For example, in certain embodiments, an engineered heterologous hybrid complete promoter comprises the following generic formulae:

5'-UP-1$^{st}$Pro-UTR-ORF-3';

5'-UP-1$^{st}$Pro-2$^{nd}$Pro-UTR-ORF-3';

5'-UP-1$^{st}$Pro-UTR-2$^{nd}$Pro-UTR-ORF-3';

wherein UP is a nucleic acid comprising a promoter upstream element, 1$^{st}$Pro and 2$^{nd}$Pro are the same or different nucleic acids comprising at least a −35/−10 core promoter sequence, UTR is a nucleic acid comprising a 5' untranslated region and ORF is a nucleic acid encoding POI.

The unexpectedly high protein productivity levels obtained via the expression of nucleic acid sequences encoding heterologous POIs when using the engineered promoters of the instant disclosure have several benefits. For example, expressing a coding sequence of interest (e.g., an ORF of interest encoding a POI) with an engineered heterologous hybrid complete promoter of the disclosure provides increased expression of the ORF coding sequence and/or increased POI produced, when compared to expression or protein productivity of the same ORF being expressed from its native promoter. In particular embodiments, the engineered promoters of the instant disclosure provide for increased levels of mRNA expression, which is particularly useful for unstable transcripts.

In another embodiment, expressing a coding sequence of interest with an engineered promoter allows for increased level of expression of a coding sequence of interest, without amplification of an expression construct comprising the engineered promoter. When using other expression constructs in the art, in order to achieve high expression levels of a coding sequence of interest, amplification of the expression construct is often required. The expression levels achieved with the engineered promoters described herein, however, are high enough that amplification of the expression construct is generally not necessary. Instead, high expression levels may be achieved with a single integrant of the expression construct comprising the engineered promoter, which provides several benefits. First, host cells are typically more stable because they do not undergo the loss of the amplified expression construct. Also, if an expression construct does not need to be amplified, host cell construction is more efficient, thus saving time, money and materials.

In certain other embodiments, the nucleotide located at the +1 transcriptional start site of an engineered promoter described herein is modified from a guanine to adenine. For example, certain embodiments of the invention contemplate that the modification of the +1 transcriptional start site (e.g., an A to G substitution at +1) site allows consistent production from a promoter described herein, and therefore, results in better overall productivity from the promoter (see, e.g., PCT International Publication No. WO2013/086219).

In certain embodiments, an engineered heterologous hybrid complete promoter of the present disclosure comprises a nucleic acid sequence set forth in SEQ ID NOS: 65-97, or a subsequence thereof. The subsequence will retain promoter activity and comprise at least about 10 nucleotides, at least about 20 nucleotides; at least about 30 nucleotides; at least about 40 nucleotides; at least about 50 nucleotides; at least about 60 nucleotides; at least about 70 nucleotides; at least about 80 nucleotides; at least about 90 nucleotides or at least about 100 nucleotides. The subsequence of any one of SEQ ID NOs: 65-97 should minimally comprise the −35 and −10 consensus regions (i.e., the core promoter element) and the UP element.

In certain other embodiments, an engineered heterologous hybrid complete promoter of the present disclosure is constructed or derived from at least one UP element set forth in Table 2, which is combined and operably linked with a promoter element set forth in any one of Tables 3-10, or subsequences thereof. The subsequence will retain promoter activity and comprise at least about 10 nucleotides, at least about 20 nucleotides; at least about 30 nucleotides; at least about 40 nucleotides; at least about 50 nucleotides; at least about 60 nucleotides; at least about 70 nucleotides; at least about 80 nucleotides; at least about 90 nucleotides or at least about 100 nucleotides. The subsequence of any one of the promoter element nucleic acid sequences set forth Tables 3-10 in should minimally comprise the −35 and −10 consensus regions (i.e., the core promoter element).

In other embodiments, the engineered promoters of the present disclosure comprise nucleic acid sequences (or subsequences thereof) which hybridize with any one of the nucleic acid sequences set forth in Tables 1-10, which will have at least about 20%, at least about 30%, at least about 40%, least about 50%, at least about 60%, at least about 80%, and at least about 100% of the promoter activity of its corresponding parent promoter nucleic acid sequence. In some embodiments, the promoter activity will be greater, for example more than about 100%, more than about 150%, more than about 200% and more than about 250%. In some embodiments, the promoter will include a nucleic acid sequence that hybridizes under medium, high or very high stringency conditions.

In a particular embodiment, hybridization is used to analyze whether a given nucleic acid fragment corresponds to a promoter nucleic acid sequence described herein and thus falls within the scope of the present invention (see, Sambrook et al., 1989, which describes general hybridization methods).

"Hybridization conditions" refer to the degree of "stringency" of the conditions under which hybridization is measured. Hybridization conditions can be based on the melting temperature ($T_m$) of the nucleic acid binding complex, as taught in Berger and Kimmel (1987). Hybridization conditions can also be based on the washing conditions employed after hybridization as known in the art. Merely for purposes of illustration, "Low-stringency" conditions can refer to washing with a solution of 0.2×SSC/0.1% SDS at 20° C. for 15 minutes. "Medium-stringency" conditions can refer to washing with a solution of 0.2×SSC/0.1% SDS at 37° C. for 30 minutes. "High-stringency" conditions can refer to washing with a solution of 0.2×SSC/0.1% SDS at 37° C. for 45 minutes. "Very high-stringency" conditions can refer to washing with a solution of 0.2×SSC/0.1% SDS at 37° C. for 60 minutes. However, the stringency associated with the particular solution ingredients, temperature, and wash time can vary depending on the particular nucleic acids and other conditions involved. The skilled person would be able to determine the hybridization conditions associated with a desired degree of stringency.

Another aspect of the invention is use of hybridization conditions based on the melting temperature (Tm) of the nucleic acid binding complex, as taught in Berger and Kimmel (1987). For purposes of illustration, "very high stringency" typically occurs at about $T_m$−5° C. (5° C. below the $T_m$ of the probe); "high stringency" typically occurs at about 5° C. to 10° C. below $T_m$; "medium stringency" at about 10° C. to 20° C. below $T_m$; and "low stringency" at about 20° C. to 25° C. below $T_m$.

The term "identity" in the context of two nucleic acid sequences or two polypeptides refers to nucleotides or amino acid residues in the two sequences that are the same when aligned for maximum correspondence, as measured using one of the following "sequence comparison algorithms". Optimal alignment of sequences for comparison can be conducted, e.g., by the local homology algorithm of Smith & Waterman, 1981; by the homology alignment algorithm of Needleman & Wunsch, 1970; by the search for similarity method of Pearson & Lipman, 1988; by computerized implementations of these algorithms (GAP, BESTFIT, FASTA, and TFASTA in the Wisconsin Genetics Software Package, Genetics Computer Group, 575 Science Dr., Madison, Wis.) or by visual inspection.

In certain other embodiments, the sequences of *Bacillus subtilis* promoters PrrnO_P1 (SEQ ID NO: 85), PrrnO_P2 (SEQ ID NO: 89) PrrnA_P1 (SEQ ID NO: 142), PrrnA_P2 (SEQ ID NO: 143), PrrnJ_P1 (SEQ ID NO: 144), PrrnJ_P2 (SEQ ID NO: 145), PrrnI_P1 (SEQ ID NO: 146), PrrnE_P2 (SEQ ID NO: 147), PrrnE_P3 (SEQ ID NO: 148), PrrnD_P1 (SEQ ID NO: 149), PrrnD_P2 (SEQ ID NO: 150), PrrnG_P1

(SEQ ID NO: 151) and PrrnW_P1 (SEQ ID NO: 152) were aligned with default parameters using the Geneious software (Biomatters Ltd.) as shown in FIG. 6. Using the alignment, a consensus sequence for the *B. subtilis* rrn promoters was generated (SEQ ID NO: 153) and is shown at the top of FIG. 6. The consensus sequence of SEQ ID NO: 153 uses IUPAC codes defined as: N=any nucleotide, R=A/G, Y=C/T, S=G/C, W=A/T K=G/T, M=A/C, B=C/G/T, D=A/G/T, H=A/C/T, V=A/C/G.

In certain other embodiments, the promoter sequence and upstream element sequences of the *Bacillus licheniformis* ribosomal promoters rrn1-P1 (SEQ ID NO: 106), rrn2-P1 (SEQ ID NO: 107), rrn2-P2 (SEQ ID NO: 108), rrn3-P1 (SEQ ID NO: 109), rrn4-P1 (SEQ ID NO: 110), rrn4-P2 (SEQ ID NO: 111), rrn5-P1 (SEQ ID NO: 112), rrn5-P2 (SEQ ID NO: 113), rrn6-P1 (SEQ ID NO: 114), and rrn6-P2 (SEQ ID NO: 115) were aligned with default parameters using the Geneious software, as depicted in FIG. 7. Using this alignment, a consensus sequence was generated (SEQ ID NO: 154) using a threshold of 75% to generate the consensus (bases matching at least 75% of all sequences). The consensus sequence of SEQ ID NO: 154 uses IUPAC codes defined as: N=any nucleotide, R=A/G, Y=C/T, S=G/C, W=A/T K=G/T, M=A/C, B=C/G/T, D=A/G/T, H=A/C/T, V=A/C/G.

In certain other embodiments, one or more engineered promoters (e.g., an engineered double promoter, an engineered triple promoter, an engineered quad promoter, etc.) of the disclosure may further comprises other promoters with activity in a host cell, and includes mutant promoters, truncated promoters and the like which may or may not be native to the host cell. Examples of other promoters, which may be useful in a hybrid promoter of the invention, include fungal and bacterial promoters.

Some specific non-limiting examples include; the aprE promoter or a mutant aprE promoter (PCT International Publication No. WO 2001/51643); the aph promoter of the *Streptomyces fradiae* aminoglycoside 3'-phosphotransferase gene; an *Aspergillus niger* glucoamylase (glaA) promoter; the glucose isomerase (GI) promoter of *Actinoplanes missouriensis* and the derivative GI (GIT) promoter (U.S. Pat. No. 6,562,612 and EP 351029); the glucose isomerase (GI) promoter from *Streptomyces lividans*, the short wild-type GI promoter, the 1.5 GI promoter, the 1.20 GI promoter, or any of the variant GI promoters as disclosed in WO 20303/089621; the cbh1, cbh2, eg11 and eg12 promoters from filamentous fungi and specifically the *Trichoderma reesei* cellobiohydrolase promoter (GenBank Accession No. D86235); the lacZ and tac promoters (Bagdasarion et al., 1983); the ermE promoter (Ward et al., 1986 and Schmitt-John et al., 1992); and the *Bacillus subtilis* phage o29 promoters (Pulido et al., 1986). Promoters effective in Streptomyces are listed in Hopwood et al., 1986. Streptomyces phage promoters are also disclosed in Labes et al., 1997. Other promoters which may be effective for use in the hybrid promoters herein are promoters listed in Deuschle et al., 1986 and WO1996/00787.

C. Proteins of Interest

In certain embodiments, the engineered promoters of the present disclosure are operably linked to a nucleic acid (e.g., a polynucleotide or ORF) encoding a protein of interest (POI). In one or more embodiments, the POI is an enzyme, a hormone, a growth factor, a cytokine, an antibody or a fragment thereof, a receptor or a portion thereof, a reporter gene (e.g., green fluorescent protein) or other secondary metabolites.

In certain embodiments, the enzyme is a acetyl esterases, aryl esterases, aminopeptidases, amylases, arabinases, arabinofuranosidases, carboxypeptidases, catalases, cellulases, chitinases, chymosin, cutinase, deoxyribonucleases, epimerases, esterases, α-galactosidases, β-galactosidases, α-glucanases, glucan lyases, endo-β-glucanases, glucoamylases, glucose oxidases, α-glucosidases, β-glucosidases, glucuronidases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, rhamno-galacturonases, ribonucleases, thaumatin, transferases, transport proteins, transglutaminases, xylanases, hexose oxidases, and the like originating from bacteria or fungi.

In certain embodiments, the enzyme is a protease, such as a serine protease, metalloprotease, thiol or acid protease. In some embodiments, the protease will be a serine protease (e.g., a subtilisin). Serine proteases are described in Markland et al., 1983; Drenth et al., 1972; U.S. Pat. No. 4,760,025 (RE 34,606), U.S. Pat. Nos. 5,182,204 and 6,312,936 and EP No. EP 323,299). Proteases contemplated for use are also described in U.S. Patent Publication No. 2010/0152088 and PCT International Publication NOs: WO2010/056635, WO200/8010925, WO2003/62380, WO2010/56640, WO2011/72099 and the like. Means for measuring proteolytic activity are disclosed in Kalisz, 1988.

In another embodiment, the protease to be expressed by an engineered promoter of the invention is a mature BPN' (Y217L variant) protease comprising an amino acid sequence of SEQ ID NO: 40 or a precursor (full-length) BPN' (Y217L variant) protease comprising an amino acid sequence of SEQ ID NO: 41.

In other embodiments, the enzyme is an amylase, such as an amylase derived from *Trichoderma* (such as *T. reesei*), a *Trichoderma* glucoamylase, an amylase derived from *Bacillus* (such as *B. subtilis*), or an amylase derived from *Geobacillus* (such as *G. stearothermophilus*). Bacterial and fungal amylases are described in, for example, U.S. Pat. No. 8,058,033, U.S. Patent Publication No. 2010/0015686, U.S. Patent Publication No. 2009/0314286, UK application No. 1011513.7, PCT International Application No. PCT/IB2011/053018 and PCT International Publication NOs: WO2008/112459, WO2008/118377, WO2008/153805, WO2008/153815, WO2010/133644, WO2014/9952, WO201499525 and the like.

In certain embodiments, the amylase to be expressed by an engineered promoter of the invention is a *B. subtilis* AmyE amylase comprising an amino acid sequence of SEQ ID NO: 42, a *B. licheniformis* AmyL amylase comprising an amino acid sequence of SEQ ID NO: 43, a *Geobacillus stearothermophilus* AmyS amylase comprising an amino acid sequence of SEQ ID NO: 64 or a *Cytophaga* sp. amylase comprising an amino acid sequence of SEQ ID NO: 63.

In other embodiments, the enzyme is a xylanase. In certain embodiments, the xylanase is derived from *Trichoderma* (such as *T. reesei*). Bacterial and fungal xylanases are generally described in U.S. Pat. No. 7,718,411 and PCT International Publication NOs: WO2001/027252 WO2001/66711, WO2004/97001, WO2010/72225, WO2013/127069, WO2013/37933, WO2015/114108 and the like.

In other embodiments, the enzyme is a phytase. In certain embodiments, the phytase is derived from *Citrobacter* (such as *C. freundii*) or *E. coli*. In other embodiments, the phytase may be a *Buttiauxella* phytase such as a *Buttiauxella agrestis* phytase. Phytases are described in, for example, PCT International Publication Nos. WO 006/043178, WO2006/038062, WO2008/097619, WO2009/129489, WO2006/038128, WO2008/092901, WO2009/129489, WO2010/122532, WO2003/38035, WO2004/15084, WO2003/38111 and the like.

In certain other embodiments, the enzyme is a cellulase. Cellulases are (cellulolytic) enzymes that hydrolyze the β-D-glucosidic linkages in cellulose. Cellulolytic enzymes have been traditionally divided into three major classes: endoglucanases, exoglucanases (or cellobiohydrolases) and β-glucosidases (Knowles et al., 1987).

Numerous cellulases have been described in the scientific literature, examples of which include: from *Trichoderma reesei:* Shoemaker et al., 1983, which discloses CBHI; Teen et al., 1987, which discloses CBHII; Penttila et al., 1986, which discloses EGI; Saloheimo et al., 1988, whch discloses EGII; Okada et al., 1988, which discloses EGIII; Saloheimo et al., 1997, which discloses EGIV; and Saloheimo et al., 1994, which discloses EGV. Exo-cellobiohydrolases and endoglucanases from species other than *Trichoderma* have also been described in the art.

In a particular embodiment, a cellulase to be expressed by an engineered promoter of the invention is a cellulase disclosed in U.S. Pat. Nos. 6,287,839 and 6,562,612. In certain embodiments, the cellulase to be expressed is a cellulase comprising an amino acid sequence of SEQ ID NO: 1 of U.S. Pat. No. 6,562,612, or a fragment or a derivative thereof having cellulolytic activity and greater than 70% sequence identity to an active portion of SEQ ID NO: 1 of U.S. Pat. No. 6,562,612. Cellulases are generally disclosed in PCT International Publication NOs: WO2004/97001, WO2005/93050, WO2004/99370, WO2004/99369, WO2009/149202, WO2008/45214, WO2006/71598, WO2009/35537, WO2013/37933, WO2010/141779, WO2008/153903, WO2000/37614 and U.S. Patent Publication No. US2010/0048417.

In other embodiments, the enzyme is a mannanase (β-mannosidase). Mannanase enzymes hydrolyze the terminal, non-reducing β-D-mannose residues in β-D-mannosides (e.g., see, PCT International Publication NOs: WO200198462, WO2012149325, WO2012149333, Canadian Patent Application No. CA2891519 and the like).

In other embodiments, the enzyme is a pullunase. Pullulanase enzymes are a specific kind of glucanase enzymes (i.e., an amylolytic exoenzyme) that degrade pullulan (e.g., see, PCT International Publication NOs: WO2008024372, WO200151620, WO9419468 and the like). For example, in certain embodiments a pullulanase is produced as an extracellular, cell surface-anchored lipoprotein by Gram-negative bacteria (e.g., *Klebsiella*). In certain embodiments, a pullulanase is a "type I pullulanase", which specifically attacks α-1,6 linkages. In other embodiments, a pullulanase is a "type II pullulanase" which in addition to cleaving α-1,6 linkages, is further able to hydrolyze (cleave) α-1,4 linkages.

A nucleic acid encoding a POI of the disclosure (e.g., an enzyme, a hormone, a growth factor, a cytokine, an antibody and the like) may be either a native (endogenous) POI or a heterologous (exogenous) POI relative to the host cell in which the POI is expressed. In certain embodiments, a nucleic acid encoding a POI may encode a full-length protein, or a truncated form of a full-length protein. In other embodiments, a nucleic acid encoding a POI encodes a full-length "mature" form of a POI (i.e., the mature form of the POI, lacking a signal or leader peptide sequence). In other embodiments, a nucleic acid encoding a POI encodes a full-length pre-protein comprising a nucleic acid encoding an N-terminal leader or signal sequence 5' and operably linked to a nucleic acid encoding the mature form of the POI (e.g., see, Section D below). The invention is not limited to a particular coding sequence but encompasses numerous coding sequences, which are operably linked to a promoter of the invention.

Thus, in certain embodiments, a modified host cell produces an increased level of a POI, wherein various methods of screening can be applied to determine increased levels of POI produced. For example, a POI may be encoded as a polypeptide fusion and serve as a detectable label, or alternatively, the target protein itself may serve as the selectable or screenable marker. The labeled protein can also be detected using Western blotting, dot blotting (detailed descriptions of such methods are available at the website of the Cold Spring Harbor Protocols), ELISA, or, if the label is a GFP, whole cell fluorescence or FACS.

For example, a 6-histidine tag can be included to make a fusion to the target protein, and Western blots can be used to detect such a tag. Moreover, if the target protein expresses at sufficiently high levels, SDS-PAGE combined with Coomassie/silver staining, may be performed to adequately detect increases in mutant expression over wild type; and in such a case, no labeling of any molecules would be necessary.

In other embodiments, the expression of the POI in a modified (host) cell versus an unmodified (parental) cell is correlated with mRNA transcript levels. For example, certain embodiments are related to the molecular characterization of a gene or ORF encoding a POI, which usually includes a thorough analysis of the temporal and spatial distribution of RNA expression. A number of widely used procedures exist and are known in the art for detecting and determining the abundance of a particular mRNA in a total or poly(A) RNA sample. Non-limiting examples include such methods as Northern blot analysis, nuclease protection assays (NPA), in situ hybridization, and reverse transcription-polymerase chain reaction (RT-PCR).

Other methods can be employed to confirm the improved level of a protein of interest, including, for example, the detection of the increase of protein activity or amount per cell, protein activity or amount per milliliter of medium, allowing cultures or fermentations to continue efficiently for longer periods of time, or through a combination of these methods.

The detection of specific productivity is another suitable method for evaluating protein production. Specific productivity (Qp) can be determined using the following equation:
$Qp = gP/gDCW \cdot hr$
wherein, "gP" is grams of protein produced in the tank; "gDCW" is grams of dry cell weight (DCW) in the tank and "hr" is fermentation time in hours from the time of inoculation, which includes the time of production as well as growth time.

In certain embodiments, a modified host cell of the disclosure produces at least about 5%, at least about 6%, at least about 7%, at least about 8%, at least about 9%, or at least about 10% or more of a POI, as compared to its unmodified (parental) cell.

D. Signal Sequences

In certain embodiments, especially when the nucleic acid encoding a POI codes for an extracellular enzyme, such as a cellulase, protease, a xylanase, and the like, a signal sequence may be linked to the N-terminal portion of the coding sequence. The signal may be used to facilitate the extracellular secretion of a POI of the disclosure. The signal sequence may be endogenous to the host organism in which the POI is expressed or exogenous (heterologous) to the host organism in which the POI is expressed.

In certain embodiments, a gene (or ORF) encoding a POI of the disclosure further comprises (and is operably linked to) an N-terminal signal sequence derived from the *B. subtilis* subtilisin aprE gene signal sequence or a variant signal sequence thereof. In other embodiments, the signal sequence is derived from a *B. subtilis* (amyE) α-amylase gene signal sequence or a *B. subtilis* BglC (i.e., Aryl-phospho-beta-D-glucosidase (EC: 3.2.1.86)) signal sequence or variants thereof In certain other embodiments, a gene (or ORF) encoding a POI of the disclosure comprises an N-terminal signal sequence derived from the *B. licheniformis* (amyL) α-amylase gene signal sequence or a variant signal sequence thereof.

In some embodiments, the signal sequence may be altered or modified as described in PCT International Patent Publication NOs: WO2011/014278 and WO2010/123754. In certain other embodiments, the signal sequence comprises a signal sequence from a *Streptomyces cellulase* gene. In one embodiment, a preferred signal sequence is a *S. lividans* cellulase, celA (Bently et al., 2002). However, one skilled in the art is aware of numerous signal peptides, any of which are contemplated for use and are selected according to the host cell and polypeptide (POI) to be expressed in said host cell.

E. DNA Constructs and Vectors

The nucleic acid constructs of the invention, comprising an engineered promoter operably linked to a nucleic acid encoding a POI may be prepared synthetically by established standard methods in the art (e.g., the phosphoramidite method described by Beaucage and Caruthers, 1981, or the method described by Matthes et al., 1984). The nucleic acid construct may be of mixed synthetic and genomic origin and may be prepared by ligating fragments of synthetic or genomic DNA. The nucleic acid construct may also be prepared by polymerase chain reaction using specific primers, for instance as described in U.S. Pat. No. 4,683,202 or as described in Saiki et al., 1988.

A DNA construct of the invention may be inserted into a vector, such as an expression vector. A variety of vectors suitable for the cloning, transformation and expression of polypeptides in fungus, yeast and bacteria are known by those of skill in the art. Typically, the vector or cassette will comprise an engineered promoter of the invention, optionally a signal sequence, a coding region of interest and a terminator sequence.

In certain embodiments, suitable vectors may further comprise a nucleic acid sequence enabling the vector to replicate in the host cell. Examples of such enabling sequences include the origins of replication of plasmids pUC19, pACYC177, pUB110, pE194, pAMB1, pIJ702, and the like.

In other embodiments, a vector may also comprise a selectable marker (e.g., a gene the product of which complements a defect in the isolated host cell), such as the dal genes from *B. subtilis* or *B. licheniformis*; or a gene that confers antibiotic resistance such as (e.g., ampicillin resistance, spectinomycin resistance, kanamycin resistance, chloramphenicol resistance, tetracycline resistance and the like).

In certain embodiments, an expression vector includes components of a cloning vector, such as, for example, an element that permits autonomous replication of the vector in the selected host organism and one or more phenotypically detectable markers for selection purposes. Expression vectors typically also comprise control nucleotide sequences such as, for example, promoter, operator, ribosome binding site, translation initiation signal and optionally, a repressor gene, one or more activator genes sequences, or the like.

Protocols, such as described herein, used to ligate the DNA construct encoding a protein of interest, promoters, terminators and/or other elements, and to insert them into suitable vectors containing the information necessary for replication, are well known to persons skilled in the art (see, e.g., Sambrook et al., 1989, and Sambrook et al., 1989 $3^{rd}$ edition 2001).

An isolated cell, either comprising a polynucleotide construct or an expression vector, is advantageously used as a host cell in the recombinant production of a POI. The cell may be transformed with the DNA construct encoding the POI, conveniently by integrating the construct (in one or more copies) into the host chromosome. Integration is generally deemed an advantage, as the DNA sequence thus introduced is more likely to be stably maintained in the cell. Integration of the DNA constructs into the host chromosome may be performed applying conventional methods, for example, by homologous or heterologous recombination. Alternatively, the cell may be transformed with an expression vector as described above in connection with the different types of host cells.

It is, in other embodiments, advantageous to delete genes from expression hosts, where the gene deficiency can be cured by an expression vector. Known methods may be used to obtain a host cell having one or more inactivated genes. Gene inactivation may be accomplished by complete or partial deletion, by insertional inactivation or by any other means that renders a gene nonfunctional for its intended purpose, such that the gene is prevented from expression of a functional protein.

F. Transformation

A vector of the invention will be transformed into a host cell. General transformation techniques are known in the art (Ausubel et al., 1994; Campbell et al., 1989). Some of these general techniques include, but are not limited to the use of a particle or gene gun (biolistics), permeabilization of filamentous fungi cells walls prior to the transformation process (e.g., by use of high concentrations of alkali, e.g., 0.05 M to 0.4 M $CaCl_2$ or lithium acetate), protoplast fusion, electroporation, or agrobacterium mediated transformation (U.S. Pat. No. 6,255,115) and the treatment of protoplasts or spheroplasts with polyethylene glycol and $CaCl_2$, as described in Campbell et al., 1989 and Penttila et al., 1988.

Transformation and expression methods for bacteria are disclosed in Brigidi et al., 1990. A preferred general transformation and expression protocol for protease deleted *Bacillus* strains is provided in Ferrari et al., U.S. Pat. No. 5,264,366. A representative vector which can be modified with routine skill to comprise and express a nucleic acid encoding a POI is vector p2JM103BBI (Vogtentanz, 2007).

In general, DNA-mediated transformation of *Bacillus* competent cells is known in the art. For example, most of information on this process of genetic exchange originated from physicochemical studies, which resulted in the establishment of the following sequence of events leading to a transformed cell: (1) binding of the transforming DNA to competent cells, resulting in double-stranded fragmentation of the donor DNA, (2) entry of one strand of the bound DNA, accompanied by simultaneous degradation of the complementary strand, (3) integration of pieces of the single-stranded DNA into the recipient DNA and (4) expression of the newly acquired information (see, e.g., Dubnau, 1976; Venema, 1979). *Bacillus* transformation methods are further disclosed in PCT International Publication NO: WO200214490.

G. Host Cells

Host cells that may be used according to the invention include both bacterial and fungal cells. Preferred fungal host cells include filamentous fungal cells such as *Aspergillus* and *Trichoderma* cells. Preferred bacterial host cells include both gram positive and gram negative cells, including *Bacillus, Mycobacterium, Actinomyces* and *Streptomyces* host cells. Host cells also include, without limitation, *E. coli, Pseudomonas* spp. (e.g., *P. aeruginoa* and *P. alcaligenes*), *Streptomyces* spp., (e.g., *Streptomyces lividans*), *Bacillus subtilis, B. licheniformis, B. lentus, B. brevis, Geobacillus stearothermophilus, B. alkalophilus, B. amyloliquefaciens, B. coagulans, B. circulans, B. lautus, B. megatherium* and *B. thuringiensis*.

H. Cell Culture

Host cells and transformed cells of the disclosure are generally cultured in conventional nutrient media. The culture media for transformed host cells may be modified as appropriate for activating promoters and for selecting transformants. The specific culture conditions, such as temperature, pH and the like, may be those that are used for the host cell selected for expression, and will be apparent to those skilled in the art.

In addition, preferred culture conditions may be found in the scientific literature such as Sambrook, 1989; Kieser et al., 2000 and Harwood et al., 1990 and/or from the American Type Culture Collection (ATCC; Manassas, Va.). Stable transformants of fungal host cells, such as *Trichoderma* cells can generally be distinguished from unstable transformants by their faster growth rate or the formation of circular colonies with a smooth, rather than ragged outline on solid culture medium.

Recovery of Expressed Polypeptides of Interest

A polypeptide of interest produced by a transformed host cell of the disclosure may be recovered from the culture medium by conventional procedures known to one of skill in the art, including separating the host cells from the medium by centrifugation or filtration, or if necessary, disrupting the cells and removing the supernatant from the cellular fraction and debris. Typically after clarification, the proteinaceous components of the supernatant, or filtrate, are precipitated by means of a salt precipitation (e.g., ammonium sulphate). The precipitated proteins are then solubilized and may be purified by a variety of chromatographic procedures, e.g., ion exchange chromatography, gel filtration chromatography, affinity chromatography, and other art-recognized procedures. Thus, in certain embodiments, a POI expressed from an engineered promoter of the present disclosure is an isolated POI, a recovered POI and/or a purified POI.

J. Construct Assembly

In certain general embodiments, the present invention involves assembling (constructing) a nucleic acid construct in vitro, followed by direct cloning of such construct into competent host cells (e.g., *Bacillus* host cells) such that the construct becomes integrated into the host genome. For example, in certain embodiments PCR fusion, Gibson assembly and/or ligation are employed to assemble a DNA construct in vitro. In certain other embodiments, the DNA (nucleic acid) construct is a non-plasmid DNA construct. In other embodiments, the DNA construct comprises a DNA into which a mutation has been introduced. This construct is then used to transform host cells. In this regard, highly competent mutants of a host cell (e.g., *Bacillus*) are preferably employed to facilitate the direct cloning of the constructs into the cells. For example, *Bacillus* carrying the comK gene under the control of a xylose-inducible promoter (Pxyl-comK) can be reliably transformed with very high efficiency.

Any suitable method known in the art may be used to transform the cells. The DNA construct may be inserted into a vector (i.e., a plasmid), prior to transformation. In some embodiments, a circular plasmid is cut using an appropriate restriction enzyme (i.e., one that does not disrupt the DNA construct). Thus, in some embodiments, circular plasmids find use with the present invention. However, in alternative embodiments, linear plasmids are used. In some embodiments, the DNA construct (i.e., the PCR product) is used without the presence of plasmid DNA.

EXAMPLES

In order to further illustrate the present invention and advantages thereof, the following specific examples are given with the understanding that they are being offered to illustrate the present invention and should not be construed in any way as limiting its scope.

Example 1

Generation of DNA Constructs with Hybrid Promoters or Heterologous Promoters for Expression in *Bacillus*

A. DNA Constructs with Hybrid Promoters

Various DNA constructs with single heterologous promoters, single hybrid promoters, multiple (two or more) heterologous promoters, multiple (two or more) hybrid promoters, and combinations thereof, were generated for transcribing genes encoding proteins of interest in a *Bacillus* expression host. These single heterologous promoters, single hybrid promoters, multiple heterologous promoters, multiple hybrid promoters and combinations thereof are further defined as having at least one upstream promoter element (UP element) 5' and operably linked to at least one promoter element, wherein the at least one UP element and the at least one promoter element are not natively associated (i.e., operably linked) with each other nor are they derived from the same native "complete" promoter.

For example, nucleic acids with a single hybrid promoter of SEQ ID NO: 65 (Hybrid Promoter 1) or a double hybrid promoter of SEQ ID NO: 71 (Double Hybrid Promoter 7) were synthesized and ligated to a gene of interest which encodes the *B. amyloliquefaciens* BPN' (Y217L) subtilisin (SEQ ID NO: 41). The resulting DNA constructs have nucleotide sequences of SEQ ID NOS: 81 (Hybrid Promoter 1+BPN' (Y217L)) and 82 (Hybrid Promoter 7+BPN' (Y217L)), respectively. In addition, nucleic acids of single hybrid promoter with the sequence of SEQ ID NO: 65 (Hybrid Promoter 1), SEQ ID NO: 96 (Hybrid Promoter 23), and SEQ ID NO: 97 (Hybrid Promoter 24) or double hybrid promoters with the sequence of SEQ ID NO: 71 (Double Hybrid Promoter 7), SEQ ID NO: 90 (Double Hybrid Promoter 17), SEQ ID NO: 91 (Double Hybrid Promoter 18), SEQ ID NO: 92 (Double Hybrid Promoter 19), SEQ ID NO: 93 (Double Hybrid Promoter 20), SEQ ID NO: 94 (Double Hybrid Promoter 21), or SEQ ID NO: 95 (Double Hybrid Promoter 22), were synthesized and ligated to a gene of interest which encodes a *Cytophaga* sp mature amylase variant (SEQ ID NO: 63). Set forth above in Table 2 are hybrid promoters tested in the instant disclosure.

DNA fragments encompassing the desired promoter sequences were synthetically generated as gBlocks (IDT, Integrated DNA Technologies) and ligated to a gene of interest, such as BPN' Y217L, by methods known in the art. These nucleic acid constructs were inserted into DNA cassettes or amplified for transformation of suitable *B. subtilis* or *B. licheniformis* strains by methods known in the art. Suitable *B. subtilis* host cells were transformed with the resulting DNA cassettes using the protocol of Spizizen (Anagnostopoulos & Spizizen, 1961). For example, a DNA cassette used for transformation of *B. subtilis* contains a spectinomycin resistance marker (spcR, SEQ ID NO: 86) and two aprE homologous regions (SEQ ID NO: 87 and 88) for integration at the aprE locus of *B. subtilis* chromosome, and the wild-type aprE UTR (SEQ ID NO: 62). Hybrid promoters with the sequence of SEQ ID NOs: 65 (Hybrid Promoter 1), 66 (Hybrid Promoter 2), 71 (Hybrid Promoter 7), 75 (Hybrid Promoter 11), 76 (Hybrid Promoter 12), 77 (Hybrid Promoter 13), 78 (Hybrid Promoter 14), 79 (Hybrid Promoter 15), 80 (Hybrid Promoter 16), 90 (Hybrid Promoter 17), 91 (Hybrid Promoter 18), 92 (Hybrid Promoter 19), 93 (Hybrid Promoter 20), 94 (Hybrid Promoter 21), 95 (Hybrid Promoter 22), 96 (Hybrid Promoter 23), or 97 (Hybrid Promoter 24) were synthesized and ligated to a gene of interest which encodes (1) an AprE signal sequence of SEQ ID NO: 156 operably linked to a *B. subtilis* amylase E (AmyE) variant of SEQ ID NO: 42), (2) an AprE signal sequence of SEQ ID NO: 156 operably linked to a *B. licheniformis* alpha-amylase (AmyL) of SEQ ID NO: 43, (3) a *B. licheniformis* AmyL signal sequence operably linked to a *B. licheniformis* AmyL mature sequence, wherein the AmyL signal sequence and the AmyL mature sequence are operably linked as set forth in SEQ ID NO: 44, (4) an AprE signal sequence of SEQ ID NO: 156 operably linked to a *Geobacillus stearothermophilus* amylase (AmyS) variant of SEQ ID NO:64, and (5) an AprE signal sequence of SEQ ID NO: 156 operably linked to a *Cytophaga* sp amylase variant of SEQ ID NO:63. As set forth above in the preceding paragraph, in certain embodiments the expression of AmyE and AmyL in *B. subtilis* utilized the AprE signal sequence of SEQ ID NO: 156, instead of the native AmyE and AmyL signal sequences.

In addition, nucleic acid constructs with other hybrid promoters which comprise an UP element sequence selected from SEQ ID NOS: 45-61 (see, Table 1) and one, two, or three promoter sequences selected from SEQ ID NOS: 1-8, 15-18, 37, 105-115 and 118-140 were also synthesized and ligated to a gene of interest described above or to other genes of interest. The promoter sequences of SEQ ID NOs: 1-8, 15-18, 37, 105-115 and 118-140 are presented above in Tables 3-10.

These nucleic acid constructs are made in DNA cassettes or expression vectors, amplified, or used directly for transformation of various *Bacillus* species. Some of these nucleic acid constructs, cassettes, or amplification products contain the spcR marker, a chloramphenicol resistance marker, or other selectable markers. Some contain an alanine racemase gene. In certain embodiments, the nucleic acid constructs are non-integration constructs or cassettes. In other embodiments, the nucleic acid constructs are chromosomally integrated by means of specific homologous regions for integration at various sites of chromosomes of various *Bacillus* species. In other embodiments, the nucleic acid constructs are integrated into a plasmid by means of specific homologous regions for integration into naturally occurring plasmids of various *Bacillus* species.

In other embodiments, nucleic acid constructs of additional hybrid promoters of sequence of SEQ ID NOS: 67 (Hybrid Promoter 3), 68 (Hybrid Promoter 4), 69 (Hybrid Promoter 5), 70 (Hybrid Promoter 6), 72 (Hybrid Promoter 8), 73 (Hybrid Promoter 9), and 74 (Hybrid Promoter 10) are synthesized and ligated to a gene of interest which encodes BPN' Y217L subtilisin (comprising SEQ ID NO: 40 or 41), *B. subtilis* amylase E (AmyE, comprising SEQ ID NO: 42), a *B. licheniformis* alpha-amylase (AmyL, SEQ ID NO: 43 or 44), a *Geobacillus stearothermophilus* amylase (AmyS, SEQ ID NO: 64) variant, a *Cytophaga* sp amylase (SEQ ID NO :63) variant, or other amylase, pullulanase, cellulase, or protease, wild-type or variants thereof. These nucleic acid constructs are made in DNA cassettes or expression vectors, amplified, or used directly for transformation of various *Bacillus* species. In certain embodiments, the nucleic acid constructs, cassettes, or amplification products contain a spcR marker, a chloramphenicol resistance marker, or other selectable markers. In certain other embodiments, the nucleic acid constructs, cassettes, or amplification products comprise an alanine racemase gene. In certain other embodiments, the nucleic acid constructs, cassettes, or amplification products are non-integration nucleic acid constructs, cassettes, or amplification products thereof. In other embodiments, the nucleic acid constructs, cassettes, or amplification products are chromosomally integrated by means of specific homologous regions for integration at various sites of chromosomes of various *Bacillus* species. In another embodiment, the nucleic acid constructs, cassettes, or amplification products are integrated into a plasmid by means of specific homologous regions for integration into naturally occurring plasmids of various *Bacillus* species. In other embodiments, the promoter sequences of SEQ ID NOs: 15, 65, 71, 96, 97, and 101-105 have the aprE wild-type UTR of SEQ ID NO: 62 operably linked at the 3' end of the promoter sequence, while promoter sequences of SEQ ID NOs: 90, 91, 92, 93, 94 and 95 have the LAT wild-type UTR (SEQ ID NO: 155) operably linked at the 3'end of the promoter sequence.

B. Nucleic Acid Constructs with Heterologous or Homologous Complete Promoters

In this example, nucleic acid constructs with heterologous or homologous *Bacillus* promoters were generated for transcribing genes encoding proteins of interest in a *Bacillus* expression host. These promoters each have at least one native (wild-type) "complete promoter" comprising a UP element 5' and operably linked to a promoter, wherein the UP element and the promoter of the native (wild-type) "complete promoter" are natively associated and operably linked together or derived from the same native "complete promoter".

For example, nucleic acids of homologous promoters with a complete promoter sequence of *B. subtilis* rrnI (SEQ ID NO: 15), ssrA (SEQ ID NO: 25), scr (SEQ ID NO: 26), spoVG (SEQ ID NO: 27), aprE (SEQ ID NO: 28), vpr (SEQ ID NO: 29), mpr (SEQ ID NO: 30), bpr (SEQ ID NO: 31), or ispA (SEQ ID NO: 32) were synthesized and ligated to a gene of interest which encodes BPN' Y217L subtilisin (SEQ ID NO: 41). The resulting nucleic acid constructs were inserted into a DNA cassette for transformation of suitable *B. subtilis* strains. The complete promoter sequence of the *B. subtilis* rrnI of SEQ ID NO: 15 (described above) is set forth above in Table 3. The "complete" promoter sequences of SEQ ID NOs: 25-32 (described above) are presented in Tables 5, 6, and 7.

In addition, nucleic acids of heterologous or homologous promoters with a "complete promoter" sequence of *B. subtilis* rrnI (SEQ ID NO: 15), *B. licheniformis* PamyL (SEQ ID NO: 116), or *B. licheniformis* ribosomal promoters PrrnI(SEQ ID NO: 101), Prrn2 (SEQ ID NO: 102), Prrn4 (SEQ ID NO: 103), Prrn5 (SEQ ID NO: 104), or Prrn6 (SEQ ID NO: 105) were synthesized and ligated to a gene of interest which encodes *B. licheniformis* AmyL (SEQ ID NO: 43 or 44) or a *G. stearothermophilus* AmyS (SEQ ID NO: 64) variant. The resulting nucleic acid constructs were used for transformation of suitable *B. licheniformis* strains. The complete promoter sequence of the *B. subtilis* rrnI of SEQ ID NO: 15 (described above) is set forth in Table 3. The "complete" promoter sequences of *B. licheniformis* PamyL and *B. licheniformis* ribosomal promoters Prrn1, Prrn2, Prrn4, Prrn5 and Prrn6, described above, are set forth below in Table 8.

Nucleic acids of heterologous promoters with one, two, or three "complete" promoter sequences from SEQ ID NOs: 5, 9-15, 18-32, 100-117, and 141 are synthesized and ligated to a gene of interest which encodes BPN' Y217L subtilisin (comprising SEQ ID NO: 40), *B. subtilis* amylase E (AmyE, comprising SEQ ID NO: 42), *B. licheniformis* amylase L (AmyL, comprising SEQ ID NO: 43), *Geobacillus stearothermophilus* amylase (AmyS, comprising SEQ ID NO: 64) S variant or other amylase or protease variants. The heterologous "complete" promoter sequences of SEQ ID NO: 5, SEQ ID NO: 15, SEQ ID NO: 18 and SEQ ID NOs: 105-115 are presented above in Tables 3-10. The heterologous complete promoters of SEQ ID NOs: 9-14, 19-32, 100-104, 116, 117 and 141 are presented above in Tables 3-10.

In addition, nucleic acid constructs with other complete native heterologous promoters which comprise a sequence selected from SEQ ID NOs: 1-4, 6-8, 16-17, 33-39, 118-140 are also synthesized and ligated to a gene of interest described above or other genes of interest. The promoter sequences of SEQ ID NOs: 1-4, 6-8, 16-17, 33-39 and 118-140 are presented above in Tables 3-10. Additional sequences present in the constructs included the AmyL signal sequence (SEQ ID NO: 83) and the AmyL terminator sequence (SEQ ID NO: 84).

These nucleic acid constructs are made in DNA cassettes or expression vectors, amplified, or used directly for transformation of various *Bacillus* species. In certain embodiments, the nucleic acid constructs, cassettes, or amplification products contain a spcR marker, a chloramphenicol resistance marker, or other selectable markers.

In other embodiments, the nucleic acid constructs, cassettes, or amplification products contain an alanine racemase gene as a non-antibiotic-resistance marker. In certain other embodiments, the nucleic acid constructs, cassettes, or amplification products are non-chromosomal integration constructs or cassettes. In other embodiments, the nucleic acid constructs, cassettes, or amplification products are chromosomally integrated by means of specific homologous regions for integration at various sites of chromosomes of various *Bacillus* species. In certain embodiments, a nucleic acid construct or a vector thereof of the disclosure (i.e., a nucleic acid comprising an engineered promoter operably linked to a nucleic acid encoding a POI) is integrated into a homologous chromosomal region of a *Bacillus* host cell. In one particular example, a nucleic acid construct of the disclosure is incorporated into the *B. subtilis* aprE loci yhfO and yhfN.

Thus, in certain embodiments, a nucleic acid construct (or vector thereof) to be integrated into a host cell genome is flanked by 5' and 3' nucleic acid sequence comprising a *B. subtilis* aprE locus yhfO comprising a nucleic acid sequence of SEQ ID NO: 87 and a *B. subtilis* aprE yhfN locus comprising a nucleic acid sequence of SEQ ID NO: 88.

In certain other embodiments, the nucleic acid constructs, cassettes, or amplification products are integrated into a plasmid by means of specific homologous regions for integration into naturally occurring plasmids of various *Bacillus* species.

FIG. 1 of the instant disclosure shows a schematic representation of the composition of various types of promoter configurations: promoter type 1 (homologous promoter), promoter type 2 (single hybrid promoter), promoter type 3 (double hybrid promoter), which were designed and tested in these studies. Promoter type 1 is any homologous promoter where the UP element and promoter regions originate from the same original (complete) promoter (designated "Px"). Promoter type 2 is any hybrid promoter where the UP element is from one promoter (designated "Px"), and the promoter is from any other promoter (designated "Py"). Promoter type 3 is any (double) hybrid promoter where the UP element is from one promoter (designated "Px"), and two promoter regions from two different promoters designated "Py" and "Pz"), wherein the "Py" and "Pz" promoters are operably linked with an intervening UTR (i.e., the UTR is placed between the "Py" and "Px" promoters or vice versa) and optionally an additional UTR at the 3' end.

As set forth above, the 3 configurations of the "Px", "Py" and "Pz" promoter sequences can be selected from among the promoters in SEQ ID NOs: 3-20, SEQ ID NO:26, SEQ ID NO:37, and/or from the promoters in SEQ ID NOs: 101-105. An upstream (UP) element can be chosen from among the upstream element sequences in SEQ ID NO: 45-61. Upstream (UP) elements and promoter sequences can be combined using methods known in the art to create constitutive artificial promoters such as the hybrid promoters corresponding to nucleic acid sequences of SEQ ID NO 65, SEQ ID NO 67 and SEQ ID NO 71.

Example 2

Protein Expression from Native and Engineered Promoters in *Bacillus subtilis*

Figure 2:
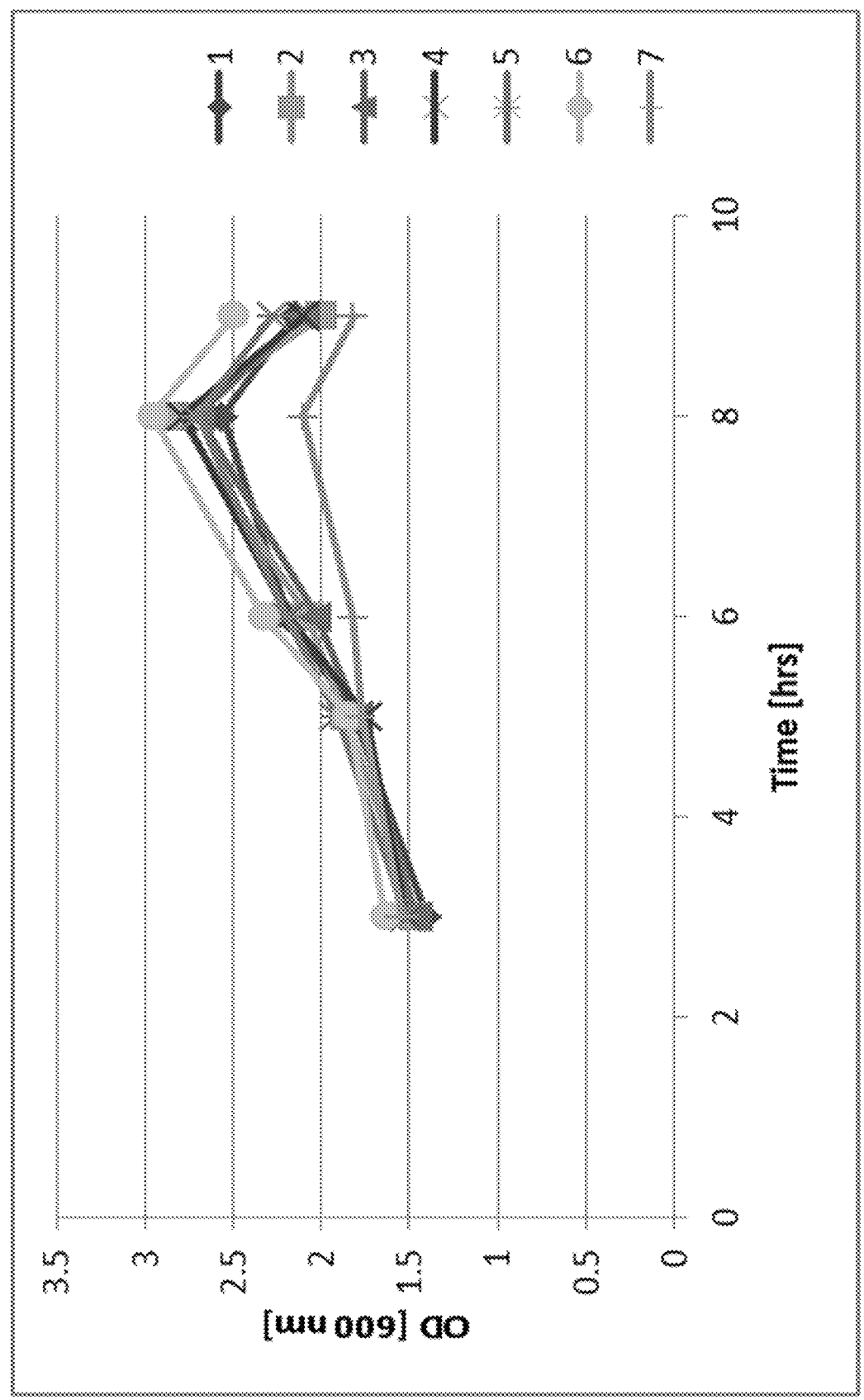
FIG. 2 shows the cell densities of *B. subtilis* cells expressing the protease BPN' (Y217L), the expression of which is driven from the following native (wild-type) and engineered (hybrid) promoters: PaprE (SEQ ID NO: 28), PssrA (SEQ ID NO: 25), Pscr (SEQ ID NO: 26), PspoVG (SEQ ID NO: 28), PrrnI-2 (SEQ ID NO: 15), hybrid promoter 1 (SEQ ID NO: 65) and hybrid promoter 7 (SEQ ID NO: 71).
Figure 3:
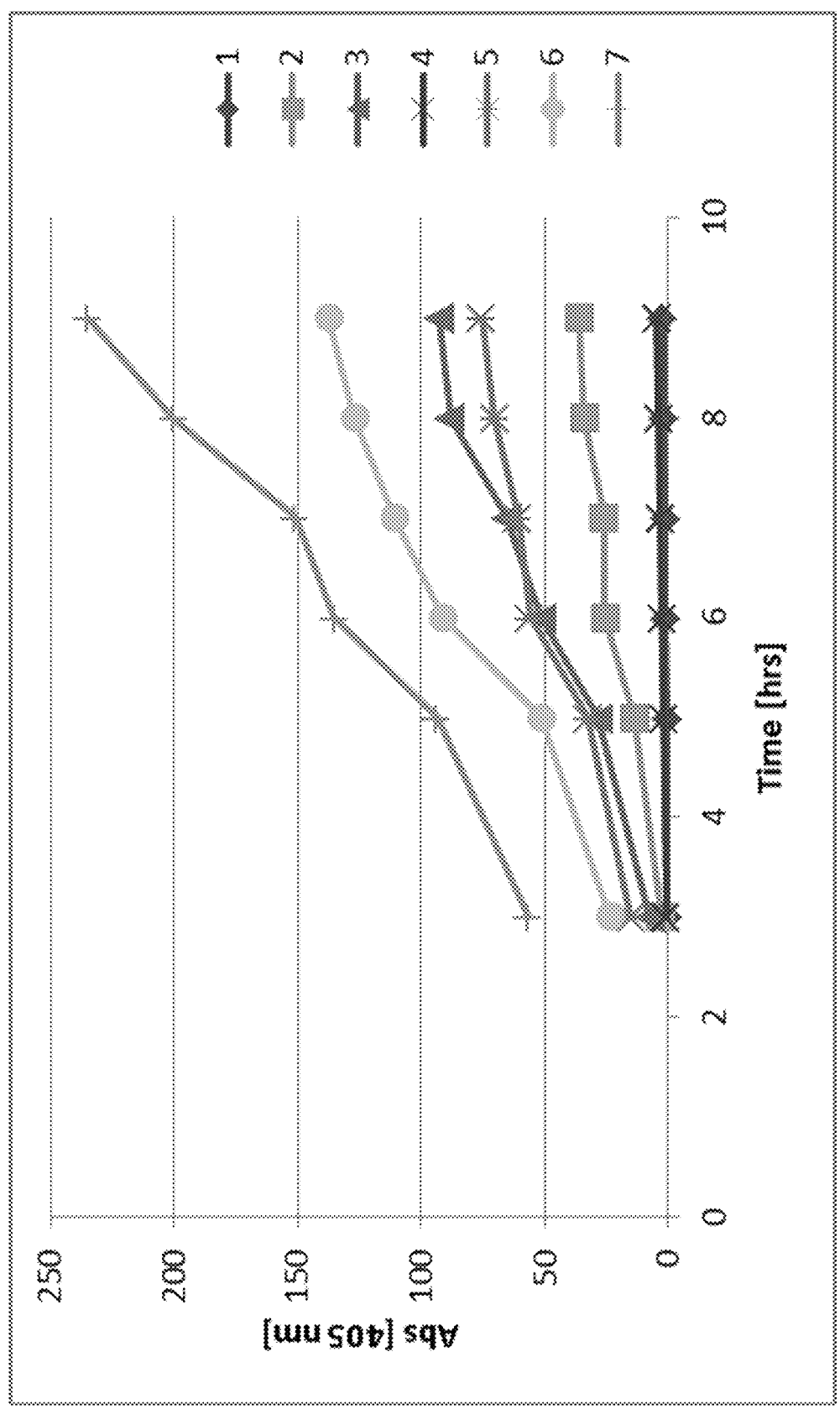
FIG. 3 shows the protease activity profiles of *B. subtilis* cultures expressing subtilisin BPN' (Y217L) under the control of the following native (wild-type) and engineered (hybrid) promoters: PaprE (SEQ ID NO: 28), PssrA (SEQ ID NO: 25), Pscr (SEQ ID NO: 26), PspoVG (SEQ ID NO: 28), PrrnI-2 (SEQ ID NO: 15), hybrid promoter 1 (SEQ ID NO: 65) and hybrid promoter 7 (SEQ ID NO: 71).

Native and synthetic promoters driving the expression of subtilisin BPN' Y217L were tested in a shake flasks cultures. The promoter sequences tested were as follows: (1) PaprE (SEQ ID NO 28), (2) PssrA (SEQ ID NO 25), (3) Pscr (SEQ ID NO 26), (4) PspoVG (SEQ ID NO 27), (5) PrrnI-2 (SEQ ID NO 15), (6) hybrid single promoter 1 (P1; SEQ ID NO 65), and (7) hybrid double promoter 7 (P7; SEQ ID NO 71). *B. subtilis* cells transformed with each of the above mentioned constructs were grown overnight in 5 mL of Luria broth. One (1) mL of each pre-culture was used to inoculate 25 mL of Brain-Heart Infusion (BHI) medium in shake flasks, incubating for 12 hours with shaker speed set at 250 rpm. Whole broth was collected hourly and diluted 10 fold to measure absorbance at 600 nm using a SpectraMax spectrophotometer (Molecular Devices, Downington, Pa., USA). The absorbance at 600 nm was plotted for each sample as a function of time and the results are shown in FIG. 2. As shown in FIG. 2, the increases in cell densities observed over time were similar for all the strains, indicating that the differences in expression of subtilisin BPN' Y217L (e.g., see FIG. 2) are not due to differences in the culture densities among the samples. In parallel, relative protein expression was monitored from the *B. subtilis* cells carrying one of the following promoter sequences: (1) PaprE (SEQ ID NO: 28), (2) PssrA (SEQ ID NO: 25), (3) Pscr (SEQ ID NO: 26), (4) PspoVG (SEQ ID NO: 27), (5) PrrnI-2 (SEQ ID NO: 15), (6) hybrid single promoter 1 (P1; SEQ ID NO 65), and (7) hybrid double promoter 7 (P7; SEQ ID NO 71), using the N-suc-AAPF-pNA substrate (Sigma Chemical Co.) as described in WO 2010/144283. This substrate is routinely used to monitor the activity of subtilisin proteases such as BPN' Y217L. Briefly, culture broth was collected during the cultivation period, diluted 40 fold in the assay buffer (100 mM Tris, 0.005% Tween 80, pH 8.6) and 10 μL of the diluted samples were arrayed in microtiter plates. The AAPF substrate stock was diluted and the assay buffer (100× dilution of 100 mg/ml AAPF stock in DMSO) and 190 μL of this solution were added to the microtiter plates. The increasing absorbance of the solution was measured at 405 nm in 20 s time increments up to 5 minutes at 25° C. degrees using a SpectraMax spectrophotometer. The absorbance at 405 nm was plotted as a function of time and the results are shown in FIG. 3. The results indicate that the promoters in SEQ ID NO: 25 (2; PssrA), SEQ ID NO: 26 (3; Pscr), SEQ ID NO: 15 (5; PrrnI-2), SEQ ID NO: 65 (6; hybrid single promoter 1) and SEQ ID NO: 71 (7; hybrid double promoter) deliver higher productivity than the promoters in SEQ ID NO: 28 (1; PaprE) and SEQ ID NO 27 (4; PspoVG). In particular, as presented in FIG. 3, hybrid promoter 1 (6; SEQ ID NO: 65) and hybrid promoter 7 (7; SEQ ID NO: 71) demonstrate the highest levels of subtilisin BPN' Y217L production under the conditions tested.

Example 3

Protein Expression from Heterologous and Engineered Promoters in *Bacillus licheniformis*

The heterologous promoter PrrnI-2 (SEQ ID NO: 15) and engineered variant promoters thereof, i.e., Variant 2 (hybrid promoter 1, SEQ ID NO: 65); Variant 3 (hybrid promoter 23, SEQ ID NO: 96); Variant 10 (hybrid promoter 22, SEQ ID NO: 95); Variant 11 (hybrid promoter 19, SEQ ID NO: 92); Variant 12 (hybrid promoter 18, SEQ ID NO: 91) and Variant 13 (hybrid promoter 17, SEQ ID NO: 90), were used to drive the expression of a *Cytophaga* sp amylase variant (SEQ ID NO:63) in *B. licheniformis*. Following *B. licheniformis* transformation, using methods known in the art, cell cultures were grown in a MOPS base medium pH 6.8, supplemented with soytone and CaCl$_2$. After 64 hours of growth in an Infors incubator at 37° C. and vigorous shaking, the amylase activity was measured in culture broth samples using the Ceralpha α-amylase assay kit (Megazyme, Wicklow, Ireland) following the manufacturer's instructions. The Ceralpha substrate is a mixture of the defined oligosaccharide nonreducing-end blocked p-nitrophenyl maltoheptaoside (BPNPG7) and excess levels of glucoamylase and β-glucosidase (which have no action on the native substrate due to the presence of the blocking group). On hydrolysis of the oligosaccharide by an endoacting α-amylase, the excess quantities of α-glucosidase and glucoamylase present in the mixture give instantaneous and quantitative hydrolysis of the p-nitrophenyl maltosaccharide fragment to glucose and free p-nitrophenol.

Thus, samples of substrate and culture supernantants were incubated for 8 minutes at 25° C. The reaction was terminated and the absorbance was measured at 405 nm using a MTP spectrophotometer. A no-enzyme control was used to correct for background absorbance. The release of the p-nitrophenol was quantified by measuring the absorbance at 405 nm, which directly relates to the level of amylase activity in the samples analyzed. The relative amylase activity detected in samples from this study are shown on FIG. 4. As shown on this graph, amylase (SEQ ID NO:63) expression from any of the engineered (variant) rrn promoters, (i.e., Variant 2 (hybrid promoter 1; SEQ ID NO: 65); Variant 3 (hybrid promoter 23; SEQ ID NO: 96); Variant 10 (hybrid promoter 22; SEQ ID NO: 95); Variant 11 (hybrid promoter 19; SEQ ID NO: 92); Variant 12 (hybrid promoter 18; SEQ ID NO: 91)and Variant 13 (hybrid promoter 17; SEQ ID NO: 90)), resulted in increased production of the amylase protein when compared to the heterologous, non-engineered rrnI-2 promoter (SEQ ID NO: 15).

Example 4

Expression of Various Amylases Using Native *Bacillus subtilis* and *Bacillus licheniformis* Ribosomal Promoters A series of native (wild-type) promoters from *B. subtilis* and *B. licheniformis* were evaluated for the expression of several bacterial amylases in a *B. licheniformis* host. The promoters evaluated were: PamyL (SEQ ID NO: 116) promoter of the amyL *Bacillus licheniformis* native amylase gene; PrrnI-2 Bsu (SEQ ID NO: 15) second promoter of the *Bacillus subtilis* ribosomal RNA rrnI; *Bacillus licheniformis* Prrn1 (SEQ ID NO: 101); *Bacillus licheniformis* Prrn2 (SEQ ID NO: 102); *Bacillus licheniformis* Prrn4 (SEQ ID NO: 103); *Bacillus licheniformis* Prrn5 (SEQ ID NO: 104) and *Bacillus licheniformis* Prrn6 (SEQ ID NO: 105).

The ribosomal sequences of SEQ ID NOs: 15, 101, 102, 103,104 and 105 contain the promoter and the native upstream (UP) element sequences. Thus, in the present example, polynucleotides encoding bacterial amylases Amy1, *B. lichenifomis* alpha-amylase L (SEQ ID NO: 43); Amy3, *Geobacillus stearothermophilus* amylase S variant (SEQ ID NO:64) and Amy4, *Cytophaga* sp amylase variant (SEQ ID NO:63), were fused (3') to the above-referenced promoters (i.e., promoters of SEQ ID NOs: 15 and 101-105). Suitable *B. licheniformis* cells transformed with these various constructs using methods known in the art. Subsequently, bacterial cultures were grown in a MOPS base medium pH 6.8, supplemented with soytone and CaCl$_2$. Cultures were incubated for 64 hours in an Infors incubator at 37° C. with vigorous agitation. The amylase activity in the cultures was then measured using the Ceralpha α-amylase assay kit (Megazyme, Wicklow, Ireland) following the manufacturer's instructions, essentially as described above in Example 3. The relative expression of the 3 bacterial amylases (i.e., Amy 1, Amy 2 and Amy 3) driven by the various native (wild-type) promoters (i.e., PamyL (SEQ ID NO: 116); PrrnI-2 Bsu (SEQ ID NO: 15); Pant (SEQ ID NO: 101); Prrn2 (SEQ ID NO: 102); Prrn4 (SEQ ID NO: 103); Prrn5 (SEQ ID NO: 104) and Prrn6 (SEQ ID NO: 105) was determined. As set forth in FIG. 5, the relative amylase production was reported as a percent of the total observed when using promoter "PAmyL" as a reference. As seen on this graph, the use of ribosomal promoters instead of the endogenous *Bacillus licheniformis* amylase promoter (PamyL), resulted in increased protein expression in most instances.

Example 5

Comparison of Various *Bacillus subtilis* and *Bacillus licheniformis* Ribosomal Promoter Sequences The sequences of *Bacillus subtilis* promoters PrrnO_P1 (SEQ ID NO: 85), PrrnO_P2 (SEQ ID NO: 89) PrrnA_P1

(SEQ ID NO: 142), PrrnA_P2 (SEQ ID NO: 143), PrrnJ_P1 (SEQ ID NO: 144), PrrnJ_P2 (SEQ ID NO: 145), PrrnI_P1 (SEQ ID NO: 146), PrrnE_P2 (SEQ ID NO: 147), PrrnE_P3 (SEQ ID NO: 148), PanD_P1 (SEQ ID NO: 149), PrrnD_P2 (SEQ ID NO: 150), PanG_P1 (SEQ ID NO: 151) and PrrnW_P1 (SEQ ID NO: 152) were aligned with default parameters using Geneious software (Biomatters Ltd.) as shown on FIG. 6. The options to display Consensus sequence and Sequence Logo were selected. The Sequence Logo is a display of the relative frequency of a nucleotide at each position, and it is represented by the size of the single letter code above each position, shown above the multiple sequence alignment in FIG. 7. Using the alignment, a consensus sequence for the *B. subtilis* rrn promoters was generated (SEQ ID NO: 153) and is shown at the top of FIG. 2. Consensus sequence uses IUPAC codes defined as: N=any nucleotide, R=A/G, Y=C/T, S=G/C, W=A/T K=G/T, M=A/C, B=C/G/T, D=A/G/T, H=A/C/T, V=A/C/G.

The promoter and upstream element sequences of the *Bacillus licheniformis* ribosomal promoters rrn1-P1 (SEQ ID NO: 106), rrn2-P1 (SEQ ID NO: 107), rrn2-P2 (SEQ ID NO: 108), rrn3-P1 (SEQ ID NO: 109), rrn4-P1 (SEQ ID NO: 110), rrn4-P2 (SEQ ID NO: 111), rrn5-P1 (SEQ ID NO: 112), rrn5-P2 (SEQ ID NO: 113), rrn6-P1 (SEQ ID NO: 114), and rrn6-P2 (SEQ ID NO: 115) were aligned with default parameters using the Geneious software. The options to display Consensus sequence and Sequence Logo were selected. The relative frequency of a nucleotide is represented by the size of the single letter code above each position, as seen in FIG. 7.

Using this alignment, a consensus sequence was generated (SEQ ID NO: 154) using a threshold of 75% to generate the consensus (bases matching at least 75% of all sequences). Consensus sequence uses IUPAC codes defined as: N=any nucleotide, R=A/G, Y=C/T, S=G/C, W=A/T K=G/T, M=A/C, B=C/G/T, D=A/G/T, H=A/C/T, V=A/C/G.

REFERENCES

Canadian Patent Application No. CA2891519
European Patent Publication No. EP 323299
European Patent Publication No. EP 351029A
PCT International Application No. PCT/IB2011/053018
PCT International Publication No. WO1996/00787
PCT International Publication No. WO2000/37614
PCT International Publication No. WO2001/027252
PCT International Publication No. WO2001/027252
PCT International Publication No. WO2001/51643
PCT International Publication No. WO200151620
PCT International Publication No. WO200198462
PCT International Publication No. WO2003/089621
PCT International Publication No. WO2004/97001
PCT International Publication No. WO2004/99369
PCT International Publication No. WO2004/99370
PCT International Publication No. WO2005/93050
PCT International Publication No. WO2006/038062
PCT International Publication No. WO2006/038128
PCT International Publication No. WO2006/043178
PCT International Publication No. WO2006/71598
PCT International Publication No. WO2008/092901
PCT International Publication No. WO2008/097619
PCT International Publication No. WO2008/153903
PCT International Publication No. WO2008/45214
PCT International Publication No. WO2008024372
PCT International Publication No. WO2009/129489
PCT International Publication No. WO2009/129489
PCT International Publication No. WO2009/149202
PCT International Publication No. WO2009/35537
PCT International Publication No. WO2010/056635
PCT International Publication No. WO2010/122532
PCT International Publication No. WO2010/123754
PCT International Publication No. WO2010/141779
PCT International Publication No. WO2011/014278
PCT International Publication No. WO2012149325
PCT International Publication No. WO2012149333
PCT International Publication No. WO2013/086219
PCT International Publication No. WO2013/37933
PCT International Publication No. WO9419468
PCT International Publication NO: WO200214490
U.S. Pat. No. 4,683,195
U.S. Pat. No. 4,683,202
U.S. Pat. No. 4,760,025 (RE 34,606)
U.S. Pat. No. 4,965,188
U.S. Pat. No. 5,182,204
U.S. Pat. No. 5,264,366.
U.S. Pat. No. 5,364,770
U.S. Pat. No. 6,022,725
U.S. Pat. No. 6,2,87,839
U.S. Pat. No. 6,255,115
U.S. Pat. No. 6,312,936
U.S. Pat. No. 6,562,612
U.S. Pat. No. 7,718,411
U.S. Pat. No. 8,058,033
U.S. Patent Publication No. 2009/0314286
U.S. Patent Publication No. 2010/0015686
U.S. Patent Publication No. 2010/0048417
U.S. Patent Publication No. 2010/0152088
UK application No. 1011513.7
Altschul, et al., *J. Mol. Biol.* 215:403-410, 1990.
Anagnostopoulos & Spizizen, "Requirement for transformation in *B. subtilis*". *J. Bacteriol.* 81:741-746, 1961.
Ausubel et al., CURRENT PROTOCOLS IN MOLECULAR BIOLOGY, 1994.
Bagdasarion et al., *Gene* 26: 273-282, 1983.
Beaucage and Caruthers, *Tetrahedron Letters* 22:1859-1869, 1981.
Bently et al., *Nature* 417:141-147, 2002.
Berger and Kimmel, Guide to Molecular Cloning Techniques, METHODS IN ENZYMOLOGY, Vol 152, 1987, Academic Press, San Diego Calif.
Brigidi et al., *FEMS Microbiol. Lett.* 55: 135-138, 1990.
Campbell et al., *Curr. Genet* 16:53-56, 1989.
Deuschle et al., *EMBO J.* 5:2987-2994, 1986.
Drenth et al., *Eur. J. Biochem.* 26:177-181, 1972.
Dubnau, "Genetic transformation of *Bacillus subtilis:* a review with emphasis on the recombination mechanism", In: Schlessinger D (ed) Microbiology 1976, Washington D.C., pages 14-27, 1976.
Edgar, "MUSCLE: a multiple sequence alignment method with reduced time and space complexity, BMC Bioinformatics, 19(5):113, 2004.
Grundy and Henkin, *J. Bacteriology,* 173:4595-4602, 1991.
Hale & Marham, THE HARPER COLLINS DICTIONARY OF BIOLOGY, Harper Perennial, NY (1991).
Harwood, et al., MOLECULAR BIOLOGICAL METHODS FOR BACILLUS, John Wiley, 1990.
Hopwood et al., GENETIC MANIPULATION OF STREPTOMYCES: A LABORATORY MANUAL, John Innis Foundation, Norwich UK, 1985.
Hopwood et al., Regulation of Gene Expression in Antibiotic-producing Streptomyces. In Booth, I. and Higgins, C. (Eds), *SYMPOSIUM OF THE SOCIETY FOR GENERAL*

MICROBIOLOGY, REGULATION OF GENE EXPRESSION, Cambridge University Press, pages 251-276, 1986.

Kalisz, "Microbial Proteinases" *ADVANCES IN BIOCHEMICAL ENGINEERING AND BIOTECHNOLOGY*, A. Fiecht Ed., 1988.

Karlin & Altschul, *Proc. Nat'l. Acad. Sci. USA* 90:5873-5787, 1993.

Kieser et al. *PRACTICAL STREPTOMYCES GENETICS*. John Innes Foundation, Norwich UK. 2000.

Kim et al., "Comparison of $P_{aprE}$, $P_{amyE}$, and $P_{P43}$ promoter strength for β-galactosidase and staphylokinase expression in *Bacillus subtilis*", *Biotechnology and Bioprocess Engineering*, 13:313, 2008.

Knowles et al., *TIBTECH* 5:255-261, 1987.

Krasny and Gourse, *EMBO* 23:4473-4483, 2004.

Krasny et al., *Mol Microbiology* 69:42-54, 2008.

Labes et al., *Microbiol.* 143:1503-1512, 1997.

Markland et al., *Honne-Seyler's Z Physiol. Chem.*, 364: 1537-1540, 1983.

Matthes et al., *EMBO Journal* 3: 801-805, 1984.

Natori et al., *J Bacteriology*, 191:4555-4561, 2009.

Needleman & Wunsch, *J. Mol. Biol.*, 48:443, 1970.

Nevalainen et al., "The Molecular Biology of Trichoderma and its Application to the Expression of Both Homologous and Heterologous Gene", in MOLECULAR INDUSTRIAL MYCOLOGY, Eds. Leon and Berka, Marcel Dekker, Inc. pp. 129-148, 1992.

Okada et al., *Appl. Environ. Microbiol.*, 64:555-563, 1988.

Pearson & Lipman, *Proc. Nat'l Acad. Sci. USA*, 85: 2444, 1988.

Penttila et al., *Gene*, 45:253-263, 1986.

Penttila et al., *Gene*, 63:11-22, 1988.

Pulido et al., *Gene* 49:377-382, 1986.

Robert C. Edgar, "MUSCLE: multiple sequence alignment with high accuracy and high throughput", *Nucleic Acids Res.*, 32 (5): 1792-1797, 2004.

Saiki et al., *Science* 239: 487-491, 1988.

Saloheimo et al., *Eur. J Biochem.*, 249:584-591, 1997.

Saloheimo et al., *Gene*, 63:11-22, 1988.

Saloheimo et al., *Molecular Microbiology*, 13: 219-228, 1994.

Samarrai et al., *J Bacteriology*, 193:723-733, 2011.

Sambrook et al., MOLECULAR CLONING: A LABORATORY MANUAL; $2^{nd}$ Ed., Cold Spring Harbor, N.Y., 1989.

Schmitt-John et al., *Microbiol. Biotechnol.* 36:493-498, 1992.

Shoemaker et al., *Bio/Technology*, 1: 691-696, 1983.

Singleton, et al., DICTIONARY OF MICROBIOLOGY AND MOLECULAR BIOLOGY, $2^{nd}$ Ed., John Wiley and Sons, New York, 1994.

Smith & Waterman, *Adv. Appl. Math*, 2:482, 1981.

Teen et al., *Gene*, 51:43-52, 1987.

Tumbough, *Molecular Microbiology* 69:10-14, 2008.

Venema, "Bacterial transformation", *Adv. Microbiol. Physiol.*, 19:245 331, 1979.

Vogtentanz et al., "A *Bacillus subtilis* fusion protein system to produce soybean Bowman-Birk protease inhibitor", *Protein Expr Purif.* 55(1): 40-52, 2007.

Ward et al., *Mol. Gen. Genet.* 203:468-478, 1986.

---

The invention claimed is:

1. An isolated nucleic acid comprising an engineered hybrid promoter operably linked to a nucleic acid encoding a protein of interest (POI), wherein the hybrid promoter comprises a nucleotide sequence having at least 98% identity to any one of SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 77, SEQ ID NO: 78, SEQ ID NO: 79, SEQ ID NO: 80, SEQ ID NO: 90, SEQ ID NO: 91, SEQ ID NO: 92, SEQ ID NO: 93, SEQ ID NO: 94, SEQ ID NO: 95, SEQ ID NO: 96 and SEQ ID NO: 97 that retains promoter activity.

2. The isolated nucleic acid of claim 1, wherein the POI is an enzyme.

3. The isolated nucleic acid of claim 2, wherein the enzyme is selected from the group consisting of acetyl esterases, aryl esterases, aminopeptidases, amylases, arabinases, arabinofuranosidases, carboxypeptidases, catalases, cellulases, chitinases, chymosin, cutinase, deoxyribonucleases, epimerases, esterases, α-galactosidases, β-galactosidases, α-glucanases, glucan lyases, endo-β-glucanases, glucoamylases, glucose oxidases, α-glucosidases, β-glucosidases, glucuronidases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, rhamno-galacturonases, ribonucleases, thaumatin, transferases, transport proteins, transglutaminases, xylanases and hexose oxidases.

4. A vector comprising a nucleic acid of claim 1.

5. The vector of claim 4, wherein the vector is an expression vector or a chromosomal integration vector.

6. A bacterial host cell comprising a vector of claim 4.

7. The host cell of claim 6, wherein the host cell is a *Bacillus* host cell selected from the group consisting of *B. subtilis, B. licheniformis, B. lentus, B. brevis, B. alkalophilus, B. amyloliquefaciens, B. coagulans, B. circulans, B. lautus, B. megatherium, B. thuringiensis* and *Geobacillus stearothermophilus*.

8. An integration vector comprising a nucleic acid of claim 1, wherein the nucleic acid of claim 1 is flanked both 5' and 3' with nucleic acid sequence homologous to a chromosomal loci of the host cell.

9. The vector of claim 8, wherein the host cell is a *Bacillus* cell and the 5' and 3' nucleic acid sequences are homologous to a *B. subtilis aprE* chromosomal loci yhfO comprising a nucleic acid of SEQ ID NO: 87 and *B. subtilis aprE* chromosomal loci yhfN comprising a nucleic acid of SEQ ID NO: 88.

10. A method for screening transformed host cells for increased expression of a POI comprising:
 (i) transforming a host cell with an isolated nucleic acid comprising a heterologous engineered hybrid promoter operably linked to a nucleic acid encoding a protein of interest (POI), wherein the hybrid promoter comprises the nucleotide sequence of any one of SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 77, SEQ ID NO: 78, SEQ ID NO: 79, SEQ ID NO: 80, SEQ ID NO: 90, SEQ ID NO: 91, SEQ ID NO: 92, SEQ ID NO: 93, SEQ ID NO: 94, SEQ ID NO: 95, SEQ ID NO: 96 and SEQ ID NO: 97,
 (ii) transforming a host cell with an isolated nucleic acid comprising its native promoter operably linked to a nucleic acid encoding the same POI as step (i), wherein the host cells transformed in steps (i) and (ii) are host cells of the same *Genus species* and genetic background, and
 (iii) culturing the modified cells under conditions such that the POI is expressed, wherein an increase in the expression of the POI coding sequence in step (i), relative to the expression of the same POI coding sequence in step (ii), indicates increased expression of the POI.

11. A method for increasing the expression of a POI in a host cell comprising:
 (i) modifying a host cell by introducing into the host cell a nucleic acid comprising an engineered hybrid promoter operably linked to a nucleic acid encoding a protein of interest (POI), wherein the hybrid promoter comprises the nucleotide sequence of any one of SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 77, SEQ ID NO: 78, SEQ ID NO: 79, SEQ ID NO: 80, SEQ ID NO: 90, SEQ ID NO: 91, SEQ ID NO: 92, SEQ ID NO: 93, SEQ ID NO: 94, SEQ ID NO: 95, SEQ ID NO: 96 and SEQ ID NO: 97 that retains promoter activity, and
 (ii) culturing the modified host cell under conditions such that the POI is expressed.

12. The method of claim 11, wherein the host cell is selected from the group consisting of *B. subtilis, B. licheniformis, B. lentus, B. brevis, B. alkalophilus, B. amyloliquefaciens, B. coagulans, B. circulans, B. lautus, B. megatherium, B. thuringiensis* and *Geobacillus stearothermophilus*.

13. The method according of claim 12, wherein the POI is an enzyme selected from the group consisting of acetyl esterases, aryl esterases, aminopeptidases, amylases, arabinases, arabinofuranosidases, carboxypeptidases, catalases, cellulases, chitinases, chymosin, cutinase, deoxyribonucleases, epimerases, esterases, α-galactosidases, β-galactosidases, α-glucanases, glucan lyases, endo-β-glucanases, glucoamylases, glucose oxidases, α-glucosidases, β-glucosidases, glucuronidases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pullulanases, mannanases, pectin methyl esterases, pectinolytic enzymes, perhydrolases, polyol oxidases, peroxidases, phenoloxidases, phytases, polygalacturonases, proteases, rhamno-galacturonases, ribonucleases, thaumatin, transferases, transport proteins, transglutaminases, xylanases, hexose oxidases.

14. The method of claim 13, further comprising isolating and purifying the POI produced.

* * * * *

SEQUENCE LISTING

```
<160> NUMBER OF SEQ ID NOS: 156

<210> SEQ ID NO 1
<211> LENGTH: 29
<212> TYPE: DNA
<213> ORGANISM: Bacillus subtilis
<220> FEATURE:
<221> NAME/KEY: misc_feature
<222> LOCATION: (7)..(23)
<223> OTHER INFORMATION: n is a, c, g, or t

<400> SEQUENCE: 1
ttgacannnn nnnnnnnnnn nnntataat                                     29

<210> SEQ ID NO 2
<211> LENGTH: 27
<212> TYPE: DNA
<213> ORGANISM: Bacillus subtilis
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (10)..(21)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t

<400> SEQUENCE: 2
rnaggawwwn nnnnnnnnnn nrngaat                                       27

<210> SEQ ID NO 3
```

```
<211> LENGTH: 46
<212> TYPE: DNA
<213> ORGANISM: Bacillus subtilis

<400> SEQUENCE: 3
atattatgta ttgacttaga caactgaagg tgttattcta atatac                46

<210> SEQ ID NO 4
<211> LENGTH: 45
<212> TYPE: DNA
<213> ORGANISM: Bacillus subtilis

<400> SEQUENCE: 4
taaaaagttg ttgacagtag cggcggtaaa tgttatgata ataaa                 45

<210> SEQ ID NO 5
<211> LENGTH: 58
<212> TYPE: DNA
<213> ORGANISM: Bacillus subtilis

<400> SEQUENCE: 5
atagattttt tttaaaaaac tattgcaata aataaataca ggtgttatat tattaaac    58

<210> SEQ ID NO 6
<211> LENGTH: 43
<212> TYPE: DNA
<213> ORGANISM: Bacillus subtilis

<400> SEQUENCE: 6
aaaaaagttg ttgacaaaaa agaagctgaa tgttatatta gta                   43

<210> SEQ ID NO 7
<211> LENGTH: 45
<212> TYPE: DNA
<213> ORGANISM: Bacillus subtilis

<400> SEQUENCE: 7
aaaaaggtgt tgactctgat tcttgaccgt gttatattat taaac                 45

<210> SEQ ID NO 8
<211> LENGTH: 45
<212> TYPE: DNA
<213> ORGANISM: Bacillus subtilis

<400> SEQUENCE: 8
aaaaaaacat ttgacaaaag aaagtcaaaa tgttatatta ataaa                 45

<210> SEQ ID NO 9
<211> LENGTH: 58
<212> TYPE: DNA
<213> ORGANISM: Bacillus subtilis

<400> SEQUENCE: 9
ataaaaaaat acaggaaaag tgttgaccaa ataaaacagg catggtatat tattaaac    58

<210> SEQ ID NO 10
<211> LENGTH: 58
<212> TYPE: DNA
<213> ORGANISM: Bacillus subtilis

<400> SEQUENCE: 10
aacaaaaaag ttttcctaag gtgtttacaa gatttaaaa atgtgtataa taagaaaa    58
```

```
<210> SEQ ID NO 11
<211> LENGTH: 57
<212> TYPE: DNA
<213> ORGANISM: Bacillus subtilis

<400> SEQUENCE: 11
tcgaaaaaac attaaaaaac ttcttgactc aacatcaaat gatagtatga tagttaa        57

<210> SEQ ID NO 12
<211> LENGTH: 67
<212> TYPE: DNA
<213> ORGANISM: Bacillus subtilis

<400> SEQUENCE: 12
gtgtaatttt ttaaaaaagt tattgacttt gaagaagtga cattgtatac taataaagtt     60
gctttaa                                                               67

<210> SEQ ID NO 13
<211> LENGTH: 62
<212> TYPE: DNA
<213> ORGANISM: Bacillus subtilis

<400> SEQUENCE: 13
agtttttaaa aaaggttatt gactttgaag aagtgacatt gtatactaat aaagttgctt     60
ta                                                                    62

<210> SEQ ID NO 14
<211> LENGTH: 66
<212> TYPE: DNA
<213> ORGANISM: Bacillus subtilis

<400> SEQUENCE: 14
cacatacagc ctaaattggg tgttgacctt ttgataatat ccgtgatata ttattattcg     60
tcgctg                                                                66

<210> SEQ ID NO 15
<211> LENGTH: 64
<212> TYPE: DNA
<213> ORGANISM: Bacillus subtilis

<400> SEQUENCE: 15
ttaaatactt tgaaaaaagt tgttgactta aagaagcta atgttatag taataaagct      60 gctt                                                                  64

<210> SEQ ID NO 16
<211> LENGTH: 47
<212> TYPE: DNA
<213> ORGANISM: Bacillus subtilis

<400> SEQUENCE: 16
tgtcataacc ctttacagtc ataaaaatta tggtataatc atttctg                   47

<210> SEQ ID NO 17
<211> LENGTH: 46
<212> TYPE: DNA
<213> ORGANISM: Bacillus subtilis

<400> SEQUENCE: 17
caaaaaagta ttgacctagt taactaaaaa tgttactatt aagtag                    46

<210> SEQ ID NO 18
```

```
<211> LENGTH: 197
<212> TYPE: DNA
<213> ORGANISM: Bacillus subtilis

<400> SEQUENCE: 18
acgccgccaa gcaattgcac attagtgtaa ttttttaaaa aagttattga ctttgaagaa      60
gtgacattgt atactaataa agttgcttta acaaagcgga caaacaaaat gatctttgaa     120
aactaaacaa gacaaaacgt acctgttaat tcagttttta aaaatcgcac agcgatgtgc     180
gtagtcagtc aaactac                                                    197

<210> SEQ ID NO 19
<211> LENGTH: 171
<212> TYPE: DNA
<213> ORGANISM: Bacillus subtilis

<400> SEQUENCE: 19
aaaagttttt aaaaagttg ttgactttga agaagtgacg ttgtatacta ataaagttgc       60
tttaacaaag cggacaaaca aatgatcttt gaaaactaa acaagacaaa acgtacctgt      120
taattcagtt tttaaaaatc gcacagcgat gtgcgtagtc agtcaaacta c              171

<210> SEQ ID NO 20
<211> LENGTH: 169
<212> TYPE: DNA
<213> ORGANISM: Bacillus subtilis

<400> SEQUENCE: 20 agttttaaa aaaggttatt gactttgaag aagtgacatt gtatactaat aaagttgctt       60
taacaaagcg gacaaacaaa atgatctttg aaaactaaac aagacaaaac gtacctgtta    120
attcagtttt taaaaatcgc acagcgatgt gcgtagtcag tcaaactac                169

<210> SEQ ID NO 21
<211> LENGTH: 240
<212> TYPE: DNA
<213> ORGANISM: Bacillus subtilis

<400> SEQUENCE: 21
tttcgaagca tgttcatgcc tgcgagaaag aataatataa gagcagtaaa gctaatcaga      60
attaacatcc tattccacaa ccccttttctt tcattatata gacaggcagt cgcactcatg    120
acggaaaagt gaactcactt agttgacctg actgatggct tatattataa tgtcaaagta    180
catgtttata tgtgtaactt aaaggtagtc gattggtgta ttcggaggga gggaaagaga    240

<210> SEQ ID NO 22
<211> LENGTH: 250
<212> TYPE: DNA
<213> ORGANISM: Bacillus subtilis

<400> SEQUENCE: 22
cgagcggaaa ttcaatggca tcaaagaatt aactgagcaa attgagaaag ataagcagga      60
agccatccgt tatttcagca atttgcggaa ataacttgca acgcacgcaa attttattct    120
aaaatatttg catataggca cgattttttag tatgatagtt ttcgtagtct taaaaccatt   180
gcttggcaat ccgaagtcac cgacggttgc taggtaactg gggctaaata tgatttggag   240
gtgaaacagg                                                            250

<210> SEQ ID NO 23
<211> LENGTH: 112
```

<212> TYPE: DNA
<213> ORGANISM: Bacillus subtilis

<400> SEQUENCE: 23
gtttttatca cctaaaagtt taccactaat ttttgtttat tatatcataa acggtgaagc    60
aataatggag gaatggttga cttcaaaaca aataaattat ataatgacct tt            112

<210> SEQ ID NO 24
<211> LENGTH: 303
<212> TYPE: DNA
<213> ORGANISM: Bacillus subtilis

<400> SEQUENCE: 24
gtaccgtgtg ttttcatttc agggaaacat gacttaattg ttcctgcaga aatatcgaaa    60
cagtattatc aagaacttga ggcacctgaa aagcgctggt ttcaatttga gaattcagct   120
cacaccccgc atattgagga gccatcatta ttcgcgaaca cattaagtcg gcatgcacgc   180
aaccatttat gatagatcct tgataaataa gaaaaacccc tgtataataa aaaagtgtg    240 caaatgatgc atattttaaa taagtcttgc aacatgcgcc tattttctgt ataatggtgt   300
ata                                                                 303

<210> SEQ ID NO 25
<211> LENGTH: 126
<212> TYPE: DNA
<213> ORGANISM: Bacillus subtilis

<400> SEQUENCE: 25
taaaggcata gtgcttgatt cgaaaatcag gcctgtgcta tactgtgttc acgatcagat    60
cacgacgcca ttcatttgaa ggatttgaca attgaaaaga gccgtgatca tgttataata   120
agacta                                                              126

<210> SEQ ID NO 26
<211> LENGTH: 70
<212> TYPE: DNA
<213> ORGANISM: Bacillus subtilis

<400> SEQUENCE: 26
aagccgccag gaaaaacttg tctgaatagt acggttgcaa ttttttagggg aaacagatat    60 acttaagtgt                                                          70

<210> SEQ ID NO 27
<211> LENGTH: 157
<212> TYPE: DNA
<213> ORGANISM: Bacillus subtilis

<400> SEQUENCE: 27
taagaaaagt gattctggga gagccgggat cactttttta tttaccttat gcccgaaatg    60
aaagctttat gacctaattg tgtaactata tcctattttt tcaaaaaata ttttaaaaac   120
gagcaggatt tcagaaaaaa tcgtggaatt gatacac                            157

<210> SEQ ID NO 28
<211> LENGTH: 542
<212> TYPE: DNA
<213> ORGANISM: Bacillus subtilis

<400> SEQUENCE: 28
cattttcttc tgctatcaaa ataacagact cgtgattttc caaacgagct ttcaaaaaag    60

```
cctctgcccc ttgcaaatcg gatgcctgtc tataaaattc ccgatattgg ttaaacagcg     120
gcgcaatggc ggccgcatct gatgtctttg cttggcgaat gttcatctta tttcttcctc     180
cctctcaata attttttcat tctatcccct ttctgtaaag tttattttc agaatacttt      240 tatcatcatg ctttgaaaaa atatcacgat aatatccatt gttctcacgg aagcacacgc     300
aggtcatttg aacgaatttt ttcgacagga atttgccggg actcaggagc atttaaccta     360
aaaaagcatg acatttcagc ataatgaaca tttactcatg tctattttcg ttcttttctg     420
tatgaaaata gttatttcga gtctctacgg aaatagcgag agatgatata cctaaataga     480
gataaaatca tctcaaaaaa atgggtctac taaaatatta ttccatctat tacaataaat     540
tc                                                                    542

<210> SEQ ID NO 29
<211> LENGTH: 320
<212> TYPE: DNA
<213> ORGANISM: Bacillus subtilis

<400> SEQUENCE: 29
agctgaaaga attgaaatga aaattggaga accgctttga aaactttata cacaagttat      60
cccaaagata agaacaactt aatcacaaga gatatccaca tgtccacaaa ctctatctat     120
attttgtata cgaacgtata ttcctaacta tatatataca caggtttatt cacttataca     180
cagggttctg tgtataactc cttcgttata cacaaacaaa atccaataaa tggtccaaat     240
gacacaagga ttttttgaa ttttcaagaa atatatacta gatctttcac attttttcta     300
aatacaaagg gggaaacaca                                                 320

<210> SEQ ID NO 30
<211> LENGTH: 200
<212> TYPE: DNA
<213> ORGANISM: Bacillus subtilis

<400> SEQUENCE: 30
gttgaaacgg caagagagaa tgcaaagaaa gcgttggacc agctaatttt aaaatagagt      60
ttgaacaggt cttgtcatgg gacaaggcct gttttttct ttctccgtaa agtttttatc     120
ataagaatca gaaacctgat tataatgtaa aagtcttcca tcgatacggg tggttgacac     180
taaaggaggg agatgacaaa                                                 200

<210> SEQ ID NO 31
<211> LENGTH: 300
<212> TYPE: DNA
<213> ORGANISM: Bacillus subtilis

<400> SEQUENCE: 31
taaaggacaa aatcgttttc gattttgtcc ttttttgttt ttctcttcac actttccttc      60
ttataaagtc ttttttccct attgcttcctt cgcttagtaa caaaacagat aattagaccc    120
atttattttt gtgacatttt tatcattttc atatatatgg aaattgaatg acatgaaacg     180
acaatatctg taattcagat tgtctacagt taatatacag cgatgttctg acaaaccatt     240
cattattaaa aggagggacg acacttttt taaaaagcat gttgaaaaag ggggatgaaa      300

<210> SEQ ID NO 32
<211> LENGTH: 200
<212> TYPE: DNA
<213> ORGANISM: Bacillus subtilis

<400> SEQUENCE: 32
```

```
ctattataac ttgacttaca gttgaatccc agtcatacat gttgaagcca tccaatattt    60
tgaagattac taattctttg gtgtgtatcc tatttttca aaatgcttca aatggctctg   120
tccgagcgct tgcttttttc atataatatg aggcaacacc cttgaatcca cttgcaagca   180
taaaaaagga gggctttttt                                               200

<210> SEQ ID NO 33
<211> LENGTH: 29
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (8)..(23)
<223> OTHER INFORMATION: n is a, c, g, or t

<400> SEQUENCE: 33
attgaaannn nnnnnnnnn nnntataat                                       29

<210> SEQ ID NO 34
<211> LENGTH: 30
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (7)..(24)
<223> OTHER INFORMATION: n is a, c, g, or t

<400> SEQUENCE: 34
atccacnnnn nnnnnnnnnn nnnntatatt                                     30

<210> SEQ ID NO 35
<211> LENGTH: 32
<212> TYPE: DNA
<213> ORGANISM: Artificial Sequence
<220> FEATURE:
<223> OTHER INFORMATION: Consnesus Sequence
<220> FEATURE:
<221> NAME/KEY: misc_feature
<222> LOCATION: (8)..(26)
<223> OTHER INFORMATION: n is a, c, g, or t

<400> SEQUENCE: 35
tttatcannn nnnnnnnnn nnnnnntata at                                   32

<210> SEQ ID NO 36
<211> LENGTH: 30
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (7)..(24)
<223> OTHER INFORMATION: n is a, c, g, or t

<400> SEQUENCE: 36
acaatannnn nnnnnnnnnn nnnntacagt                                     30

<210> SEQ ID NO 37
<211> LENGTH: 30
<212> TYPE: DNA
<213> ORGANISM: Artificial Sequence
<220> FEATURE:
```

```
<223> OTHER INFORMATION: Consensus Sequence
<220> FEATURE:
<221> NAME/KEY: misc_feature
<222> LOCATION: (8)..(24)
<223> OTHER INFORMATION: n is a, c, g, or t

<400> SEQUENCE: 37
gttgcaannn nnnnnnnnnn nnnntatact                                    30

<210> SEQ ID NO 38
<211> LENGTH: 32
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (8)..(26)
<223> OTHER INFORMATION: n is a, c, g, or t

<400> SEQUENCE: 38
gtctactnnn nnnnnnnnnn nnnnnntaca at                                 32

<210> SEQ ID NO 39
<211> LENGTH: 30
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (8)..(24)
<223> OTHER INFORMATION: n is a, c, g, or t

<400> SEQUENCE: 39
ctgtccgnnn nnnnnnnnnn nnnntataat                                    30

<210> SEQ ID NO 40
<211> LENGTH: 275
<212> TYPE: PRT
<213> ORGANISM: Bacillus amyloliquefaciens

<400> SEQUENCE: 40
```

| Ala | Gln | Ser | Val | Pro | Tyr | Gly | Val | Ser | Gln | Ile | Lys | Ala | Pro | Ala | Leu |
|---|---|---|---|---|---|---|---|---|---|---|---|---|---|---|---|
| 1 | | | | 5 | | | | | 10 | | | | | 15 | |

| His | Ser | Gln | Gly | Tyr | Thr | Gly | Ser | Asn | Val | Lys | Val | Ala | Val | Ile | Asp |
|---|---|---|---|---|---|---|---|---|---|---|---|---|---|---|---|
| | | | 20 | | | | | 25 | | | | | 30 | | |

| Ser | Gly | Ile | Asp | Ser | Ser | His | Pro | Asp | Leu | Lys | Val | Ala | Gly | Gly | Ala |
|---|---|---|---|---|---|---|---|---|---|---|---|---|---|---|---|
| | | 35 | | | | | 40 | | | | | 45 | | | |

| Ser | Met | Val | Pro | Ser | Glu | Thr | Asn | Pro | Phe | Gln | Asp | Asn | Asn | Ser | His |
|---|---|---|---|---|---|---|---|---|---|---|---|---|---|---|---|
| 50 | | | | | 55 | | | | | 60 | | | | | |

| Gly | Thr | His | Val | Ala | Gly | Thr | Val | Ala | Ala | Leu | Asn | Asn | Ser | Ile | Gly |
|---|---|---|---|---|---|---|---|---|---|---|---|---|---|---|---|
| 65 | | | | | 70 | | | | | 75 | | | | | 80 |

| Val | Leu | Gly | Val | Ala | Pro | Ser | Ala | Ser | Leu | Tyr | Ala | Val | Lys | Val | Leu |
|---|---|---|---|---|---|---|---|---|---|---|---|---|---|---|---|
| | | | | 85 | | | | | 90 | | | | | 95 | |

| Gly | Ala | Asp | Gly | Ser | Gly | Gln | Tyr | Ser | Trp | Ile | Ile | Asn | Gly | Ile | Glu |
|---|---|---|---|---|---|---|---|---|---|---|---|---|---|---|---|
| | | | 100 | | | | | 105 | | | | | 110 | | |

| Trp | Ala | Ile | Ala | Asn | Asn | Met | Asp | Val | Ile | Asn | Met | Ser | Leu | Gly | Gly |
|---|---|---|---|---|---|---|---|---|---|---|---|---|---|---|---|
| | | 115 | | | | | 120 | | | | | 125 | | | |

| Pro | Ser | Gly | Ser | Ala | Ala | Leu | Lys | Ala | Ala | Val | Asp | Lys | Ala | Val | Ala |
|---|---|---|---|---|---|---|---|---|---|---|---|---|---|---|---|
| 130 | | | | | 135 | | | | | 140 | | | | | |

| Ser | Gly | Val | Val | Val | Val | Ala | Ala | Ala | Gly | Asn | Glu | Gly | Thr | Ser | Gly |
|---|---|---|---|---|---|---|---|---|---|---|---|---|---|---|---|
| 145 | | | | | 150 | | | | | 155 | | | | | 160 |

```
Ser Ser Ser Thr Val Gly Tyr Pro Gly Lys Tyr Pro Ser Val Ile Ala
            165                 170                 175

Val Gly Ala Val Asp Ser Ser Asn Gln Arg Ala Ser Phe Ser Ser Val
        180                 185                 190

Gly Pro Glu Leu Asp Val Met Ala Pro Gly Val Ser Ile Gln Ser Thr
    195                 200                 205

Leu Pro Gly Asn Lys Tyr Gly Ala Leu Asn Gly Thr Ser Met Ala Ser
210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 41
<211> LENGTH: 382
<212> TYPE: PRT
<213> ORGANISM: Bacillus amyloliquefaciens

<400> SEQUENCE: 41

Val Arg Ser Lys Lys Leu Trp Ile Ser Leu Leu Phe Ala Leu Ala Leu
1               5                   10                  15

Ile Phe Thr Met Ala Phe Gly Ser Thr Ser Ser Ala Gln Ala Ala Gly
            20                  25                  30

Lys Ser Asn Gly Glu Lys Lys Tyr Ile Val Gly Phe Lys Gln Thr Met
        35                  40                  45

Ser Thr Met Ser Ala Ala Lys Lys Lys Asp Val Ile Ser Glu Lys Gly
    50                  55                  60

Gly Lys Val Gln Lys Gln Phe Lys Tyr Val Asp Ala Ala Ser Ala Thr
65                  70                  75                  80

Leu Asn Glu Lys Ala Val Lys Glu Leu Lys Lys Asp Pro Ser Val Ala
                85                  90                  95

Tyr Val Glu Glu Asp His Val Ala His Ala Tyr Ala Gln Ser Val Pro
            100                 105                 110

Tyr Gly Val Ser Gln Ile Lys Ala Pro Ala Leu His Ser Gln Gly Tyr
        115                 120                 125

Thr Gly Ser Asn Val Lys Val Ala Val Ile Asp Ser Gly Ile Asp Ser
    130                 135                 140

Ser His Pro Asp Leu Lys Val Ala Gly Gly Ala Ser Met Val Pro Ser
145                 150                 155                 160

Glu Thr Asn Pro Phe Gln Asp Asn Asn Ser His Gly Thr His Val Ala
                165                 170                 175

Gly Thr Val Ala Ala Leu Asn Asn Ser Ile Gly Val Leu Gly Val Ala
            180                 185                 190

Pro Ser Ala Ser Leu Tyr Ala Val Lys Val Leu Gly Ala Asp Gly Ser
        195                 200                 205

Gly Gln Tyr Ser Trp Ile Ile Asn Gly Ile Glu Trp Ala Ile Ala Asn
    210                 215                 220

Asn Met Asp Val Ile Asn Met Ser Leu Gly Gly Pro Ser Gly Ser Ala
225                 230                 235                 240

Ala Leu Lys Ala Ala Val Asp Lys Ala Val Ala Ser Gly Val Val Val
```

```
                    245                 250                 255
Val Ala Ala Ala Gly Asn Glu Gly Thr Ser Gly Ser Ser Ser Thr Val
                260                 265                 270

Gly Tyr Pro Gly Lys Tyr Pro Ser Val Ile Ala Val Gly Ala Val Asp
            275                 280                 285

Ser Ser Asn Gln Arg Ala Ser Phe Ser Ser Val Gly Pro Glu Leu Asp
        290                 295                 300

Val Met Ala Pro Gly Val Ser Ile Gln Ser Thr Leu Pro Gly Asn Lys
305                 310                 315                 320

Tyr Gly Ala Leu Asn Gly Thr Ser Met Ala Ser Pro His Val Ala Gly
                325                 330                 335

Ala Ala Ala Leu Ile Leu Ser Lys His Pro Asn Trp Thr Asn Thr Gln
                340                 345                 350

Val Arg Ser Ser Leu Glu Asn Thr Thr Thr Lys Leu Gly Asp Ser Phe
            355                 360                 365

Tyr Tyr Gly Lys Gly Leu Ile Asn Val Gln Ala Ala Gln
        370                 375                 380

<210> SEQ ID NO 42
<211> LENGTH: 425
<212> TYPE: PRT
<213> ORGANISM: Bacillus subtilis

<400> SEQUENCE: 42

Leu Thr Ala Pro Ser Ile Lys Ser Gly Thr Ile Leu His Ala Trp Asn
1               5                   10                  15

Trp Ser Phe Asn Thr Leu Lys His Asn Met Lys Asp Ile His Asp Ala
                20                  25                  30

Gly Tyr Thr Ala Ile Gln Thr Ser Pro Ile Asn Gln Val Lys Glu Gly
            35                  40                  45

Asn Gln Gly Asp Lys Ser Met Ser Asn Trp Tyr Trp Leu Tyr Gln Pro
        50                  55                  60

Thr Ser Tyr Gln Ile Gly Asn Arg Tyr Leu Gly Thr Glu Gln Glu Phe
65              70                  75                  80

Lys Glu Met Cys Ala Ala Glu Glu Tyr Gly Ile Lys Val Ile Val
                85                  90                  95

Asp Ala Val Ile Asn His Thr Thr Ser Asp Tyr Ala Ala Ile Ser Asn
                100                 105                 110

Glu Val Lys Ser Ile Pro Asn Trp Thr His Gly Asn Thr Gln Ile Lys
            115                 120                 125

Asn Trp Ser Asp Arg Trp Asp Val Thr Gln Asn Ser Leu Leu Gly Leu
        130                 135                 140

Tyr Asp Trp Asn Thr Gln Asn Thr Gln Val Gln Ser Tyr Leu Lys Arg
145                 150                 155                 160

Phe Leu Asp Arg Ala Leu Asn Asp Gly Ala Asp Gly Phe Arg Phe Asp
                165                 170                 175

Ala Ala Lys His Ile Glu Leu Pro Asp Asp Gly Ser Tyr Gly Ser Gln
            180                 185                 190

Phe Trp Pro Asn Ile Thr Asn Thr Ser Ala Glu Phe Gln Tyr Gly Glu
        195                 200                 205

Ile Leu Gln Asp Ser Ala Ser Arg Asp Ala Ala Tyr Ala Asn Tyr Met
    210                 215                 220

Asp Val Thr Ala Ser Asn Tyr Gly His Ser Ile Arg Ser Ala Leu Lys
225                 230                 235                 240
```

-continued

```
Asn Arg Asn Leu Gly Val Ser Asn Ile Ser His Tyr Ala Ser Asp Val
                245                 250                 255

Ser Ala Asp Lys Leu Val Thr Trp Val Glu Ser His Asp Thr Tyr Ala
            260                 265                 270

Asn Asp Asp Glu Glu Ser Thr Trp Met Ser Asp Asp Ile Arg Leu
        275                 280                 285

Gly Trp Ala Val Ile Ala Ser Arg Ser Gly Ser Thr Pro Leu Phe Phe
290                 295                 300

Ser Arg Pro Glu Gly Gly Asn Gly Val Arg Phe Pro Gly Lys Ser
305                 310                 315                 320

Gln Ile Gly Asp Arg Gly Ser Ala Leu Phe Glu Asp Gln Ala Ile Thr
            325                 330                 335

Ala Val Asn Arg Phe His Asn Val Met Ala Gly Gln Pro Glu Glu Leu
        340                 345                 350

Ser Asn Pro Asn Gly Asn Asn Gln Ile Phe Met Asn Gln Arg Gly Ser
    355                 360                 365

His Gly Val Val Leu Ala Asn Ala Gly Ser Ser Val Ser Ile Asn
370                 375                 380

Thr Ala Thr Lys Leu Pro Asp Gly Arg Tyr Asp Asn Lys Ala Gly Ala
385                 390                 395                 400

Gly Ser Phe Gln Val Asn Asp Gly Lys Leu Thr Gly Thr Ile Asn Ala
            405                 410                 415

Arg Ser Val Ala Val Leu Tyr Pro Asp
        420                 425

<210> SEQ ID NO 43
<211> LENGTH: 512
<212> TYPE: PRT
<213> ORGANISM: Bacillus licheniformis

<400> SEQUENCE: 43

Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ser Ala Ala Asn Leu
            20                  25                  30

Asn Gly Thr Leu Met Gln Tyr Phe Glu Trp Tyr Met Pro Asn Asp Gly
        35                  40                  45

Gln His Trp Lys Arg Leu Gln Asn Asp Ser Ala Tyr Leu Ala Glu His
    50                  55                  60

Gly Ile Thr Ala Val Trp Ile Pro Pro Ala Tyr Lys Gly Thr Ser Gln
65                  70                  75                  80

Ala Asp Val Gly Tyr Gly Ala Tyr Asp Leu Tyr Asp Leu Gly Glu Phe
                85                  90                  95

His Gln Lys Gly Thr Val Arg Thr Lys Tyr Gly Thr Lys Gly Glu Leu
            100                 105                 110

Gln Ser Ala Ile Lys Ser Leu His Ser Arg Asp Ile Asn Val Tyr Gly
        115                 120                 125

Asp Val Val Ile Asn His Lys Gly Gly Ala Asp Ala Thr Glu Asp Val
    130                 135                 140

Thr Ala Val Glu Val Asp Pro Ala Asp Arg Asn Arg Val Ile Ser Gly
145                 150                 155                 160

Glu His Leu Ile Lys Ala Trp Thr His Phe His Phe Pro Gly Arg Gly
                165                 170                 175

Ser Thr Tyr Ser Asp Phe Lys Trp His Trp Tyr His Phe Asp Gly Thr
            180                 185                 190
```

```
Asp Trp Asp Glu Ser Arg Lys Leu Asn Arg Ile Tyr Lys Phe Gln Gly
            195                 200                 205

Lys Ala Trp Asp Trp Glu Val Ser Asn Glu Asn Gly Asn Tyr Asp Tyr
210                 215                 220

Leu Met Tyr Ala Asp Ile Asp Tyr Asp His Pro Asp Val Ala Ala Glu
225                 230                 235                 240

Ile Lys Arg Trp Gly Thr Trp Tyr Ala Asn Glu Leu Gln Leu Asp Gly
            245                 250                 255

Phe Arg Leu Asp Ala Val Lys His Ile Lys Phe Ser Phe Leu Arg Asp
            260                 265                 270

Trp Val Asn His Val Arg Glu Lys Thr Gly Lys Glu Met Phe Thr Val
            275                 280                 285

Ala Glu Tyr Trp Gln Asn Asp Leu Gly Ala Leu Glu Asn Tyr Leu Asn
            290                 295                 300

Lys Thr Asn Phe Asn His Ser Val Phe Asp Val Pro Leu His Tyr Gln
305                 310                 315                 320

Phe His Ala Ala Ser Thr Gln Gly Gly Gly Tyr Asp Met Arg Lys Leu
                325                 330                 335

Leu Asn Gly Thr Val Val Ser Lys His Pro Leu Lys Ser Val Thr Phe
            340                 345                 350

Val Asp Asn His Asp Thr Gln Pro Gly Gln Ser Leu Glu Ser Thr Val
            355                 360                 365

Gln Thr Trp Phe Lys Pro Leu Ala Tyr Ala Phe Ile Leu Thr Arg Glu
370                 375                 380

Ser Gly Tyr Pro Gln Val Phe Tyr Gly Asp Met Tyr Gly Thr Lys Gly
385                 390                 395                 400

Asp Ser Gln Arg Glu Ile Pro Ala Leu Lys His Lys Ile Glu Pro Ile
                405                 410                 415

Leu Lys Ala Arg Lys Gln Tyr Ala Tyr Gly Ala Gln His Asp Tyr Phe
            420                 425                 430

Asp His His Asp Ile Val Gly Trp Thr Arg Glu Gly Asp Ser Ser Val
            435                 440                 445

Ala Asn Ser Gly Leu Ala Ala Leu Ile Thr Asp Gly Pro Gly Gly Ala
            450                 455                 460

Lys Arg Met Tyr Val Gly Arg Gln Asn Ala Gly Glu Thr Trp His Asp
465                 470                 475                 480

Ile Thr Gly Asn Arg Ser Glu Pro Val Val Ile Asn Ser Glu Gly Trp
                485                 490                 495

Gly Glu Phe His Val Asn Gly Gly Ser Val Ser Ile Tyr Val Gln Arg
            500                 505                 510

<210> SEQ ID NO 44
<211> LENGTH: 512
<212> TYPE: PRT
<213> ORGANISM: Bacillus licheniformis

<400> SEQUENCE: 44

Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ser Ala Ala Asn Leu
            20                  25                  30

Asn Gly Thr Leu Met Gln Tyr Phe Glu Trp Tyr Met Pro Asn Asp Gly
            35                  40                  45

Gln His Trp Lys Arg Leu Gln Asn Asp Ser Ala Tyr Leu Ala Glu His
```

```
            50                  55                  60
Gly Ile Thr Ala Val Trp Ile Pro Pro Ala Tyr Lys Gly Thr Ser Gln
 65                  70                  75                  80

Ala Asp Val Gly Tyr Gly Ala Tyr Asp Leu Tyr Asp Leu Gly Glu Phe
                 85                  90                  95

His Gln Lys Gly Thr Val Arg Thr Lys Tyr Gly Thr Lys Gly Glu Leu
            100                 105                 110

Gln Ser Ala Ile Lys Ser Leu His Ser Arg Asp Ile Asn Val Tyr Gly
            115                 120                 125

Asp Val Val Ile Asn His Lys Gly Ala Asp Ala Thr Glu Asp Val
            130                 135                 140

Thr Ala Val Glu Val Asp Pro Ala Asp Arg Asn Arg Val Ile Ser Gly
145                 150                 155                 160

Glu His Leu Ile Lys Ala Trp Thr His Phe His Phe Pro Gly Arg Gly
                165                 170                 175

Ser Thr Tyr Ser Asp Phe Lys Trp His Trp Tyr His Phe Asp Gly Thr
                180                 185                 190

Asp Trp Asp Glu Ser Arg Lys Leu Asn Arg Ile Tyr Lys Phe Gln Gly
            195                 200                 205

Lys Ala Trp Asp Trp Glu Val Ser Asn Glu Asn Gly Asn Tyr Asp Tyr
            210                 215                 220

Leu Met Tyr Ala Asp Ile Asp Tyr Asp His Pro Asp Val Ala Ala Glu
225                 230                 235                 240

Ile Lys Arg Trp Gly Thr Trp Tyr Ala Asn Glu Leu Gln Leu Asp Gly
                245                 250                 255

Phe Arg Leu Asp Ala Val Lys His Ile Lys Phe Ser Phe Leu Arg Asp
                260                 265                 270

Trp Val Asn His Val Arg Glu Lys Thr Gly Lys Glu Met Phe Thr Val
            275                 280                 285

Ala Glu Tyr Trp Gln Asn Asp Leu Gly Ala Leu Glu Asn Tyr Leu Asn
            290                 295                 300

Lys Thr Asn Phe Asn His Ser Val Phe Asp Val Pro Leu His Tyr Gln
305                 310                 315                 320

Phe His Ala Ala Ser Thr Gln Gly Gly Gly Tyr Asp Met Arg Lys Leu
                325                 330                 335

Leu Asn Gly Thr Val Val Ser Lys His Pro Leu Lys Ser Val Thr Phe
            340                 345                 350

Val Asp Asn His Asp Thr Gln Pro Gly Gln Ser Leu Glu Ser Thr Val
            355                 360                 365

Gln Thr Trp Phe Lys Pro Leu Ala Tyr Ala Phe Ile Leu Thr Arg Glu
            370                 375                 380

Ser Gly Tyr Pro Gln Val Phe Tyr Gly Asp Met Tyr Gly Thr Lys Gly
385                 390                 395                 400

Asp Ser Gln Arg Glu Ile Pro Ala Leu Lys His Lys Ile Glu Pro Ile
                405                 410                 415

Leu Lys Ala Arg Lys Gln Tyr Ala Tyr Gly Ala Gln His Asp Tyr Phe
            420                 425                 430

Asp His His Asp Ile Val Gly Trp Thr Arg Glu Gly Asp Ser Ser Val
            435                 440                 445

Ala Asn Ser Gly Leu Ala Ala Leu Ile Thr Asp Gly Pro Gly Gly Ala
            450                 455                 460

Lys Arg Met Tyr Val Gly Arg Gln Asn Ala Gly Glu Thr Trp His Asp
465                 470                 475                 480
```

```
Ile Thr Gly Asn Arg Ser Glu Pro Val Val Ile Asn Ser Glu Gly Trp
            485                 490                 495
Gly Glu Phe His Val Asn Gly Gly Ser Val Ser Ile Tyr Val Gln Arg
            500                 505                 510

<210> SEQ ID NO 45
<211> LENGTH: 21
<212> TYPE: DNA
<213> ORGANISM: Bacillus subtilis

<400> SEQUENCE: 45
taaaaacttt ttcaaaaaag t                                            21

<210> SEQ ID NO 46
<211> LENGTH: 21
<212> TYPE: DNA
<213> ORGANISM: Bacillus subtilis

<400> SEQUENCE: 46
aaaagaaaat gctaaaaagt t                                            21

<210> SEQ ID NO 47
<211> LENGTH: 21
<212> TYPE: DNA
<213> ORGANISM: Bacillus subtilis

<400> SEQUENCE: 47
aaaagaactt caaaaaaagt t                                            21

<210> SEQ ID NO 48
<211> LENGTH: 21
<212> TYPE: DNA
<213> ORGANISM: Bacillus subtilis

<400> SEQUENCE: 48
ttaaatactt tgaaaaagt t                                             21

<210> SEQ ID NO 49
<211> LENGTH: 21
<212> TYPE: DNA
<213> ORGANISM: Bacillus subtilis

<400> SEQUENCE: 49
cgaaaaaaca ttaaaaaact t                                            21

<210> SEQ ID NO 50
<211> LENGTH: 21
<212> TYPE: DNA
<213> ORGANISM: Bacillus subtilis

<400> SEQUENCE: 50
ggaaaataaa tcaaaaaaac a                                            21

<210> SEQ ID NO 51
<211> LENGTH: 24
<212> TYPE: DNA
<213> ORGANISM: Bacillus subtilis

<400> SEQUENCE: 51
attttttcaa aaaatatttt aaaa                                         24

<210> SEQ ID NO 52
```

```
<211> LENGTH: 15
<212> TYPE: DNA
<213> ORGANISM: Bacillus subtilis

<400> SEQUENCE: 52
aaaaatattt taaaa                                                        15

<210> SEQ ID NO 53
<211> LENGTH: 30
<212> TYPE: DNA
<213> ORGANISM: Bacillus subtilis

<400> SEQUENCE: 53
attttttcaa aaatattttt aaaaacgagc                                        30

<210> SEQ ID NO 54
<211> LENGTH: 36
<212> TYPE: DNA
<213> ORGANISM: Bacillus subtilis

<400> SEQUENCE: 54
aaaaatattt taaaaacgag caaaaatatt aaaaag                                 36

<210> SEQ ID NO 55
<211> LENGTH: 15
<212> TYPE: DNA
<213> ORGANISM: Bacillus subtilis

<400> SEQUENCE: 55
aaaaatatta aaaag                                                        15

<210> SEQ ID NO 56
<211> LENGTH: 24
<212> TYPE: DNA
<213> ORGANISM: Bacillus subtilis

<400> SEQUENCE: 56
ttattttata aaaatattaa aaag                                              24

<210> SEQ ID NO 57
<211> LENGTH: 15
<212> TYPE: DNA
<213> ORGANISM: Bacillus subtilis

<400> SEQUENCE: 57
aaaaaaaatg tgata                                                        15

<210> SEQ ID NO 58
<211> LENGTH: 24
<212> TYPE: DNA
<213> ORGANISM: Bacillus subtilis

<400> SEQUENCE: 58
aaaaaaaata aaaaaaatgt gata                                              24

<210> SEQ ID NO 59
<211> LENGTH: 15
<212> TYPE: DNA
<213> ORGANISM: Artificial Sequence
<220> FEATURE:
<223> OTHER INFORMATION: Consensus Sequence

<400> SEQUENCE: 59
aaaaawawtd wrawr                                                        15
```

<210> SEQ ID NO 60
<211> LENGTH: 24
<212> TYPE: DNA
<213> ORGANISM: Artificial Sequence
<220> FEATURE:
<223> OTHER INFORMATION: Consensus Sequence

<400> SEQUENCE: 60 wwwwwwmwa aaaawawtdw rawr                                               24

<210> SEQ ID NO 61
<211> LENGTH: 21
<212> TYPE: DNA
<213> ORGANISM: Bacillus licheniformis

<400> SEQUENCE: 61
caaaaatatt tttaattatg c                                                 21

<210> SEQ ID NO 62
<211> LENGTH: 58
<212> TYPE: PRT
<213> ORGANISM: Bacillus subtilis

<400> SEQUENCE: 62

Ala Cys Ala Gly Ala Ala Thr Ala Gly Thr Cys Thr Thr Thr Thr Ala
1               5                   10                  15

Ala Gly Thr Ala Ala Gly Thr Cys Thr Ala Cys Thr Cys Thr Gly Ala
            20                  25                  30

Ala Thr Thr Thr Thr Thr Thr Thr Ala Ala Ala Gly Gly Ala Gly
        35                  40                  45

Ala Gly Gly Gly Thr Ala Ala Ala Gly Ala
        50                  55

<210> SEQ ID NO 63
<211> LENGTH: 485
<212> TYPE: PRT
<213> ORGANISM: Cytophaga sp

<400> SEQUENCE: 63

Ala Ala Thr Asn Gly Thr Met Met Gln Tyr Phe Glu Trp Tyr Val Pro
1               5                   10                  15

Asn Asp Gly Gln Gln Trp Asn Arg Leu Arg Thr Asp Ala Pro Tyr Leu
            20                  25                  30

Ser Ser Val Gly Ile Thr Ala Val Trp Thr Pro Pro Ala Tyr Lys Gly
        35                  40                  45

Thr Ser Gln Ala Asp Val Gly Tyr Gly Pro Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Gly Glu Leu Lys Ser Ala Val Asn Thr Leu His Ser Asn Gly Ile Gln
                85                  90                  95

Val Tyr Gly Asp Val Val Met Asn His Lys Ala Gly Ala Asp Tyr Thr
            100                 105                 110

Glu Asn Val Thr Ala Val Glu Val Asn Pro Ser Asn Arg Asn Gln Glu
        115                 120                 125

Thr Ser Gly Glu Tyr Asn Ile Gln Ala Trp Thr Gly Phe Asn Phe Pro
    130                 135                 140

Gly Arg Gly Thr Thr Tyr Ser Asn Phe Lys Trp Gln Trp Phe His Phe

```
                145                 150                 155                 160
Asp Gly Thr Asp Trp Asp Gln Ser Arg Ser Leu Ser Arg Ile Phe Lys
                    165                 170                 175

Phe Arg Gly Thr Gly Lys Ala Trp Asp Trp Glu Val Ser Ser Glu Asn
                180                 185                 190

Gly Asn Tyr Asp Tyr Leu Met Tyr Ala Asp Ile Asp Tyr Asp His Pro
            195                 200                 205

Asp Val Val Asn Glu Met Lys Lys Trp Gly Val Trp Tyr Ala Asn Glu
210                 215                 220

Val Gly Leu Asp Gly Tyr Arg Leu Asp Ala Val Lys His Ile Lys Phe
225                 230                 235                 240

Ser Phe Leu Lys Asp Trp Val Asp Asn Ala Arg Ala Ala Thr Gly Lys
                245                 250                 255

Glu Met Phe Thr Val Gly Glu Tyr Trp Gln Asn Asp Leu Gly Ala Leu
            260                 265                 270

Asn Asn Tyr Leu Ala Lys Val Asn Tyr Asn Gln Ser Leu Phe Asp Ala
        275                 280                 285

Pro Leu His Tyr Asn Phe Tyr Ala Ala Ser Thr Gly Gly Gly Tyr Tyr
    290                 295                 300

Asp Met Arg Asn Ile Leu Asn Asn Thr Leu Val Ala Ser Asn Pro Thr
305                 310                 315                 320

Lys Ala Val Thr Leu Val Glu Asn His Asp Thr Gln Pro Gly Gln Ser
                325                 330                 335

Leu Glu Ser Thr Val Gln Pro Trp Phe Lys Pro Leu Ala Tyr Ala Phe
            340                 345                 350

Ile Leu Thr Arg Ser Gly Gly Tyr Pro Ser Val Phe Tyr Gly Asp Met
        355                 360                 365

Tyr Gly Thr Lys Gly Thr Thr Thr Arg Glu Ile Pro Ala Leu Lys Ser
    370                 375                 380

Lys Ile Glu Pro Leu Leu Lys Ala Arg Lys Asp Tyr Ala Tyr Gly Thr
385                 390                 395                 400

Gln Arg Asp Tyr Ile Asp Asn Pro Asp Val Ile Gly Trp Thr Arg Glu
                405                 410                 415

Gly Asp Ser Thr Lys Ala Lys Ser Gly Leu Ala Thr Val Ile Thr Asp
            420                 425                 430

Gly Pro Gly Gly Ser Lys Arg Met Tyr Val Gly Thr Ser Asn Ala Gly
        435                 440                 445

Glu Ile Trp Tyr Asp Leu Thr Gly Asn Arg Thr Asp Lys Ile Thr Ile
    450                 455                 460

Gly Ser Asp Gly Tyr Ala Thr Phe Pro Val Asn Gly Gly Ser Val Ser
465                 470                 475                 480

Val Trp Val Gln Gln
            485

<210> SEQ ID NO 64
<211> LENGTH: 483
<212> TYPE: PRT
<213> ORGANISM: Geobacillus stearothermophilus

<400> SEQUENCE: 64

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30
```

-continued

```
Leu Ser Ser Leu Gly Ile Thr Ala Leu Trp Leu Pro Pro Ala Tyr Lys
         35                  40                  45

Gly Thr Ser Arg Ser Asp Val Gly Tyr Gly Val Tyr Asp Leu Tyr Asp
 50                  55                  60

Leu Gly Glu Phe Asn Gln Lys Gly Thr Val Arg Thr Lys Tyr Gly Thr
 65                  70                  75                  80

Lys Ala Gln Tyr Leu Gln Ala Ile Gln Ala His Ala Ala Gly Met
                 85                  90                  95

Gln Val Tyr Ala Asp Val Val Phe Asp His Lys Gly Ala Asp Gly
             100                 105                 110

Thr Glu Trp Val Asp Ala Val Glu Val Asn Pro Ser Asp Arg Asn Gln
         115                 120                 125

Glu Ile Ser Gly Thr Tyr Gln Ile Gln Ala Trp Thr Lys Phe Asp Phe
 130                 135                 140

Pro Gly Arg Gly Asn Thr Tyr Ser Ser Phe Lys Trp Arg Trp Tyr His
 145                 150                 155                 160

Phe Asp Gly Val Asp Trp Asp Glu Ser Arg Lys Leu Ser Arg Ile Tyr
                 165                 170                 175

Lys Phe Arg Gly Ile Gly Lys Ala Trp Asp Trp Glu Val Asp Thr Glu
                 180                 185                 190

Asn Gly Asn Tyr Asp Tyr Leu Met Tyr Ala Asp Leu Asp Met Asp His
                 195                 200                 205

Pro Glu Val Val Thr Glu Leu Lys Asn Trp Gly Lys Trp Tyr Val Asn
             210                 215                 220

Thr Thr Asn Ile Asp Gly Phe Arg Leu Asp Ala Val Lys His Ile Lys
 225                 230                 235                 240

Phe Ser Phe Phe Pro Asp Trp Leu Ser Tyr Val Arg Ser Gln Thr Gly
                 245                 250                 255

Lys Pro Leu Phe Thr Val Gly Glu Tyr Trp Ser Tyr Asp Ile Asn Lys
             260                 265                 270

Leu His Asn Tyr Ile Thr Lys Thr Asp Gly Thr Met Ser Leu Phe Asp
         275                 280                 285

Ala Pro Leu His Asn Lys Phe Tyr Thr Ala Ser Lys Ser Gly Gly Ala
 290                 295                 300

Phe Asp Met Arg Thr Leu Met Thr Asn Thr Leu Met Lys Asp Gln Pro
 305                 310                 315                 320

Thr Leu Ala Val Thr Phe Val Asp Asn His Asp Thr Glu Pro Gly Gln
                 325                 330                 335

Ala Leu Gln Ser Trp Val Asp Pro Trp Phe Lys Pro Leu Ala Tyr Ala
             340                 345                 350

Phe Ile Leu Thr Arg Gln Glu Gly Tyr Pro Cys Val Phe Tyr Gly Asp
             355                 360                 365

Tyr Tyr Gly Ile Pro Gln Tyr Asn Ile Pro Ser Leu Lys Ser Lys Ile
         370                 375                 380

Asp Pro Leu Leu Ile Ala Arg Arg Asp Tyr Ala Tyr Gly Thr Gln His
 385                 390                 395                 400

Asp Tyr Leu Asp His Ser Asp Ile Ile Gly Trp Thr Arg Glu Gly Gly
                 405                 410                 415

Thr Glu Lys Pro Gly Ser Gly Leu Ala Ala Leu Ile Thr Asp Gly Pro
             420                 425                 430

Gly Gly Ser Lys Trp Met Tyr Val Gly Lys Gln His Ala Gly Lys Val
             435                 440                 445

Phe Tyr Asp Leu Thr Gly Asn Arg Ser Asp Thr Val Thr Ile Asn Ser
```

```
                450               455               460
Asp Gly Trp Gly Glu Phe Lys Val Asn Gly Gly Ser Val Ser Val Trp
465                 470               475               480

Val Pro Arg
```

<210> SEQ ID NO 65
<211> LENGTH: 94
<212> TYPE: DNA
<213> ORGANISM: Artificial Sequence
<220> FEATURE:
<223> OTHER INFORMATION: hybrid promoter

<400> SEQUENCE: 65

```
gtcgctgata aacagctgac atcaatatcc tatttttca aaaatatttt taaaagttgt    60
tgacttaaaa gaagctaaat gttatagtaa taaa                               94
```

<210> SEQ ID NO 66
<211> LENGTH: 95
<212> TYPE: DNA
<213> ORGANISM: Artificial Sequence
<220> FEATURE:
<223> OTHER INFORMATION: hybrid promoter

<400> SEQUENCE: 66

```
gtcgctgata aacagctgac atcaatatcc tatttttca aaaatatttt taaaagttg     60 ttgacttaaa agaagctaaa tgttatagta ataaa                              95
```

<210> SEQ ID NO 67
<211> LENGTH: 96
<212> TYPE: DNA
<213> ORGANISM: Artificial Sequence
<220> FEATURE:
<223> OTHER INFORMATION: hybrid promoter

<400> SEQUENCE: 67

```
gtcgctgata aacagctgac atcaatatcc tatttttca aaaatatttt taaaagttg     60 ttgcaatttt tagggaaac agatatactt aagtgt                              96
```

<210> SEQ ID NO 68
<211> LENGTH: 96
<212> TYPE: DNA
<213> ORGANISM: Artificial Sequence
<220> FEATURE:
<223> OTHER INFORMATION: hybrid promoter

<400> SEQUENCE: 68

```
gtcgctgata aacagctgac atcaatatcc tattttaaaa acttttcaa aaaagtgttg    60 ttgcaatttt tagggaaac agatatactt aagtgt                              96
```

<210> SEQ ID NO 69
<211> LENGTH: 95
<212> TYPE: DNA
<213> ORGANISM: Artificial Sequence
<220> FEATURE:
<223> OTHER INFORMATION: hybrid promoter

<400> SEQUENCE: 69

```
gtcgctgata aacagctgac atcaatatcc tatttttca aaaatatttt taaaagttg     60 ttgaaaagag ccgtgatcat gttataataa gacta                              95
```

<210> SEQ ID NO 70

-continued

```
<211> LENGTH: 50
<212> TYPE: DNA
<213> ORGANISM: Artificial Sequence
<220> FEATURE:
<223> OTHER INFORMATION: hybrid promoter

<400> SEQUENCE: 70
aaaaatatta aaagaaaag cttgactttg aagaagtgac attgtatact         50

<210> SEQ ID NO 71
<211> LENGTH: 222
<212> TYPE: DNA
<213> ORGANISM: Artificial Sequence
<220> FEATURE:
<223> OTHER INFORMATION: hybrid promoter

<400> SEQUENCE: 71
gtcgctgata acagctgac atcaatatcc tattttttca aaaaatattt taaaagttgt   60
tgacttaaaa gaagctaaat gttatagtaa taaaacagaa tagtcttta agtaagtcta  120 ctctgaattt tttaaaagg agagggtaaa gaaagccgcc aggaaaaact tgtctgaata  180
gtacggttgc aattttagg ggaaacagat atacttaagt gt                   222

<210> SEQ ID NO 72
<211> LENGTH: 179
<212> TYPE: DNA
<213> ORGANISM: Artificial Sequence
<220> FEATURE:
<223> OTHER INFORMATION: hybrid promoter

<400> SEQUENCE: 72
aaaaaaaatg tgatataaaa gttgactttg aagaagtgac attgtatact aataaagtac   60
agaatagtct tttaagtaag tctactctga attttttaa aaggagaggg taaagaaagc  120
cgccaggaaa aacttgtctg aatagtacgg ttgcaatttt tagggggaaac agatatact  179

<210> SEQ ID NO 73
<211> LENGTH: 199
<212> TYPE: DNA
<213> ORGANISM: Artificial Sequence
<220> FEATURE:
<223> OTHER INFORMATION: hybrid promoter

<400> SEQUENCE: 73
aacgtcgctg atgaacagcg tgaaacaaaa cagaaaaaca aaaagttttt cctaaatcct   60
attttttcaa aaaatatttt aaaaaggtgt ttacaagatt ttaaaaatgt gtataataag  120
aaaagtcgaa ttgaaaaaga ttcgaaaaaa cattaaaaaa cttcttgact tcaacatcaa  180
atgatagtat gatagttaa                                            199

<210> SEQ ID NO 74
<211> LENGTH: 165
<212> TYPE: DNA
<213> ORGANISM: Artificial Sequence
<220> FEATURE:
<223> OTHER INFORMATION: hybrid promoter

<400> SEQUENCE: 74
ctgcgctttt ttgtgtcata acctttaca gtcataaaaa ttatggtata atcatttctg   60
ttgtcttttt aaagacacaa gcatgaccat tatgactagt aaaaactttt tcaaaaaagt  120
ataattgaca tgtattgaat gatatagaat aattggttta tatta                165
```

<210> SEQ ID NO 75
<211> LENGTH: 121
<212> TYPE: DNA
<213> ORGANISM: Artificial Sequence
<220> FEATURE:
<223> OTHER INFORMATION: hybrid promoter

<400> SEQUENCE: 75
gtcgctgata aacagctgac atcaatgttt ttttatccca atattacaaa aatattttta        60
attatgcagg aaaacaaaaa aagttgttga cttaaaagaa gctaaatgtt atagtaataa       120
a                                                                      121

<210> SEQ ID NO 76
<211> LENGTH: 224
<212> TYPE: DNA
<213> ORGANISM: Artificial Sequence
<220> FEATURE:
<223> OTHER INFORMATION: hybrid promoter

<400> SEQUENCE: 76
tgttttttta tcccaatatt acaaaaatat tttaattat gcaggaaaac aaaaaaagtt         60
gttgacgaca tcacgattaa atgttaagat attataacag aatagtcttt taagtaagtc       120
tactctgaat ttttttaaaa ggagagggta agaaagccg ccaggaaaaa cttgtctgaa        180
tagtacggtt gcaattttta ggggaaacag atatacttaa gtgt                       224

<210> SEQ ID NO 77
<211> LENGTH: 223
<212> TYPE: DNA
<213> ORGANISM: Artificial Sequence
<220> FEATURE:
<223> OTHER INFORMATION: hybrid promoter

<400> SEQUENCE: 77
gtcgctgata aacagctgac atcaatatcc tatttttca aaaatatttt taaaaagttg         60
ttgacgacat cacgattaaa tgttaagata ttataacaga atagtctttt aagtaagtct      120
actctgaatt ttttaaaag gagagggtaa agaaagccgc caggaaaaac ttgtctgaat       180
agtacggttg caatttttag gggaaacaga tatacttaag tgt                        223

<210> SEQ ID NO 78
<211> LENGTH: 250
<212> TYPE: DNA
<213> ORGANISM: Artificial Sequence
<220> FEATURE:
<223> OTHER INFORMATION: hybrid promoter

<400> SEQUENCE: 78
gtcgctgata aacagctgac atcaatgttt ttttatccca atattacaaa aatattttta        60
attatgcagg aaaacaaaaa aagttattga caaatacgtg agcttgatgt tatattatta      120
aaacagaata gtcttttaag taagtctact ctgaatttt ttaaaaggag agggtaaga       180 aagccgccag gaaaaacttg tctgaatagt acggttgcaa tttttagggg aaacagatat      240
acttaagtgt                                                             250

<210> SEQ ID NO 79
<211> LENGTH: 224
<212> TYPE: DNA
<213> ORGANISM: Artificial Sequence
<220> FEATURE:
<223> OTHER INFORMATION: hybrid promoter

<400> SEQUENCE: 79

```
gtcgctgata aacagctgac atcaatatcc tattttttca aaaatatttt taaaaagtta    60
ttgacaaata cgtgagcttg atgttatatt attaaaacag aatagtcttt taagtaagtc   120
tactctgaat ttttttaaaa ggagagggta aagaaagccg ccaggaaaaa cttgtctgaa   180
tagtacggtt gcaatttttta ggggaaacag atatacttaa gtgt                  224
```

<210> SEQ ID NO 80
<211> LENGTH: 226
<212> TYPE: DNA
<213> ORGANISM: Artificial Sequence
<220> FEATURE:
<223> OTHER INFORMATION: hybrid promoter

<400> SEQUENCE: 80

```
gtcgctgata aacagctgac atcaatatcc tattttttca aaaatatttt taaaaagttg    60
ttgacttaaa agaagctaaa tgttatagta ataaaacaga atagtcttt aagtaagtct   120
actctgaatt ttttaaaag gagagggtaa agagcttttc ttttggaaga aaatataggg   180
aaaatggtac ttgttaaaaa ttcggaatat ttatacaata tcatat                 226
```

<210> SEQ ID NO 81
<211> LENGTH: 1298
<212> TYPE: DNA
<213> ORGANISM: Artificial Sequence
<220> FEATURE:
<223> OTHER INFORMATION: Hybrid promoter 1 operably linked to a GOI

<400> SEQUENCE: 81

```
gtcgctgata aacagctgac atcaatatcc tattttttca aaaatatttt taaaagttgt    60
tgacttaaaa gaagctaaat gttatagtaa taaaacagaa tagtcttta agtaagtcta   120
ctctgaattt ttttaaaagg agagggtaaa gagtgagaag caaaaaattg tggatcagct   180
tgttgtttgc gttaacgtta atctttacga tggcgttcag caacatgagc gcgcaggcgg   240
cagggaaatc aaacggggaa aagaaatata ttgtcgggtt taaacagaca atgagcacga   300
tgagcgccgc taagaagaaa gatgtcattt ctgaaaaagg cgggaaagtg caaaagcaat   360
tcaaatatgt agacgcagct tcagctacat taaacgaaaa agctgtaaaa gaattgaaaa   420
aagacccgag cgtcgcttac gttgaagaag atcacgtagc acatgcgtac gcgcagtccg   480
tgccttacgg cgtatcacaa attaaagccc ctgctctgca ctctcaaggc tacactggat   540
caaatgttaa agtagcggtt atcgacagcg gtatcgattc ttctcatcct gatttaaagg   600
tagcaggcgg agccagcatg gttccttctg aaacaaatcc tttccaagac aacaactctc   660
acggaactca cgttgccggc acagttgcgc tcttaataa ctcaatcggt gtattaggcg   720
ttgcgccaag cgcatcactt tacgctgtaa aagttctcgg tgctgacggt tccggccaat   780
acagctggat cattaacgga atcgagtggg cgatcgcaaa caatatggac gttattaaca   840
tgagcctcgg cggaccttct ggttctgctg ctttaaaagc ggcagttgat aaagccgttg   900
catccggcgt cgtagtcgtt gcggcagccg gtaacgaagg cacttccggc agctcaagca   960
cagtgggcta ccctggtaaa tacccttctg tcattgcagt aggcgctgtt gacagcagca  1020
accaaagagc atctttctca agcgtaggac ctgagcttga tgtcatggca cctggcgtat  1080
ctatccaaag cacgcttcct ggaaacaaat acggcgcgtt gaacggtaca tcaatggcat  1140
ctccgcacgt tgccggagcg gctgctttga ttcttttctaa gcacccgaac tggacaaaca  1200
ctcaagtccg cagcagttta gaaaacacca ctacaaaact tggtgattct ttctactatg  1260
```

```
gaaaagggct gatcaacgta caggcggcag ctcagtaa                              1298
```

<210> SEQ ID NO 82
<211> LENGTH: 1402
<212> TYPE: DNA
<213> ORGANISM: Artificial Sequence
<220> FEATURE:
<223> OTHER INFORMATION: hybrid promoter 7 operably linked to a GOI

<400> SEQUENCE: 82

```
atcctatttt ttcaaaaaat attttaaaag ttgttgactt aaaagaagct aaatgttata      60
gtaataaaac agaatagtct tttaagtaag tctactctga attttttttaa aaggagaggg    120
taaagaaagc cgccaggaaa aacttgtctg aatagtacgg ttgcaatttt taggggaaac    180
agatatactt aagtgtacag aatatctttt aagtaagtct actctgaatt tttttaaaag    240
gagagggtaa agagtgagaa gcaaaaaatt gtggatcagt ttgctgtttg ctttagcgtt    300
aatctttacg atggcgttcg gcagcacatc ctctgcccag gcggcaggga aatcaaacgg    360
ggaaaagaaa tatattgtcg ggtttaaaca gacaatgagc acgatgagcg ccgctaagaa    420
gaaagatgtc atttctgaaa aaggcgggaa agtgcaaaag caattcaaat atgtagacgc    480
agcttcagct acattaaacg aaaaagctgt aaaagaattg aaaaaagacc cgagcgtcgc    540
ttacgttgaa gaagatcacg tagcacatgc gtacgcgcag tccgtgcctt acggcgtatc    600
acaaattaaa gcccctgctc tgcactctca aggctacact ggatcaaatg ttaaagtagc    660
ggttatcgac agcggtatcg attcttctca tcctgattta aaggtagcag gcggagccag    720
catggttcct tctgaaacaa atcctttcca agacaacaac tctcacggaa ctcacgttgc    780
cggcacagtt gcggctctta ataactcaat cggtgtatta ggcgttgcgc caagcgcatc    840
actttacgct gtaaaagttc tcggtgctga cggttccggc aatacagct ggatcattaa     900
cggaatcgag tgggcgatcg caaacaatat ggacgttatt aacatgagcc tcggcggacc    960
ttctggttct gctgctttaa agcggcagt tgataaagcc gttgcatccg gcgtcgtagt    1020
cgttgcggca gccggtaacg aaggcactc cggcagctca agcacagtgg gctaccctgg    1080
taaatacccct tctgtcattg cagtaggcgc tgttgacagc agcaaccaaa gagcatcttt    1140
ctcaagcgta ggacctgagc ttgatgtcat ggcacctggc gtatctatcc aaagcacgct    1200
tcctggaaac aaatacggcg cgttgaacgg tacatcaatg gcatctccgc acgttgccgg    1260
agcggctgct ttgattcttt ctaagcaccc gaactggaca aacactcaag tccgcagcag    1320
tttagaaaac accactacaa aacttggtga ttctttctac tatggaaaag ggctgatcaa    1380
cgtacaggcg gcagctcagt aa                                             1402
```

<210> SEQ ID NO 83
<211> LENGTH: 87
<212> TYPE: DNA
<213> ORGANISM: Bacillus licheniformis

<400> SEQUENCE: 83

```
atgaaacaac aaaaacggct ttacgcccga ttgctgacgc tgttatttgc gctcatcttc      60
ttgctgcctc attctgcagc tagcgca                                          87
```

<210> SEQ ID NO 84
<211> LENGTH: 34
<212> TYPE: DNA
<213> ORGANISM: Bacillus licheniformis

<400> SEQUENCE: 84
cggatttcct gaaggaaatc cgttttttta tttt                               34

<210> SEQ ID NO 85
<211> LENGTH: 58
<212> TYPE: DNA
<213> ORGANISM: Bacillus subtilis

<400> SEQUENCE: 85 gcgcttttttt gtgtcataac cctttacagt cataaaaatt atggtataat catttctg   58

<210> SEQ ID NO 86
<211> LENGTH: 992
<212> TYPE: DNA
<213> ORGANISM: Artificial Sequence
<220> FEATURE:
<223> OTHER INFORMATION: Spectinomycine Resistance Marker

<400> SEQUENCE: 86
ctagacatat gcaagggttt attgttttct aaaatctgat taccaattag aatgaatatt    60
tcccaaatat taaataataa aacaaaaaaa ttgaaaaaag tgtttccacc attttttcaa   120 ttttttttata attttttttaa tctgttattt aaatagttta tagttaaatt tacatttca   180 ttagtccatt caatattctc tccaagataa ctacgaactg ctaacaaaat tctctcccta   240
tgttctaatg gagaagattc agccactgca tttcccgcaa tatctttttgg tatgatttta   300 cccgtgtcca tagttaaaat catacggcat aaagttaata tagagttggt ttcatcatcc   360
tgataattat ctattaattc ctctgacgaa tccataatgg ctcttctcac atcagaaaat   420
ggaatatcag gtagtaattc ctctaagtca taatttccgt atattctttt attttttcgt   480
tttgcttggt aaagcattat ggttaaatct gaatttaatt ccttctgagg aatgtatcct   540
tgttcataaa gctcttgtaa ccattctcca taaataaatt cttgtttggg aggatgattc   600
cacggtacca tttcttgctg aataataatt gttaattcaa tatatcgtaa gttgcttttta  660 tctcctatttt ttttttgaaat aggtctaatt ttttgtataa gtatttctttt actttgatct  720 gtcaatggtt cagatacgac gactaaaaag tcaagatcac tatttggttt tagtccactc    780
tcaactcctg atccaaacat gtaagtacca ataaggttat ttttttaaatg tttccgaagt   840 atttttttca cttttattaat ttgttcgtat gtattcaaat atatcctcct cactattttg   900
attagtacct attttatatc catagttgtt aattaaaataa acttaattta gtttattttat  960 agatttcatt ggcttctaaa tttttttatct ag                               992

<210> SEQ ID NO 87
<211> LENGTH: 900
<212> TYPE: DNA
<213> ORGANISM: Bacillus subtilis

<400> SEQUENCE: 87
gcaaaacgcg gatcattgga agagacgacc gtacccgcag catcaatgcc taaaataagc    60
ggatactctc tgacgatatt gcctcctgct tttccggcca gaccatcttt gtaattaatg   120
ccggaataag caactttaat caggacacca tccttcggca aatcctctgt tgatatggtt   180
ttcacatgga ctgaaacatc atcggcattt ttttctgcct gcaaggcttg aaataacgtt   240
gacattcggc acactccttt tcatttatat cgtaaccgaa gaacgttcaa aaaaccaaat   300
catcaagccg ccattttcac ttcgccggca cattgagaca ataatggaca aatccggtat   360
cctcttcata gccgttttgc tcatacaagc ttcttgcctt ccggttgtgg tgctcagtct   420

```
gaagtgttaa acattttgcc ccgttttgcc ctgcataatc ctttgcggca gaaagcagcc    480
ggccgccggc tcccttttgta cgcgcatgag gaacgacaaa taagtcattt aatatgtata    540
tccttttcat tgacacagaa gaaaacgttg gatagagctg ggtaaagcct atgaattctc    600
cattttcttc tgctatcaaa ataacagact cgtgattttc caaacgagct ttcaaaaaag    660
cctctgcccc ttgcaaatcg gatgcctgtc tataaaattc ccgatattgg ttaaacagcg    720
gcgcaatggc ggccgcatct gatgtctttg cttggcgaat gttcatctta tttcttcctc    780
cctctcaata atttttttcat tctatccctt ttctgtaaag tttattttc agaatacttt    840 tatcatcatg ctttgaaaaa atatcacgat aatatccatt gttctcacgg aagcacacgc    900
```

<210> SEQ ID NO 88
<211> LENGTH: 934
<212> TYPE: DNA
<213> ORGANISM: Bacillus subtilis

<400> SEQUENCE: 88

```
tagtaaaaag aagcaggttc ctccatacct gcttcttttt atttgtcagc atcctgatgt     60
tccggcgcat tctcttcttt ctccgcatgt tgaatccgtt ccatgatcga cggatggctg    120
cctctgaaaa tcttcacaag caccggagga tcaacctggc tcagcccgt cacggccaaa    180 tcctgaaacg tttaacagc ggcttctctg ttctctgtca actcgatccc atactggtca    240
gccttattct cctgataacg cgagacagca ttagaaaaag gcgtaaccgc aaagctcaaa    300
acagaaaaca aaagcaataa cagcggaagt gccgcaagat catgccgccc ttctaaatga    360
aacatgctgc gggttaggcg aaccgtccgc ttgtaaagct tatcaatgac ataaaatccg    420
gcgagcgaca cgagcaaata gccagccaga ccgatgtaaa cgtgcttcat gacataatgg    480
cccatttcgt ggcccataat aaacagaatt tctgaatcgt caagtttgtt cagcgtcgta    540
tcccacaata caatccgttt attggcccca attcctgtaa cataggcatt cagcgcattt    600 gtttttctg acatgttcac ttcatataca tggtcagccg gaatattggc ttcatctgcc    660
agctctaaaa ttttgctttc aagctctttg tttttcagcg gataaaaatc attgtataaa    720
ggatcgataa tgaccggctg aataaaaaac agaaacagcg aaaacggcac tgttaacagc    780
caggcgtata accaccattt tttttcatgc cttttgatca gccaataaaa acgagaacg    840 caaagcgtaa agattggaaa gctgatccaa aagctgataa cctgatcctt agcccagctg    900
gccgttgtct gtgtggaaat gttatagtca agcg                                934
```

<210> SEQ ID NO 89
<211> LENGTH: 57
<212> TYPE: DNA
<213> ORGANISM: Bacillus subtilis

<400> SEQUENCE: 89

```
taaaaacttt ttcaaaaaag tattgaccta gttaactaaa aatgttacta ttaagta       57
```

<210> SEQ ID NO 90
<211> LENGTH: 250
<212> TYPE: DNA
<213> ORGANISM: Artificial Sequence
<220> FEATURE:
<223> OTHER INFORMATION: hybrid promoter

<400> SEQUENCE: 90

```
gtcgctgata aacagctgac atcaatgttt ttttatccca atattacaaa aatatttta     60
```

```
attatgcagg aaaacaaaaa aagttattga caaatacgtg agcttgatgt tatattatta    120
aaacagaata gtcttttaag taagtctact ctgaattttt ttaaaaggag agggtaaaga    180
aagccgccag gaaaaacttg tctgaatagt acggttgcaa ttttttaggggg aaacagatat  240 acttaagtgt                                                            250
```

<210> SEQ ID NO 91
<211> LENGTH: 249
<212> TYPE: DNA
<213> ORGANISM: Artificial Sequence
<220> FEATURE:
<223> OTHER INFORMATION: hybrid promoter

<400> SEQUENCE: 91

```
gtcgctgata aacagctgac atcaatgttt ttttatccca atattacaaa aatatttta     60 attatgcagg aaaacaaaaa aagttgttga cgacatcacg attaaatgtt aagatattat    120
aacagaatag tcttttaagt aagtctactc tgaattttt taaaaggaga gggtaaagaa     180
agccgccagg aaaaacttgt ctgaatagta cggttgcaat tttagggga aacagatata    240 cttaagtgt                                                             249
```

<210> SEQ ID NO 92
<211> LENGTH: 224
<212> TYPE: DNA
<213> ORGANISM: Artificial Sequence
<220> FEATURE:
<223> OTHER INFORMATION: hybrid promoter

<400> SEQUENCE: 92

```
gtcgctgata aacagctgac atcaatatcc tattttttca aaaatatttt taaaaagtta   60
ttgacaaata cgtgagcttg atgttatatt attaaaacag aatagtcttt taagtaagtc   120
tactctgaat ttttttaaaa ggagagggta agaaagccg ccaggaaaaa cttgtctgaa    180
tagtacggtt gcaattttta ggggaaacag atatacttaa gtgt                    224
```

<210> SEQ ID NO 93
<211> LENGTH: 223
<212> TYPE: DNA
<213> ORGANISM: Artificial Sequence
<220> FEATURE:
<223> OTHER INFORMATION: hybrid promoter

<400> SEQUENCE: 93

```
gtcgctgata aacagctgac atcaatatcc tattttttca aaaatatttt taaaagttg    60 ttgacttaaa agaagctaaa tgttatagta ataaaacaga atagtctttt aagtaagtct   120
actctgaatt ttttaaaag gagagggtaa agaaagccgc caggaaaaac ttgtctgaat    180
agtacggttg caattttag gggaaacaga tatacttaag tgt                      223
```

<210> SEQ ID NO 94
<211> LENGTH: 231
<212> TYPE: DNA
<213> ORGANISM: Artificial Sequence
<220> FEATURE:
<223> OTHER INFORMATION: hybrid promoter

<400> SEQUENCE: 94

```
agctcgtcgc tgataaacag ctgacatcaa tatcctattt tttcaaaaaa tattttaaaa   60
agttgttgac ttaaaagaag ctaaatgtta tagtaataaa acagaatagt cttttaagta   120
agtctactct gaattttttt aaaaggagag ggtaaagagc ttttctttg gaagaaaata    180
```

-continued tagggaaaat ggtacttgtt aaaaattcgg aatatttata caatatcata t        231

<210> SEQ ID NO 95
<211> LENGTH: 231
<212> TYPE: DNA
<213> ORGANISM: Artificial Sequence
<220> FEATURE:
<223> OTHER INFORMATION: hybrid promoter

<400> SEQUENCE: 95
agctcgtcgc tgataaacag ctgacatcaa tatcctattt tttcaaaaaa tattttaaaa        60
agttgttgac ttaaaagaag ctaaatgtta tagtaataaa acagaatagt cttttaagta        120
agtctactct gaatttttt aaaggagag ggtaaagagc ttttcttttg gaagaaaata        180
tagggaaaat ggtacttgtt aaaaattcgg aatatttata caatatcata t        231

<210> SEQ ID NO 96
<211> LENGTH: 153
<212> TYPE: DNA
<213> ORGANISM: Artificial Sequence
<220> FEATURE:
<223> OTHER INFORMATION: hybrid promoter

<400> SEQUENCE: 96
gtcgctgata aacagctgac atcaatatcc tattttttca aaaatatttt taaaagttg        60 ttgacttaaa agaagctaaa tgttatagta ataaaacaga atagtctttt aagtaagtct        120
actctgaatt ttttaaaag gagagggtaa aga        153

<210> SEQ ID NO 97
<211> LENGTH: 121
<212> TYPE: DNA
<213> ORGANISM: Artificial Sequence
<220> FEATURE:
<223> OTHER INFORMATION: hybrid promoter

<400> SEQUENCE: 97
gtcgctgata aacagctgac atcaatgttt ttttatccca atattacaaa aatatttta        60 attatgcagg aaaacaaaaa aagttgttga cttaaaagaa gctaaatgtt atagtaataa        120
a        121

<210> SEQ ID NO 98
<211> LENGTH: 39
<212> TYPE: DNA
<213> ORGANISM: Bacillus licheniformis

<400> SEQUENCE: 98
gttgttgacg acatcacgat taaatgttaa gatattata        39

<210> SEQ ID NO 99
<211> LENGTH: 40
<212> TYPE: DNA
<213> ORGANISM: Bacillus licheniformis

<400> SEQUENCE: 99
gttattgaca aatacgtgag cttgatgtta tattattaaa        40

<210> SEQ ID NO 100
<211> LENGTH: 65
<212> TYPE: DNA
<213> ORGANISM: Bacillus subtilis

```
<400> SEQUENCE: 100
aaaagttttt aaaaaagttg ttgactttga agaagtgacg ttgtatacta ataaagttgc     60
tttaa                                                                 65

<210> SEQ ID NO 101
<211> LENGTH: 154
<212> TYPE: DNA
<213> ORGANISM: Bacillus licheniformis

<400> SEQUENCE: 101
tcgcttataa aagcaacaac aaaaactttt tcaaaaaaag tattgaccgc ttgtcttata     60
aatgttatat ttaagtgtcg cttataaaag caacaacaaa acttttttt aaaaaagtat    120 tgaccgcttg tcttataaat gttatattta agtg                                154

<210> SEQ ID NO 102
<211> LENGTH: 141
<212> TYPE: DNA
<213> ORGANISM: Bacillus licheniformis

<400> SEQUENCE: 102
tcgctaatga cgaataattt tttgaaaaaa gttgttgacg acatcacgat taaatgttaa     60
gatattatat cgctaatgac gaataatttt tttgaaaaaa gttgttgac gacatcacga    120 ttaaatgtta agatattata g                                              141

<210> SEQ ID NO 103
<211> LENGTH: 193
<212> TYPE: DNA
<213> ORGANISM: Bacillus licheniformis

<400> SEQUENCE: 103
tcgctgttag cggaacggtt tttgaacaga aagcagcagc gacgaaaaat caaaaaaaca     60
tttgacactt ctcgttgaaa atgttatact aataaatcgc tgttagcgga acggttttg    120 aacagaaagc agcagcgacg aaaaatcaaa aaacatttg acacttctcg ttgaaaatgt    180
tatactaata aag                                                       193

<210> SEQ ID NO 104
<211> LENGTH: 167
<212> TYPE: DNA
<213> ORGANISM: Bacillus licheniformis

<400> SEQUENCE: 104
ttgccgcaaa acggcggcga agaaaaaaaa gaacttcaaa aaagttctt gacttaatat     60 ctgagattgg atataatata aaattgccgc aaaacggcgg cgaaagaaaa aaagaacttc    120 aaaaaagtt cttgacttaa tatctgagat tggatataat ataaaag                   167

<210> SEQ ID NO 105
<211> LENGTH: 185
<212> TYPE: DNA
<213> ORGANISM: Bacillus licheniformis

<400> SEQUENCE: 105
tcgctgataa acagctgaca tgaaaaagct ccaaaaaata attttgagaa aagttattga     60
caaatacgtg agcttgatgt tatattatta atcgctgat aaacagctga catgaaaaag    120
ctccaaaaaa aatttgag aaaagttatt gacaaatatg tgagcttgat gttatattat    180
taaag                                                                185
```

-continued

<210> SEQ ID NO 106
<211> LENGTH: 57
<212> TYPE: DNA
<213> ORGANISM: Bacillus licheniformis

<400> SEQUENCE: 106
aaaaactttt tttaaaaaag tattgaccgc ttgtcttata aatgttatat ttaagtg        57

<210> SEQ ID NO 107
<211> LENGTH: 59
<212> TYPE: DNA
<213> ORGANISM: Bacillus licheniformis

<400> SEQUENCE: 107
tttatcgcaa tataattttt tgttgacaaa tatatttaaa ggtgttaaat taatatttg     59

<210> SEQ ID NO 108
<211> LENGTH: 57
<212> TYPE: DNA
<213> ORGANISM: Bacillus licheniformis

<400> SEQUENCE: 108 taatttttt gaaaaaagt tgttgacgac atcacgatta aatgttaaga tattata         57

<210> SEQ ID NO 109
<211> LENGTH: 118
<212> TYPE: DNA
<213> ORGANISM: Bacillus licheniformis

<400> SEQUENCE: 109
cagaaaaact tcaaaaaact tcttgacttt aactgatatt catagtatta tagttaagat   60
tcaatctttc aaatataatc ttttcatcag gaacataatg tgctataatt tctcttgg    118

<210> SEQ ID NO 110
<211> LENGTH: 59
<212> TYPE: DNA
<213> ORGANISM: Bacillus licheniformis

<400> SEQUENCE: 110
ggatatttta ttaaaaaag tgttgacact aatttataac ggtgatatat tattaagcg    59

<210> SEQ ID NO 111
<211> LENGTH: 58
<212> TYPE: DNA
<213> ORGANISM: Bacillus licheniformis

<400> SEQUENCE: 111
cgacgaaaaa tcaaaaaac atttgacact tctcgttgaa aatgttatac taataaag      58

<210> SEQ ID NO 112
<211> LENGTH: 59
<212> TYPE: DNA
<213> ORGANISM: Bacillus licheniformis

<400> SEQUENCE: 112 taaattttt ctcaaaaaag tattgcacaa tcataaatac ggtggtatat tattattcg    59

<210> SEQ ID NO 113
<211> LENGTH: 58
<212> TYPE: DNA
<213> ORGANISM: Bacillus licheniformis

<400> SEQUENCE: 113
aaaagaactt caaaaaaagt tcttgactta atatctgaga ttggatataa tataaaag    58

<210> SEQ ID NO 114
<211> LENGTH: 60
<212> TYPE: DNA
<213> ORGANISM: Bacillus licheniformis

<400> SEQUENCE: 114
aagaaaaaaa ttaaaaagag ggttgaccgg aattaaataa acatgttata ttgttattcg    60

<210> SEQ ID NO 115
<211> LENGTH: 59
<212> TYPE: DNA
<213> ORGANISM: Bacillus licheniformis

<400> SEQUENCE: 115
aaaataattt tgagaaaagt tattgacaaa tatgtgagct tgatgttata ttattaaag    59

<210> SEQ ID NO 116
<211> LENGTH: 73
<212> TYPE: DNA
<213> ORGANISM: Bacillus licheniformis

<400> SEQUENCE: 116
gcttttcttt tggaagaaaa tatagggaaa atggtacttg ttaaaaattc ggaatattta    60
tacaatatca tat    73

<210> SEQ ID NO 117
<211> LENGTH: 53
<212> TYPE: DNA
<213> ORGANISM: Bacillus subtilis

<400> SEQUENCE: 117
aaaaaaaatg tgatataaaa gaggatatac ataggatata acgaatattt tca    53

<210> SEQ ID NO 118
<211> LENGTH: 60
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (6)..(25)
<223> OTHER INFORMATION: n is a, c, g, or t
<220> FEATURE:
<221> NAME/KEY: misc_feature
<222> LOCATION: (38)..(54)
<223> OTHER INFORMATION: n is a, c, g, or t

<400> SEQUENCE: 118
ttgacnnnnn nnnnnnnnnn nnnnntatat tttttcannn nnnnnnnnnn nnnntataat    60

<210> SEQ ID NO 119
<211> LENGTH: 60
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (6)..(25)
<223> OTHER INFORMATION: n is a, c, g, or t
<220> FEATURE:
<221> NAME/KEY: misc_feature
<222> LOCATION: (38)..(54)
<223> OTHER INFORMATION: n is a, c, g, or t

<400> SEQUENCE: 119
ttgacnnnnn nnnnnnnnnn nnnntaaat tttgacannn nnnnnnnnnn nnnntaaatt      60

<210> SEQ ID NO 120
<211> LENGTH: 29
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (7)..(23)
<223> OTHER INFORMATION: n is a, c, g, or t

<400> SEQUENCE: 120
ttgacgnnnn nnnnnnnnnn nnntaagat                                       29

<210> SEQ ID NO 121
<211> LENGTH: 32
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (6)..(25)
<223> OTHER INFORMATION: n is a, c, g, or t

<400> SEQUENCE: 121
ttgacnnnnn nnnnnnnnnn nnnnntatat at                                   32

<210> SEQ ID NO 122
<211> LENGTH: 60
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (6)..(25)
<223> OTHER INFORMATION: n is a, c, g, or t
<220> FEATURE:
<221> NAME/KEY: misc_feature
<222> LOCATION: (38)..(54)
<223> OTHER INFORMATION: n is a, c, g, or t

<400> SEQUENCE: 122
ttgacnnnnn nnnnnnnnnn nnnntatat tttgacannn nnnnnnnnnn nnnntatatt      60

<210> SEQ ID NO 123
<211> LENGTH: 60
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (6)..(25)
<223> OTHER INFORMATION: n is a, c, g, or t
<220> FEATURE:
<221> NAME/KEY: misc_feature
<222> LOCATION: (38)..(54)
<223> OTHER INFORMATION: n is a, c, g, or t

<400> SEQUENCE: 123
ttgacnnnnn nnnnnnnnnn nnnntatac tttgacannn nnnnnnnnnn nnnntatact      60

<210> SEQ ID NO 124
<211> LENGTH: 60
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (6)..(25)
<223> OTHER INFORMATION: n is a, c, g, or t
<220> FEATURE:
<221> NAME/KEY: misc_feature
<222> LOCATION: (38)..(54)
<223> OTHER INFORMATION: n is a, c, g, or t

<400> SEQUENCE: 124
ttgcannnnn nnnnnnnnnn nnnntatat tttgcacnnn nnnnnnnnnn nnnntatatt    60

<210> SEQ ID NO 125
<211> LENGTH: 32
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (7)..(26)
<223> OTHER INFORMATION: n is a, c, g, or t

<400> SEQUENCE: 125
ttgactnnnn nnnnnnnnnn nnnnnntata at                                 32

<210> SEQ ID NO 126
<211> LENGTH: 60
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (6)..(25)
<223> OTHER INFORMATION: n is a, c, g, or t
<220> FEATURE:
<221> NAME/KEY: misc_feature
<222> LOCATION: (38)..(54)
<223> OTHER INFORMATION: n is a, c, g, or t

<400> SEQUENCE: 126
ttgacnnnnn nnnnnnnnnn nnnntatat tttgaccnnn nnnnnnnnnn nnnnttatat    60

<210> SEQ ID NO 127
<211> LENGTH: 60
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (6)..(25)
<223> OTHER INFORMATION: n is a, c, g, or t
<220> FEATURE:
<221> NAME/KEY: misc_feature
<222> LOCATION: (38)..(54)
<223> OTHER INFORMATION: n is a, c, g, or t

<400> SEQUENCE: 127
ttgacnnnnn nnnnnnnnnn nnnntatat tttgacannn nnnnnnnnnn nnnnttatat    60

<210> SEQ ID NO 128
<211> LENGTH: 28

```
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (6)..(22)
<223> OTHER INFORMATION: n is a, c, g, or t

<400> SEQUENCE: 128
tttacnnnnn nnnnnnnnnn nntataat                                            28

<210> SEQ ID NO 129
<211> LENGTH: 29
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (6)..(23)
<223> OTHER INFORMATION: n is a, c, g, or t

<400> SEQUENCE: 129
ttgacnnnnn nnnnnnnnnn nnntactat                                           29

<210> SEQ ID NO 130
<211> LENGTH: 29
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (6)..(23)
<223> OTHER INFORMATION: n is a, c, g, or t

<400> SEQUENCE: 130
ttgacnnnnn nnnnnnnnnn nnntattct                                           29

<210> SEQ ID NO 131
<211> LENGTH: 29
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (6)..(23)
<223> OTHER INFORMATION: n is a, c, g, or t

<400> SEQUENCE: 131
ttgacnnnnn nnnnnnnnnn nnntatgat                                           29

<210> SEQ ID NO 132
<211> LENGTH: 29
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (6)..(23)
<223> OTHER INFORMATION: n is a, c, g, or t

<400> SEQUENCE: 132
ttgcannnnn nnnnnnnnnn nnntatatt                                           29

<210> SEQ ID NO 133
```

```
<211> LENGTH: 29
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (6)..(23)
<223> OTHER INFORMATION: n is a, c, g, or t

<400> SEQUENCE: 133
ttgacnnnnn nnnnnnnnnn nnntataat                                29

<210> SEQ ID NO 134
<211> LENGTH: 29
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (6)..(23)
<223> OTHER INFORMATION: n is a, c, g, or t

<400> SEQUENCE: 134
ttgacnnnnn nnnnnnnnnn nnntatagt                                29

<210> SEQ ID NO 135
<211> LENGTH: 28
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (6)..(22)
<223> OTHER INFORMATION: n is a, c, g, or t

<400> SEQUENCE: 135
tttacnnnnn nnnnnnnnnn nntataat                                 28

<210> SEQ ID NO 136
<211> LENGTH: 28
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (6)..(22)
<223> OTHER INFORMATION: n is a, c, g, or t

<400> SEQUENCE: 136
ttgacnnnnn nnnnnnnnnn nntatgat                                 28

<210> SEQ ID NO 137
<211> LENGTH: 29
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (6)..(23)
<223> OTHER INFORMATION: n is a, c, g, or t

<400> SEQUENCE: 137
ttgacnnnnn nnnnnnnnnn nnntatatt                                29
```

```
<210> SEQ ID NO 138
<211> LENGTH: 29
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (6)..(23)
<223> OTHER INFORMATION: n is a, c, g, or t

<400> SEQUENCE: 138
ttgacnnnnn nnnnnnnnnn nnntatatt                                29

<210> SEQ ID NO 139
<211> LENGTH: 29
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (6)..(23)
<223> OTHER INFORMATION: n is a, c, g, or t

<400> SEQUENCE: 139
ttgacnnnnn nnnnnnnnnn nnntatact                                29

<210> SEQ ID NO 140
<211> LENGTH: 29
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (6)..(23)
<223> OTHER INFORMATION: n is a, c, g, or t

<400> SEQUENCE: 140
ttgacnnnnn nnnnnnnnnn nnntatact                                29

<210> SEQ ID NO 141
<211> LENGTH: 64
<212> TYPE: DNA
<213> ORGANISM: Bacillus subtilis

<400> SEQUENCE: 141
ttattttata aaatattaa aaagaaaagc aggaatatag caactcctta gtgaatatag    60
taaa                                                               64

<210> SEQ ID NO 142
<211> LENGTH: 57
<212> TYPE: DNA
<213> ORGANISM: Bacillus subtilis

<400> SEQUENCE: 142 atcattttaat tgatattatg tattgactta gacaactgaa ggtgttattc taatata     57

<210> SEQ ID NO 143
<211> LENGTH: 58
<212> TYPE: DNA
<213> ORGANISM: Bacillus subtilis

<400> SEQUENCE: 143 aaagaaaat gctaaaaagt tgttgacagt agcggcggta aatgttatga taataaag      58
```

<210> SEQ ID NO 144
<211> LENGTH: 59
<212> TYPE: DNA
<213> ORGANISM: Bacillus subtilis

<400> SEQUENCE: 144
tagtatttct tcaaaaaaac tattgcacta ttatttacta ggtggtatat tattattcg    59

<210> SEQ ID NO 145
<211> LENGTH: 58
<212> TYPE: DNA
<213> ORGANISM: Bacillus subtilis

<400> SEQUENCE: 145
aaaagaactt caaaaaaagt tattgacttc actgagtcaa cgagttataa taataaag    58

<210> SEQ ID NO 146
<211> LENGTH: 58
<212> TYPE: DNA
<213> ORGANISM: Bacillus subtilis

<400> SEQUENCE: 146
ttaaatactt tgaaaaagt tgttgactta aaagaagcta atgttatag taataaag    58

<210> SEQ ID NO 147
<211> LENGTH: 57
<212> TYPE: DNA
<213> ORGANISM: Bacillus subtilis

<400> SEQUENCE: 147
acaaaaaagt tttcctaagg tgtttacaag attttaaaaa tgtgtataat aagaaaa    57

<210> SEQ ID NO 148
<211> LENGTH: 58
<212> TYPE: DNA
<213> ORGANISM: Bacillus subtilis

<400> SEQUENCE: 148
cgaaaaaaca ttaaaaaact tcttgacttc aacatcaaat gatagtatga tagttaag    58

<210> SEQ ID NO 149
<211> LENGTH: 57
<212> TYPE: DNA
<213> ORGANISM: Bacillus subtilis

<400> SEQUENCE: 149
ggatattctt ttaaaaaagg tgttgactct gattcttgac cgtgttatat tattaaa    57

<210> SEQ ID NO 150
<211> LENGTH: 58
<212> TYPE: DNA
<213> ORGANISM: Bacillus subtilis

<400> SEQUENCE: 150
ggaaaataaa tcaaaaaaac atttgacaaa agaaagtcaa atgttatat taataaag    58

<210> SEQ ID NO 151
<211> LENGTH: 58
<212> TYPE: DNA
<213> ORGANISM: Bacillus subtilis

<400> SEQUENCE: 151
gtgtaatttt ttaaaaaagt tattgacttt gaagaagtga cattgtatac taataaag    58

<210> SEQ ID NO 152
<211> LENGTH: 58
<212> TYPE: DNA
<213> ORGANISM: Bacillus subtilis

<400> SEQUENCE: 152
ccaaaagttt ttaaaaaagt tgttgacttt gaagaagtga cgttgtatac taataaag    58

<210> SEQ ID NO 153
<211> LENGTH: 59
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t

<400> SEQUENCE: 153
dnrwdwwwwt tywaaaaark trttgacwdw rwwrwndvwa vrtkktatdh taatannwr    59

<210> SEQ ID NO 154
<211> LENGTH: 59
<212> TYPE: DNA
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (57)..(57)
<223> OTHER INFORMATION: n is a, c, g, or t

<400> SEQUENCE: 154
hrrwwwwwww yhwaaaaark tvttgachnh wwhwnwdwwh vrtgdtataw tawtawnhg    59

<210> SEQ ID NO 155
<211> LENGTH: 27
<212> TYPE: DNA
<213> ORGANISM: Bacillus licheniformis

<400> SEQUENCE: 155
gtttcacatt gaaagggag gagaatc    27

<210> SEQ ID NO 156
<211> LENGTH: 29
<212> TYPE: PRT
<213> ORGANISM: Bacillus subtilis

<400> SEQUENCE: 156

Met Arg Ser Lys Lys Leu Trp Ile Ser Leu Leu Phe Ala Leu Thr Leu
1               5                   10                  15

```
Ile Phe Thr Met Ala Phe Ser Asn Met Ser Ala Gln Ala
            20                  25
```